United States Patent
Hernandez Miguez et al.

(10) Patent No.: US 8,916,152 B2
(45) Date of Patent: Dec. 23, 2014

(54) S100A4 ANTIBODIES AND THERAPEUTIC USES THEREOF

(75) Inventors: Jose Luis Hernandez Miguez, Sant Boi de Llobregat (ES); Jaume Adan Plana, Mataro (ES); Josep Maria Martinez Escola, Barcelona (ES); Marc Masa Alvarez, Esparreguera (ES); Ramon Messeguer Peypoch, Premia de Mar (ES); Francesc Mitjans Prat, Igualada (ES); Sheila Dakhel Plaza, Esparreguera (ES); Antonio Coll Manzano, Barcelona (ES); Rosa Ma Hervas Villegas, L'Hospitalet de Llobregat (ES); Carme Calvis Calpe, L'Hospitalet de Llobregat (ES); Laura Padilla Garcia, Segur de Calafell (ES); Lourdes Tatiana Roque Navarro, Barcelona (CU); Laura Barbera Ferrando, Jesus-Tortosa (ES); Manuel Rivas Canas, Sant Boi de Llobregat (ES); Luis Angel Gomez Casajus, Barcelona (ES)

(73) Assignee: Lykera Biomed SA, Terrasa (ES)

( * ) Notice: Subject to any disclaimer, the term of this patent is extended or adjusted under 35 U.S.C. 154(b) by 0 days.

(21) Appl. No.: 13/704,333

(22) PCT Filed: Jun. 14, 2011

(86) PCT No.: PCT/EP2011/059868
§ 371 (c)(1),
(2), (4) Date: Dec. 14, 2012

(87) PCT Pub. No.: WO2011/157724
PCT Pub. Date: Dec. 22, 2011

(65) Prior Publication Data
US 2013/0101592 A1    Apr. 25, 2013

(30) Foreign Application Priority Data
Jun. 14, 2010    (EP) .................................... 10382170

(51) Int. Cl.
| | | |
|---|---|---|
| C07K 16/18 | (2006.01) |
| A61K 39/395 | (2006.01) |
| C12P 21/08 | (2006.01) |
| A61K 38/00 | (2006.01) |
| A61K 45/06 | (2006.01) |
| G01N 33/68 | (2006.01) |
| C07K 16/30 | (2006.01) |
| A61K 39/00 | (2006.01) |

(52) U.S. Cl.
CPC ........... *A61K 39/39558* (2013.01); *A61K 45/06* (2013.01); *C07K 2317/76* (2013.01); *G01N 33/6893* (2013.01); *A61K 39/3955* (2013.01); *C07K 16/18* (2013.01); *A61K 2039/505* (2013.01); *C07K 2317/33* (2013.01); *C07K 16/30* (2013.01); *C07K 2317/34* (2013.01)
USPC .................. 424/139.1; 424/141.1; 435/70.21; 436/548; 530/388.1; 514/13.3

(58) Field of Classification Search
None
See application file for complete search history.

(56) References Cited

U.S. PATENT DOCUMENTS

| | | | |
|---|---|---|---|
| 5,658,570 A | 8/1997 | Newman et al. |
| 5,801,142 A * | 9/1998 | Zain et al. .................... 514/21.2 |
| 5,837,243 A | 11/1998 | Deo et al. |
| 5,922,845 A | 7/1999 | Deo et al. |
| 5,969,108 A | 10/1999 | McCafferty et al. |
| 6,113,898 A | 9/2000 | Anderson et al. |
| 6,172,197 B1 | 1/2001 | McCafferty et al. |
| 6,706,266 B1 | 3/2004 | Life |
| 6,806,079 B1 | 10/2004 | McCafferty et al. |
| 7,291,332 B2 | 11/2007 | Life |
| 7,732,377 B2 | 6/2010 | McCafferty et al. |
| 8,003,101 B2 | 8/2011 | Life et al. |
| 2006/0269948 A1 | 11/2006 | Halloran |
| 2006/0269949 A1 | 11/2006 | Halloran |
| 2008/0039413 A1 | 2/2008 | Morris et al. |
| 2008/0057514 A1 | 3/2008 | Goldenring |
| 2008/0161203 A1 | 7/2008 | Su et al. |
| 2008/0193932 A1 | 8/2008 | Gasiewicz et al. |
| 2008/0234138 A1 | 9/2008 | Shaughnessy et al. |
| 2008/0307537 A1 | 12/2008 | Bachoo |
| 2009/0093005 A1 | 4/2009 | Smalley et al. |

FOREIGN PATENT DOCUMENTS

| | | |
|---|---|---|
| DE | 10017249 A1 | 10/2001 |
| EP | 0036676 A1 | 9/1981 |
| EP | 0052322 A2 | 5/1982 |
| EP | 0054951 A1 | 6/1982 |
| EP | 0088046 A2 | 9/1983 |
| EP | 0143949 A1 | 6/1985 |
| EP | 0239400 A2 | 9/1987 |
| EP | 0404097 A2 | 12/1990 |
| EP | 0566571 B1 | 10/1993 |

(Continued)

OTHER PUBLICATIONS

Flatmark et al., Immunofluorometric assay for the metastasis-related protein S100A4: release of S100A4 from normal blood cells prohibits the use of S100A4 as a tumor marker in plasma and serum, Tumor Biol. 25, 31-40, 2004.*

(Continued)

*Primary Examiner* — Elly-Gerald Stoica
(74) *Attorney, Agent, or Firm* — McCarter & English, LLP

(57) ABSTRACT

The invention relates to antibodies against S100A4, methods for the preparation of these antibodies, pharmaceutical compositions comprising these antibodies, and therapeutic and diagnostic uses thereof.

10 Claims, 11 Drawing Sheets

(56) References Cited

FOREIGN PATENT DOCUMENTS

| | | | |
|---|---|---|---|
| EP | 1169441 | B1 | 9/2002 |
| EP | 1439393 | A2 | 7/2004 |
| EP | 1477571 | A1 | 11/2004 |
| EP | 1644519 | B1 | 4/2006 |
| EP | 1657312 | A1 | 5/2006 |
| EP | 1811041 | A1 | 7/2007 |
| EP | 1953244 | A1 | 8/2008 |
| WO | 0064475 | A1 | 11/2000 |
| WO | 03016917 | A2 | 2/2003 |
| WO | 03051388 | A2 | 6/2003 |
| WO | 2005012569 | A1 | 2/2005 |
| WO | 2005067667 | A2 | 7/2005 |
| WO | 2006071081 | A1 | 7/2006 |
| WO | 2007071248 | A2 | 6/2007 |
| WO | 2007072225 | A2 | 6/2007 |
| WO | 2007114485 | | 10/2007 |
| WO | 2007126391 | A1 | 11/2007 |
| WO | 2008030278 | A2 | 3/2008 |
| WO | 2008037432 | A2 | 4/2008 |
| WO | 2008063413 | A2 | 5/2008 |
| WO | 2008063414 | A2 | 5/2008 |
| WO | 2008064670 | A2 | 6/2008 |
| WO | 2008069881 | A2 | 6/2008 |
| WO | 2008079269 | A2 | 7/2008 |
| WO | 2008079406 | A2 | 7/2008 |
| WO | 2008086342 | A2 | 7/2008 |
| WO | 2008121132 | A2 | 10/2008 |
| WO | 2008123866 | A2 | 10/2008 |
| WO | 2008137552 | A2 | 11/2008 |
| WO | 2008143639 | A2 | 11/2008 |

OTHER PUBLICATIONS

Paus et al., TD-11 workshop report: characterization of monoclonal antibodies to S100 proteins. Tumor Biol. 32, 1-12, 2011 (abstract).*
Bjornland K et al., "Expression of Matrix Metalloproteinases and the Metastasis-Associated Gene S100A4 in Human Neuroblastoma and Primitive Neuroectodermal Tumor Cells", J Pediatr Surg 2001, 36(7): 1040-44.
Ninomiya I et al., "Increased expression of SIOOA4 and its prognostic significance in esophageal squamous cell carcinoma", Int J Oncol 2001, 18(4): 715-20.
Oslejsková, L. et al., "Rheumatology (Oxford). 2009. 48, 1590-1594. Metastasis-inducing S100A4 protein is associated with the disease activity of rheumatoid arthritis", Oslejsková, L. et al. Rheumatology (Oxford). 2009, 48, 1590-1594.
Yonemura Y et al. "Inverse Expression of S100A4 and E-Cadherin Is Associated with Metastatic Potential in Gastric Cancer", Clin Cancer Res 2000, 6(11): 4234-42.
Zibert JR et al. "Significance of the S100A4 Protein in Psoriasis", J Invest Dermatology. 2010, 130(1): 150-60.
Agerbaek M et al., "Focal S100A4 Protein Expression Is an Independent Predictor of Development of Metastatic Disease in Cystectomized Bladder Cancer Patients", Eur Urol 2006. 50(4): 777-785.
Ambartsumian et al., "Metastasis of mammary carcinomas in GRS/a hybrid mice transgenic for the mts1 gene", Oncogene,1996;13(8):1621-1630.
Andersen K et al., "Expression of S100A4 combined with reduced E-cadherin expression predicts patient outcome in malignant melanoma", Mod Pathol 2004,17(8): 990-997.
Bandiera A et al., "Prognostic Factors and Analysis of S100a4 Protein in Resected Pulmonary Metastases from Renal Cell Carcinoma", World J Surg 2009, 33(7): 1414-20.
Belot N et al., "Extracellular S100A4 stimulates the migration rate of astrocytic tumor cells by modifying the organization of their actin cytoskeleton", Biochim Biophys Acta 2002,1600(1-2):74-83.
Bo G et al., "Analyses of differential proteome of human synovial fibroblasts obtained from arthritis", Clin Rheumatol. 2009, 28, 191-199.

Boye K. and Maelandsmo G.M. 2010., "S100A4 and Metastasis A Small Actor Playing Many Roles", The American Journal of Pathology, 176(2):528-535.
Brisset, A.C. et al., Intimal Smooth Muscle Cells of Porcine and Human Coronary Artery Express S100A4, a Marker of the Rhomboid Phenotype In Vitro, Circ Res. 2007, 100, 1055-1062.
Cho Y et al., "Overexpression of S100A4 is closely associated with progression of colorectal cancer", World J Gastroent 2005,11(31): 4852-6.
Cui J et al., "Differential proteomic analysis of human hepatocellular carcinoma cell line metastasis-associated proteins", J Can Res Clin Oncol 2004,130(10): 615-22.
De Silva Rudland S. et al., "Association of S100A4 and osteopontin with specific prognostic factors and survival of patients with minimally invasive breast cancer", 2006, Clin. Cancer Res. 12(4):1192-2000.
Ebralidze et al., "Isolation and characterization of a gene specifically expressed in different metastatic cells and whose deduced gene product has a high degree of homology to a Ca2+-binding protein family", Genes Dev, 1989; 3 (7):1086-1093.
Eckert RL et al., "S100 Proteins in the Epidermis", J Invest Dermatology. 2004, 123(1): 23-33.
Ford HL et al., "Interaction of metastasis associated Mts1 protein with nonmuscle myocin", Oncogene 1995,10 (8):1597-1605.
Greenway, S. et al., "S100A4/Mts1 Produces Murine Pulmonary Artery Changes Resembling Plexogenic Arteriopathy and Is Increased in Human Plexogenic Arteriopathy", Am J. Pathol. 2004, 164, 253-262.
Grigorian et al., "Modulation of mts1 expression in mouse and human normal and tumor cells", Electrophoresis. 1994;15(3-4):463-468.
Grigorian M et al., "Tumor Suppressor p53 Protein Is a New Target for the Metastasis-associated Mts1/S100A4 Protein", J Biol Chem 2001, 276(25):22699-708.
Grigorian M et al., "Tumor Suppressor p53 Protein Is a New Target for the Metastasis-associated Mts1/S100A4 Protein", Current Molecular Medicine 2008, 8(6):492-6.
Grum-Schwensen et al., "Suppression of Tumor Development and Metastasis Formation in Mice Lacking the S100A4 (mts1) Gene", Cancer Res. 2005; 65(9):3772-3780.
Hernan R et al., "ERBB2 Up-Regulates S100A4 and Several other Prometastatic Genes in Medulloblastoma", Cancer Res 2003, 63(1): 140-148.
Hodge, S. et al., "Posttransplant Bronchiolitis Obliterans Syndrome Is Associated with Bronchial Epithelial to Mesenchymal Transition", Am J Transplant. 2009, 9, 727-733.
Inoue T et al., "A case report suggesting the occurrence of epithelial-mesenchymal transition in obstructive nephropathy", Clin. Exp. Nephrol. 2009, 13, 385-388.
Kriajevska M.V. et al., "Non-muscle Myosin Heavy Chain as a Possible Target for Protein Encoded by Metastasis related mts-1 Gene*", 1994. The Journal of Biological Chemistry, 269(31):19679-19682.
Kriajevska M et al., "Liprin β1, a Member of the Family of LAR Transmembrane Tyrosine Phosphatase-interacting Proteins, Is a New Target for the Metastasis-associated Protein S100A4 (Mts1)*", J Biol Chem 2002, 277(7):5229-35.
Lawrie, A. et al., "Interdependent Serotonin Transporter and Receptor Pathways Regulate 5100A4/Mts1, a Gene Associated With Pulmonary Vascular Disease", Circ Res. 2005, 97, 227-235.
Le Hir M. et al., "Characterization of renal interstitial fibroblast-specific protein 1/S100A4-positive cells in healthy and inflamed rodent kidneys", Histochem Cell Biol. 2005, 123, 335-346.
Lloyd et al., "Human S100A4 (p9Ka) induces the metastatic phenotype upon benign tumour cells", Oncogene, 1998; 17(4):465-473.
Maelandsmo GM et al., "Different Expression and Clinical Role of S100A4 in Serous Ovarian Carcinoma at Different Anatomic Sites", Tumor Biol 2009, 30(1):15-25.
Masuda, K. et al., "Molecular profile of synovial fibroblasts in rheumatoid arthritis depends on the stage of proliferation", Arthritis Res. 2002, 4, R8.
Mathisen B et al., "S100A4 regulates membrane induced activation of matrix metalloproteinase-2 in osteosarcoma cells", Clin Exp Metastasis 2003, 20(8): 701-11.

(56) References Cited

OTHER PUBLICATIONS

Merklinger, S.L. et al., "Increased Fibulin-5 and Elastin in S100A4/Mts1 Mice With Pulmonary Hypertension", Circ Res. 2005, 97, 596-604.

Min HS et al., "S100A4 expression is associated with lymph node metastasis in papillary microcarcinoma of the thyroid", Mod Pathol 2008, 21(6): 748-55.

Moriyama-Kita M et al., "Correlation of S100A4 expression with invasion and metastasis in oral squamous cell carcinoma", Oral Oncol 2004, 40(5): 496-500.

Nakamura T et al., "Prognostic significance of S100A4 expression in gallbladder cancer", Int J Oncol 2002, 20(5): 937-41.

Pazzaglia L et al., "Activation of Metalloproteinases-2 and -9 by Interleukin-1. In S100A4-positive Liposarcoma Cell Line: Correlation with Cell Invasiveness", Anticancer Res 2004, 24(2B): 967-972.

Pedersen KB et al., "Sensitization of interferon-γ induced apoptosis in human osteosarcoma cells by extracellular S100A4", BMC Cancer 2004, 4:52.

Pedersen MV et al., "The Mts1/S100A4 Protein is a Neuroprotectant", J Neurosci Res 2004, 77(6):777-86.

Peng, T. et al., "Plasma Levels of S100A4 in Portopulmonary Hypertension", Biomarkers. 2009, 14, 156-160.

Rosty C et al., "Overexpression of S100A4 in Pancreatic Ductal Adenocarcinomas Is Associated with Poor Differentiation and DNA Hypomethylation", Am J Pathol 2002, 160(1): 45-50.

Rudland PS et al., "Prognostic Significance of the Metastasis-inducing Protein S100A4 (p9Ka) in Human Breast Cancer", Cancer Res 2000, 60(6): 1595-1603.

Saleem M et al., "S100A4 accelerates tumorigenesis and invasion of human prostate cancer through the transcriptional regulation of matrix metalloproteinase 9", PNAS 2006, 103(40): 14825-30.

Schmidt-Hansen et al., "Functional Significance of Metastasis-inducing S100A4(Mts1) in Tumor-Stroma Interplay*", J. Biol. Chem. 2004, 279(23):24498-24504.

Spiekerkoetter, E. et al., "Reactivation of gHV68 induces neointimal lesions in pulmonary arteries of S100A4/Mts1-overexpressing mice in association with degradation of elastin", Am J Physiol Lung Cell Mol Physiol. 2008, 294, L276-289.

Strutz F. et al., "Role of basic fibroblast growth factor-2 in epithelial-mesenchymal transformation", Kidney Int. 2002;61 (5):1714-1728.

Tsuna M et al., "Significance of S100A4 as a Prognostic Marker of Lung Squamous Cell Carcinoma", Anticancer Res 2009, 29(7): 2547-54.

Xie R et al., "S100A4 mediates endometrial cancer invasion and is a target of TGF-b1 signaling", Lab Invest 2009, 89 (8): 937-947.

Yamaguchi Y et al., "Epithelial-Mesenchymal Transition as a Potential Explanation for Podocyte Depletion in Diabetic Nephropathy", Am J Kidney Dis. 2009, 54, 653-664.

Semov, "Metastasis-associated Protein S100A4 Induces Angiogenisis through interaction with Annexin II and Accelerated Plasmin Formation," Journal of Biological Chemistry, vol. 280, No. 21.

Kriajevska M et al., "Liprin β, a Member of the Family of LAR Transmembrane Tyrosine Phosphatase-interacting Proteins, Is a New Target for the Metastasis-associated Protein S100A4 (Mts1)*", J Biol Chem 2002, 277(7):5229-35.

Mathisen B et al., "S100A4 regulates membrane induced activation of matrix metalloproteinase-2 in osteosarcoma cells", Clin Exp Metastasis 2003, 20(8): 701-11.

Nakamura T et al., "Prognostic significance of S100A4 expression in gallbladder cancer,"Int J Oncol 2002, 20(5): 937-41.

Schmidt-Hansen et al., "S100A4 mediates endometrial cancer invasion and is a target of TGF-b1 signaling", J. Biol. Chem. 2004; 279(23):24498-24504.

International Search Report for International Application No. PCT/EP2011/059868, mailed Oct. 24, 2011.

European Search Report for Application No. EP10382170, dated Mar. 4, 2011.

Dukhanina, et al., "Comparative analysis of secretion of S100A4 metastatic marker by immune and tumor cells," Bulletin of Experimental Medicine, p. 78-80, (Jan. 2008).

Zhang et al., "A Novel Monoclonal Antibody Against Human S100A4", Calcium Binding Proteins, vol. 1, No. 4, p. 219-223 (2006).

Geradts et al., "Immunohistochemical p16INK4a analysis of archival tumors with deletion, hypermethylation, or mutation of the CDKN2/MTS1 gene. A comparison of four commercial antibodies, Applied Immunohistochemistry & Molecular Morphology:" AIMM/Official Publication of the Society for Applied Immunohistochemistry, vol. 8, No. 1, p. 71-79 (Mar. 2000).

Semov, "Metastasis-associated Protein S100A4 Induces Angiogenisis through interaction with Annexin II and Accelerated Plasmin Formation," Journal of Biological Chemistry, vol. 280, No. 21, 20833-41, 2005.

Ambartsumian et al., "The metastasis-associated Mts1(S100A4) protein could act as an angiogenic factor", © 2001 Nature Publishing Group, Oncogene (2001) 20, 4685-4695.

\* cited by examiner

A

B

A

B

A

B

A

B

S100A4 ANTIBODIES AND THERAPEUTIC USES THEREOF

The present application is a 371 of International Application No. PCT/EP2011/059868, filed Jun. 14, 2011, which claims the benefit of European Application No. EP10382170.8 filed Jun. 14, 2010. Each of the above-referenced applications are hereby incorporated by reference in their entirety.

FIELD OF THE INVENTION

The invention relates to molecular immunology and the treatment of human diseases. In particular, it relates to antibodies against human S100A4, pharmaceutical compositions comprising these antibodies, and therapeutic and diagnostic uses thereof.

BACKGROUND OF THE INVENTION

Cancers are the most frequent type of human malignancies, and the fatality of cancer predominantly results from the dissemination of primary tumor cells to distant sites and the subsequent formation of metastases.

The causal implication of metastasis-inducing S100A4 protein, a member of the S100 family of calcium-binding proteins, in tumor progression, angiogenesis, and metastatic dissemination has been demonstrated by several approaches.

S100A4 plays a pivotal role in the tumor-stroma cross-talk that occurs between tumor cells and their stroma (including fibroblasts, endothelial, smooth muscle, inflammatory, and neural cells) mainly mediated by direct cell-cell contact or autocrine/paracrine cytokine and growth factor signalling. For example, epithelial growth factor, tumor growth factor-β1, and fibroblast growth factor-2 are able to stimulate the expression of S100A4 (Strutz et al. Kidney Int. 2002; 61(5): 1714-1728); S100A4 released either by tumor or stroma cells into the tumor environment triggers pro-metastatic cascades in tumor cells (Grum-Schwensen et al. Cancer Res. 2005; 65(9):3772-3780); tumor cells or tumor-associated fibroblasts, in contrast to the normal fibroblasts, express high levels of S100A4 (Ambartsumian et al. Oncogene. 1996; 13(8):1621-1630); other host-derived tumor stroma cells, such as lymphocytes and macrophages, increase expression of S100A4 upon activation (Grigorian et al. Electrophoresis. 1994; 15(3-4):463-468).

S100A4 also influences tumor angiogenesis via the stimulation and remodelling of the extracellular matrix (production of degrading enzymes) and the motility of endothelial cells acting as a proangiogenic factor (Schmidt-Hansen et al. J. Biol. Chem. 2004; 279(23):24498-24504).

The S100A4 gene itself was originally isolated as a gene differentially expressed in highly metastatic mouse mammary adenocarcinoma (Ebralidze et al. Genes Dev. 1989; 3(7):1086-1093). It has also been demonstrated that the introduction of the S100A4 gene into non-metastatic tumor cell lines as well as its gene suppression in metastatic ones modified the tumorigenic and metastatic fate of such cells, therefore proving its involvement in tumor progression and metastasis formation (Lloyd et al. Oncogene. 1998; 17(4): 465-473).

In the clinic, positive correlation between high levels of expression of S100A4 and poor prognosis in cancer patients has been demonstrated for breast carcinoma (Rudland P S et al. Cancer Res 2000. 60(6): 1595-1603), prostate carcinoma (Saleem M et al. PNAS 2006. 103(40): 14825-30), lung carcinoma (Tsuna M et al. Anticancer Res 2009. 29(7): 2547-54), colorectal carcinoma (Cho Y et al. World J Gastroent 2005. 11(31): 4852-6), pancreatic carcinoma (Rosty C et al. Am J Pathol 2002. 160(1): 45-50), renal carcinoma (Bandiera A et al. World J Surg 2009. 33(7): 1414-20), gastric carcinoma (Yonemura Y et al. Clin Cancer Res 2000. 6(11): 4234-42), ovarian carcinoma (Maelandsmo G M et al. Tumor Biol 2009. 30(1):15-25), papillary thyroid carcinoma (Min H S et al. Mod Pathol 2008. 21(6): 748-55), melanoma (Andersen K et al. Mod Pathol 2004. 17(8): 990-997), hepatocellular carcinoma (Cui J et al. J Can Res Clin Oncol 2004. 130(10): 615-22), bladder carcinoma (Agerbaek M et al. Eur Urol 2006. 50(4): 777-785), liposarcoma invasive carcinoma (Pazzaglia L et al. Anticancer Res 2004. 24(2B): 967-972), neuroblastoma (Bjornland K et al. J Pediatr Surg 2001. 36(7): 1040-44), esophageal squamous carcinoma (Ninomiya I et al. Int J Oncol 2001. 18(4): 715-20), osteosarcoma (Mathisen B et al. Clin Exp Metastasis 2003. 20(8): 701-11), gallbladder carcinoma (Nakamura T et al. Int J Oncol 2002. 20(5): 937-41), oral squamous carcinoma (Moriyama-Kita M et al. Oral Oncol 2004. 40(5): 496-500), endometrial carcinoma (Xie R et al. Lab Invest 2009. 89(8): 937-947), and medulloblastoma (Hernan R et al. Cancer Res 2003. 63(1): 140-148), amongst others.

Implications of S100A4 in various non-malignant pathological conditions have also been demonstrated by a number of research groups, in particular, in pathologies such as autoimmune inflammation and disorders in cardio-vascular, nervous, and pulmonary systems (Grigorian M et al. Current Molecular Medicine 2008. 8(6):492-6). S100A4 is therefore a candidate target for clinical applications. However, due to the complexity of the biological function of S100A4 and its unknown entire mechanism of action, no inhibitors yet exist that block either the intracellular or extracellular functions of this protein.

Antibody-based therapy has emerged as an integral part of effective treatments for a number of diseases. In the last decade, monoclonal antibodies have become major therapeutic agents in the treatment of malignant and nonmalignant diseases.

To date, monoclonal and polyclonal antibodies raised against S100A4 have been provided by different companies and research groups (Zhang et al, Calcium Binding Proteins 2006. 1:4, 219-223; ABIN167355 and ABIN171123 from antibodies-online GmbH, Germany; A5114 from DakoCytomation, Denmark; among others). Although scientific and patent teachings speculate on the therapeutic applications of these antibodies, to the best knowledge of the inventors, there is yet no evidence on file that the antibodies of the state of the art have actually solved the problem of treating cancer and non-malignant diseases.

WO2000064475 (Research Corporation Technologies, Inc.) discloses a method for the diagnosis of malignant cancer (i) by inhibiting the mts-1 protein with antibodies directed against the mts-1 protein (antibodies can be conjugated to a toxin) or (ii) by providing a nucleic acid encoding an antisense mts-1 nucleotide sequence.

Therefore, there is a need in the state of the art to provide new therapeutic approaches for the treatment of cancer, particularly for the treatment of angiogenesis and metastasis, targeting the S100A4 protein.

In addition, at a diagnostic level, S100A4 can be considered a good marker in the differentiation process of a normal cell towards a tumor cell, and therefore it is a good biomarker in the cytological examination of tumors. However, the detection of the expression of S100A4 in cancerous tissue presents the drawback of requiring a patient biopsy. Therefore, there is a need in the state of the art to provide a simpler and less invasive method for the clinical diagnosis of cancer by means of detecting the levels of S100A4 in a subject.

SUMMARY OF THE INVENTION

In a first aspect, the invention relates to a specific anti-S100A4 antibody having anti-angiogenic activity or a fragment thereof which substantially preserves the anti-angiogenic activity of said antibody wherein the antibody is selected from the group consisting of:
(i) An antibody that recognizes an epitope of S100A4 comprising the sequence ELPSFLGKRT (SEQ ID NO: 3),
(ii) An antibody that recognizes an epitope of S100A4 comprising the sequence EGFPDKQPRKK (SEQ ID NO: 24) and
(iii) An antibody produced by the hybridoma ECACC 11051804.

In another aspect, the invention relates to a hybridoma cell line selected from the group consisting of a cell line deposited with accession number ECACC 10022401, ECACC 11051801, ECACC 11051802, ECACC 11051803 and ECACC 11051804.

In another aspect, the invention relates to a pharmaceutical composition comprising a pharmaceutically effective amount of at least one antibody or a fragment thereof according to the invention and at least one pharmaceutically acceptable carrier.

In yet another aspect, the invention relates to an antibody or fragment thereof according to the invention for use in the prevention and/or treatment of a disease selected from metastasis and a disease associated to an undesired angiogenesis.

In additional aspects, the invention relates to a conjugate comprising an antibody or a fragment thereof according to the invention and a second component selected from the group of:
(a) an antiangiogenic agent
(b) an antimetastatic agent
(c) a cytotoxic agent
(d) an anti-inflammatory agent
as well as to the uses thereof in the prevention and/or treatment of a disease selected from a metastasis, a disease associated to an undesired angiogenesis and a disease associated with inflammation.

In another aspect, the invention relates to a method for obtaining a monoclonal antibody according to the invention which comprises culturing a hybridoma cell line selected from those cell lines deposited with accession number ECACC 10022401, ECACC 11051801, ECACC 11051802, ECACC 11051803 and ECACC 11051804 in conditions which allow the production of said antibody.

In additional aspects, the invention relates to the composition comprising a specific anti-S100A4 antibody and an antimetabolite as well as to the uses thereof in the prevention and/or the treatment of cancer or metastasis.

In another aspect, the invention relates to the use of an antibody that binds specifically to the S100A4 protein or of a fragment thereof with capacity for binding to the antigen for the preparation of a medicament for the prevention and/or treatment of a disease associated with inflammation.

In yet another aspect, the invention relates to an in vitro method for diagnosing cancer or a disease associated with inflammation in a subject which comprises:
(a) detecting the levels of the S100A4 protein or of a variant thereof in a biofluid of said subject by means of using a monoclonal antibody produced by a hybridoma selected from the group consisting of ECACC 10022401, ECACC 11051801, ECACC 11051802, ECACC 11051803 and ECACC 11051804 or a functional variant of said antibody
(b) comparing said levels with a reference value
wherein increased levels of the S100A4 protein or of a variant thereof with respect to the reference value are indicative of the subject suffering from cancer or a disease associated with inflammation.

In yet another aspect, the invention relates to a method for detecting S100A4 in a sample which comprises:
(i) contacting a sample suspected of containing S100A4 with a specific anti-S100A4 antibody or a fragment thereof as defined in the invention
(ii) detecting the formation of immune complexes between S100A4 and the antibody or the fragment thereof
wherein the detection of immune complexes between S100A4 and the antibody is indicative of the presence of S100A4 in the sample.

In another aspect, the invention relates to a kit for diagnosing cancer or a disease associated with inflammation in a biofluid which comprises at least one antibody or a fragment thereof according to the invention.

In another aspect, the invention relates to an in vitro method for designing a customized therapy for a subject diagnosed with cancer which comprises detecting the levels of the S100A4 protein or of a variant thereof in a biofluid of said subject by means of using a monoclonal antibody produced by a hybridoma selected from the group consisting of ECACC 10022401, ECACC 11051801, ECACC 11051802, ECACC 11051803 and ECACC 11051804 or a functional variant of said antibody before and after the therapy with the same monoclonal antibody, wherein an increase of the levels of S100A4 protein or of a variant thereof after the therapy with respect to the levels of S100A4 or of a variant thereof, before the therapy, is indicative that the patient needs an alternative therapy to the therapy originally administered.

It is an object of the present invention to provide antibodies that specifically bind to human or murine S100A4 and not to the other S100 family proteins.

It is an object of the present invention to provide antibodies that sensitively bind to human or murine S100A4 in a limit of detection of nanograms, even picograms.

It is importantly, an object of the present invention to provide therapeutic antibodies against S100A4 with a demonstrated activity against malignant and nonmalignant diseases.

It is importantly, an object of the present invention to provide therapeutic antibodies against S100A4 with a demonstrated activity in vivo against malignant and nonmalignant diseases, without being metabolized or degraded prior to effecting its function in the body.

Importantly, it is an object of the present invention to provide therapeutic antibodies against S100A4 with a demonstrated activity against malignant and nonmalignant diseases while effecting minimal or no toxic effects.

It is an object of the present invention to provide antibodies against S100A4 that can inhibit tumor growth.

It is an object of the present invention to provide antibodies against S100A4 that can inhibit tumor development.

It is an object of the present invention to provide antibodies against S100A4 that can inhibit angiogenesis and tumor angiogenesis.

It is an object of the present invention to provide antibodies against S100A4 that can inhibit endothelial cell migration.

It is an object of the present invention to provide antibodies against S100A4 that can inhibit cancer stem cells.

It is an object of the present invention to provide antibodies against S100A4 that can inhibit inflammatory processes

Quantifications were made analizing between 8 and 39 pictures per slice depending on the size of tumours at a magnification of X 120. Images were analized using the NIH ImageJ imaging software. Graphs show the mean±s-d *p<0.05 ("Mann-Whitney test").

Figure 8:
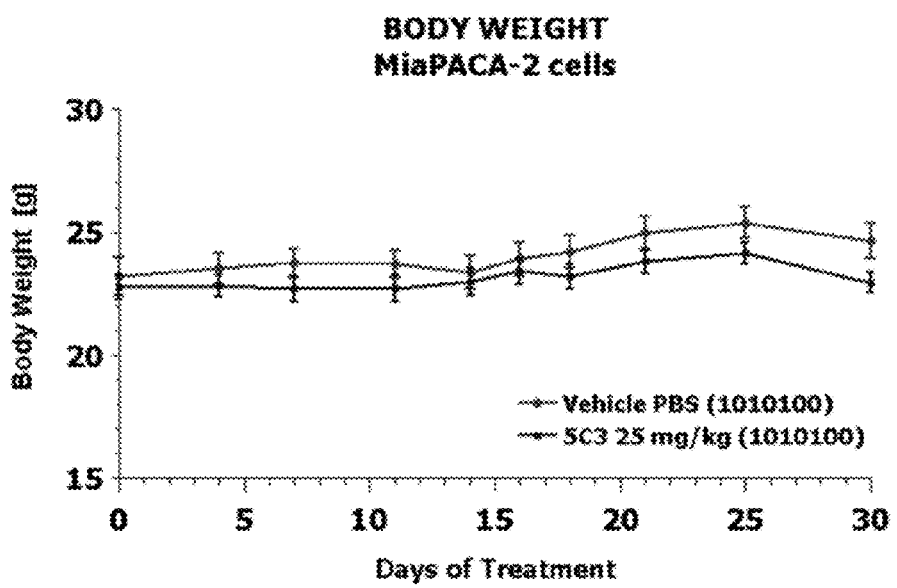
Figure 8:
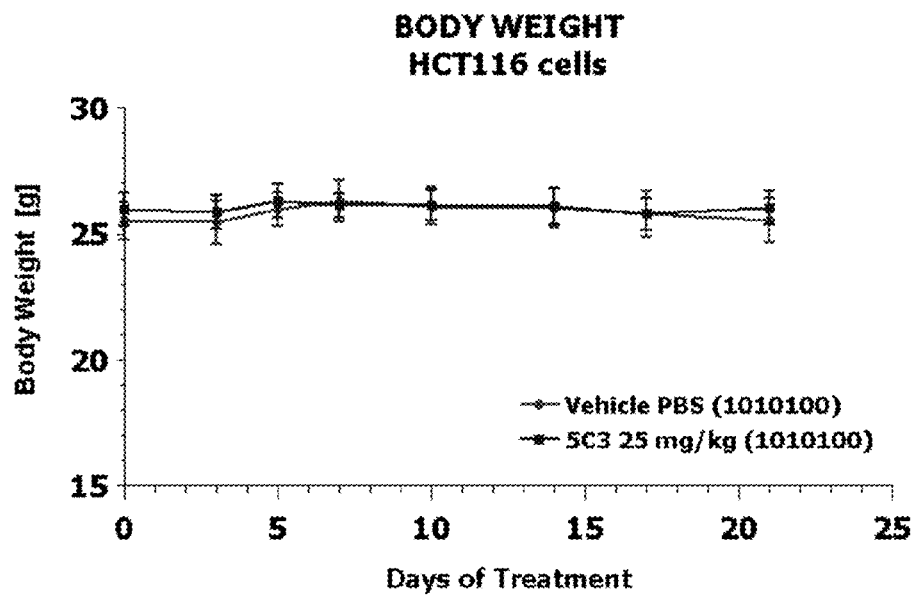

FIG. 8. Monoclonal antibody 5C3 shows no toxic effects in vivo. Female, athymic, nude mice were inoculated subcutaneously with $5 \times 10^6$ MiaPACA-2 cells or $1 \times 10^6$ HCT116 cells in 0.1 ml culture medium without supplements, into the right upper flank of mice on day 0. When tumors reached 65-160 mm³ for MiaPACA-2 or 155-370 mm³ for HCT116 cells, the treatment was initiated. Treatment groups had either 10 animals or 7 animals for MiaPACA-2 or HCT116 cells respectively. PBS (negative control) or 5C3 (25 mg/kg) was given intraperitoneally three times a week (1010100). Final formulation buffer was given as vehicle control. Body weight was measured three times per week along the experiment. Graph of body weight show the mean±s-d.

Figure 9:
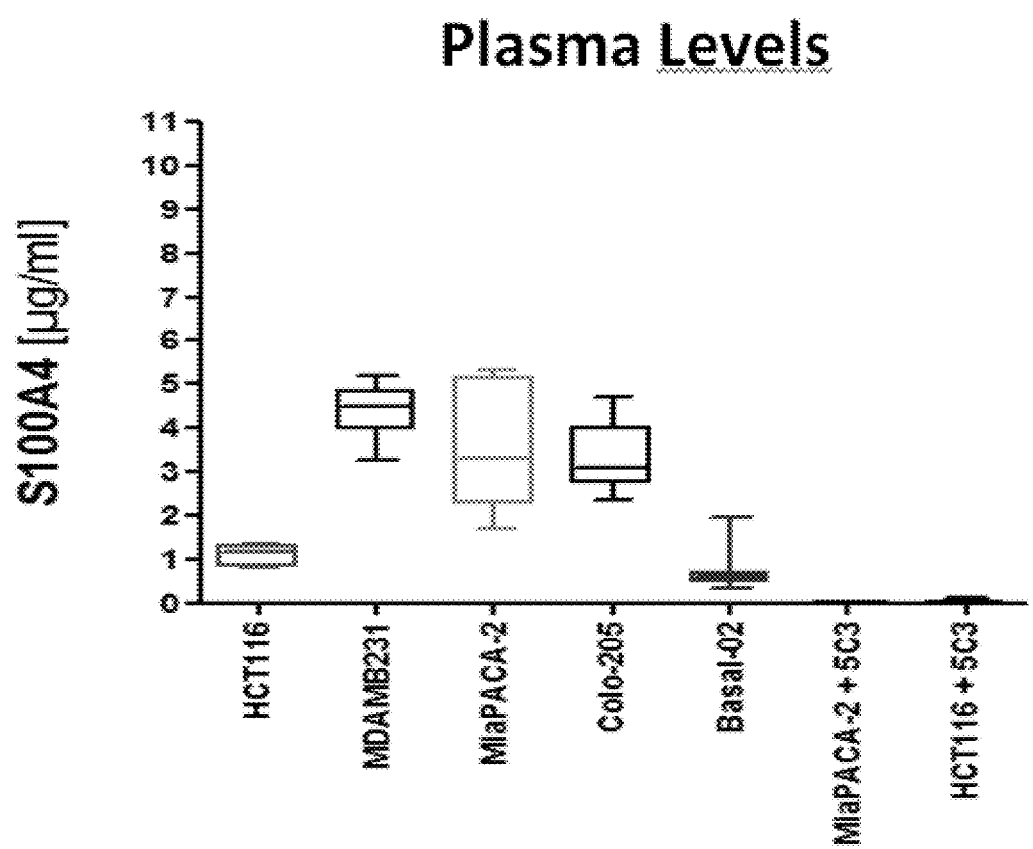

FIG. 9. Determination of plasma levels of S100A4. Plasma levels of S100A4 protein on several xenograft models in athymic mice (MiaPACA-2, HCT116, MDAMB-231, Colo205) compared with S100A4 levels in animals without tumor (Basal-02) were determined by sandwich ELISA method. MiaPACA-2+5C3 and HCT116+5C3 conditions represent the levels of S100A4 in plasma, unbound to the 5C3 monoclonal antibody. Plasma levels were measured at the end of the experiment. Graph of plasma levels show the mean±s-d.

Figure 10:
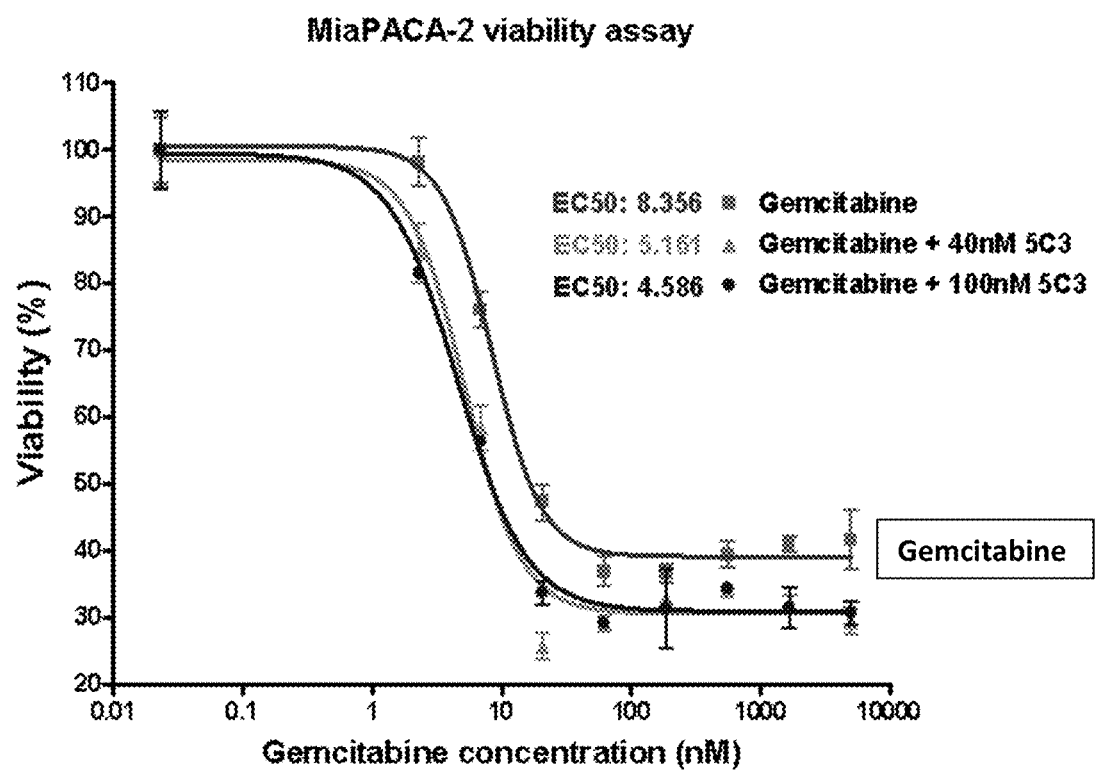

FIG. 10. Synergistic effect of Gemcitabine combined with monoclonal antibody 5C3 in cell viability. Effect of Gemcitabine alone or combined with monoclonal antibody 5C3 on cell viability measured by hexosaminidase activity. Cytotoxic dose-response effect of Gemcitabine is improved synergistically with the combination of the monoclonal antibody 5C3. MiaPACA-2 cells were incubated with the chemotherapeutic drug in different doses with or without 5C3, at a constant concentration of 40 nM or 100 nM, for 72 h. The viability was normalized to the positive control, cells without compounds (gemcitabine or 5C3), that represents the 100% of viability.

Figure 11:
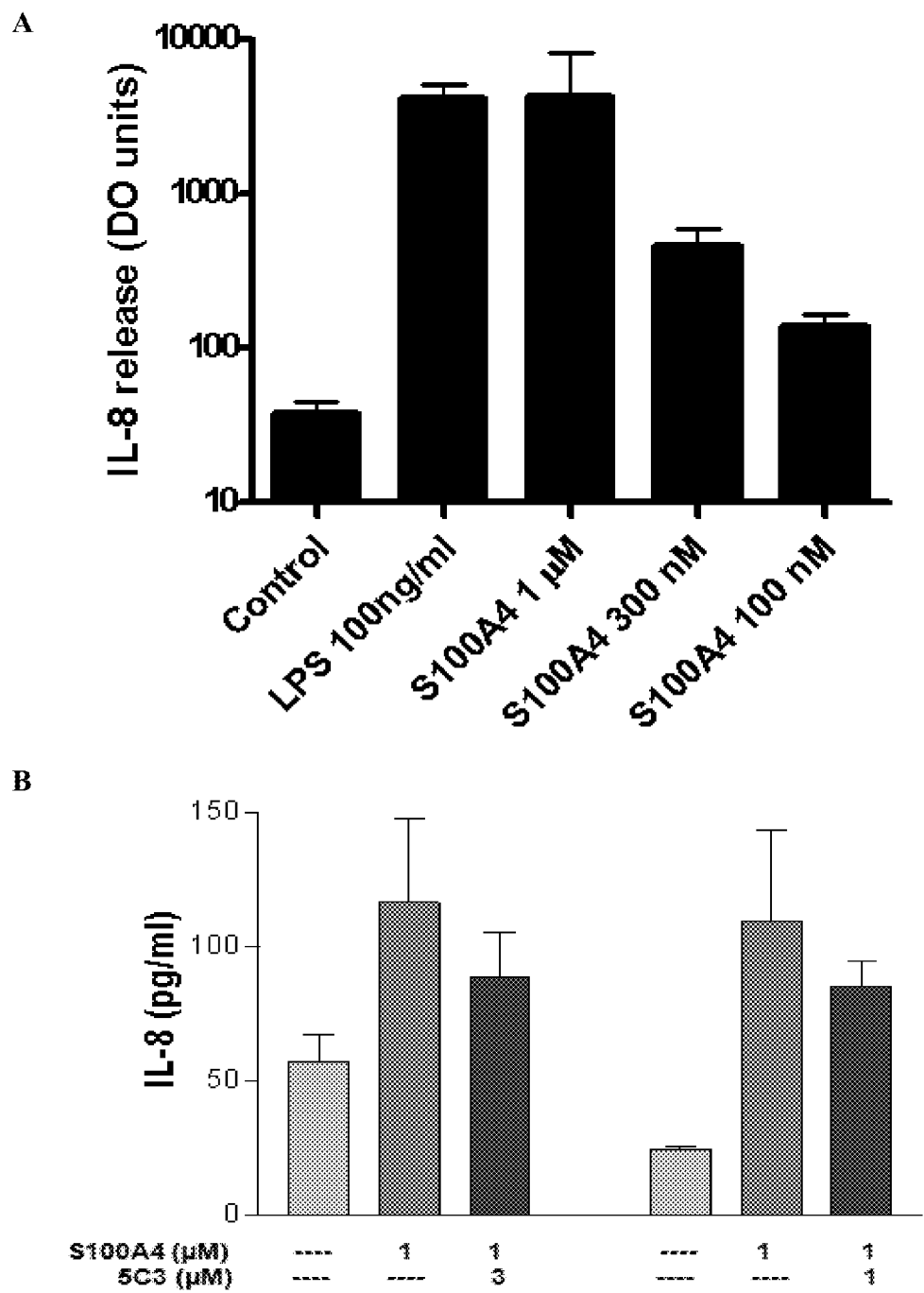

FIG. 11 Inhibitory effect of monoclonal antibody 5C3 on IL-8 release induced by S100A4 in THP-1 monocytes. (A) Dose response of S100A4 on IL-8 secreted by THP-1 monocytes after 24 hours of incubation and compared with the secretion induced by LPS (positive control). (B) Effect of 5C3, on IL-8 release in THP-1 monocytes treated with S100A4 at 3 µM for 24 hours. Cells were always treated with anti-mouse IgG (Fc specific) to avoid Fc receptor-induced IL-8 release. IL-8 from supernatants was analyzed by ELISA. Values represent mean±sd.

DESCRIPTION OF THE INVENTION

The authors of the present invention have discovered that, unexpectedly, monoclonal antibodies directed against the S100A4 protein are capable of neutralizing the S100A4-induced migration of endothelial cells in an in vitro motility assay (see example 9) as well as neutralizing the angiogenic capacity induced by S100A4 both in a xenograft tumor model (see example 11). These results indicate that the anti-S100A4 antibodies are useful for the prevention and/or treatment of diseases associated to an undesired angiogenesis and metastasis, such as cancer.

The present invention provides monoclonal antibodies directed against the human and murine S100A4 protein, designated as 5C3, 1E2, 6B9, 5A3 and 8B6, which specifically interact with and block S100A4 angiogenic activity. The inventors have surprisingly found that these antibodies have valuable pharmacological activities since they block tumor development, tumor angiogenesis, and have, moreover, no or minimal toxic side effects in vivo. Interestingly, the work performed by the inventors has revealed a new blocking mechanism of action of said antibodies in the endothelial cell migration induced by S100A4.

The authors of the present invention have additionally demonstrated that the levels of S100A4 in a biofluid are suitable as a diagnostic marker for the early detection of cancer. Therefore, the present invention also relates to an in vitro method and to kits for the diagnosis of cancer in a patient by means of detecting the levels of S100A4 in a biofluid with said antibodies.

Anti-angiogenic Antibodies of the Invention

In a first aspect, the invention relates to a specific anti-S10A4 antibody having anti-angiogenic activity or a fragment thereof which substantially preserves the anti-angiogenic activity of said antibody wherein the antibody is selected from the group consisting of:
  (i) An antibody that recognizes an epitope of S100A4 comprising the sequence ELPSFLGKRT (SEQ ID NO: 3),
  (ii) An antibody that recognizes an epitope of S100A4 comprising the sequence EGFPDKQPRKK (SEQ ID NO: 24) and
  (iii) An antibody produced by the hybridoma ECACC 11051804.

As used herein in the first aspect of the invention, the term "antibody" relates to a monomeric or multimeric protein which comprises at least one polypeptide having the capacity for binding to a determined antigen and comprising all or part of the light or heavy chain variable region of an immunoglobulin molecule. The term antibody includes any type of known antibody, such as, for example, polyclonal antibodies, monoclonal antibodies and genetically engineered antibodies, such as chimeric antibodies, humanized antibodies, primatized antibodies, human antibodies and bispecific antibodies. A more extensive definition of the term "antibody" can be found on the "Definitions" section. The terms "polyclonal antibodies" and "monoclonal antibodies" are defined in the "Definitions" section. In a particular embodiment, the antibody is a monoclonal antibody.

"Chimeric antibodies" are understood as antibodies constructed with variable regions of an antibody of a species (usually a mammal in which the monoclonal antibody was generated) and constant regions of another species (that species in which the chimeric antibody is going to be used). The objective of said construct is to obtain an antibody with the original monoclonal antibody but which is less immunogenic and better tolerated in the subject who is going to be treated, with an improved serum half-life and which can be recognized by immunological effector mechanisms, i.e., the complement, the Fc receptor of cytotoxic cells or other specific immunoglobulin receptors which show species specificity. In a preferred embodiment, the chimeric antibodies are formed by murine variable regions and human constant regions.

"Humanized antibody" is understood as an antibody from a non-human organism, typically a murine antibody, which conserves the antigen binding properties of the parent antibody, but which is less immunogenic in human beings. This can be achieved by means of different processes, which include (a) grafting the complete nonhuman variable domains into human constant regions to generate chimeric antibodies; (b) grating only the nonhuman complementarity determining regions (CDR) in a human framework and the constant regions, with or without retaining the critical framework residues; and (c) transplanting the complete nonhuman variable domains, but "concealing them" with a section similar to the human variable domain by means of replacing the surface residues.

"Primatized antibody" is understood as a recombinant antibody that has been genetically manipulated to contain the heavy and light variable domains of a monkey antibody (or of another primate), particularly an antibody of a cynomolgus monkey, and containing sequences of a human constant domain, preferably the constant domain of human gamma 1 or 4 immunoglobulin (or a PE variant). The preparation of said antibodies is described in Newman et al., Biotechnology, 10: 1458-1460 (1992); and in patent documents U.S. Pat. Nos. 5,658,570 and 6,113,898. It has been described that these antibodies show a high degree of homology with human antibodies, i.e., 85-98%, they have human effector functions, they have lower immunogenicity and can show a high affinity for human antigens. Another very effective means for generating recombinant antibodies is described by Newman, Biotechnology, 10: 1455-1460 (1992).

"Human antibody" is understood as an antibody integrally containing human light and heavy chains as well as constant regions, produced by means of any of the known standard methods. A more extensive definition is found on the "Definitions" section.

The term "bispecific antibodies" or "bifunctional antibodies" is defined on the "Definitions" section.

The invention also comprises the use of fragments of the different types of antibodies mentioned above which substantially preserve the anti-angiogenic activity of the antibody. The term "antibody fragment" includes antibody fragments such as Fab, F(ab')2, Fab', single chain Fv fragments (scFv), diabodies and nanobodies.

Papain digestion of antibodies produces two identical antigen binding fragments referred to as "Fab" fragments, each with a single antigen binding site, and a residual "Fc" fragment, the name of which reflects its capacity for readily crystallizing. Pepsin treatment yields an F(ab')2 fragment which has two antigen binding sites and which is still capable of cross-linking to the antigen.

"Fv" is the minimal antibody fragment containing a complete antigen binding and antigen recognition site. This region consists of a variable domain of a variable light chain and heavy chain dimer in a strong noncovalent association. In this configuration the three hypervariable regions of each variable domain interact to define an antigen binding site on the surface of the VH-VL dimer. As a whole, the six hypervariable regions confer antigen-antibody specificity to the antibody. However, even a single variable domain (or half an Fv, which comprises only three hypervariable regions specific for an antigen) has antigen recognition and binding capacity, although with less affinity than the complete binding site.

The Fab fragment also contains the constant domain of the light chain and the first constant domain (CH1) of the heavy chain. Fab' fragments differ from Fab fragments in the addition of a few residues at the carboxy terminus of the domain CH1 of the heavy chain, including one or more cysteines of the antibody hinge region.

The "single chain Fv" or "scFv" antibody fragments comprise the VH and VL domains of an antibody, in which these domains are present in a single polypeptide chain. Preferably, the Fv polypeptide additionally comprises a linker polypeptide between the VH and VL domains which allows the scFv to form the desired structure for antigen binding. For a review of scFv, see Pluckthun in The Pharmacology of Monoclonal Antibodies, vol. 113, Rosenburg and Moore eds., Springer-Verlag, N.Y., pp. 269-315 (1994).

The term "diabodies" refers to small antibody fragments with two antigen binding sites, those fragments comprising a heavy chain variable domain (VH) connected to a light chain variable domain (VL) in the same polypeptide chain (VH-VL). By means of using a linker which is too short to allow pairing between the two domains in the same chain, the domains are forced to pair with the complementary domains of another chain and create two antigen binding sites. Diabodies are described in further detail in, for example, documents EP 404,097; WO 93/11161; and Hollinger et al., Proc. Natl. Acad. Sci. USA, 90: 6444-6448 (1993).

The term "nanobodies" designates small sized entities (15 kDa) formed solely by the antigen binding region of the heavy chain (VH fragment) of immunoglobulins. Said nanobodies are mainly produced after immunizing animals of the Camelidae family, such as camels, llamas and dromedaries, mainly llamas; and also of the shark family, which have the particularity of having antibodies which naturally lack the light chain and recognize the antigen by the heavy chain variable domain. Nevertheless, the nanobodies derived from these sources require a humanization process for their therapeutic application. Another potential source for obtaining nanobodies is from antibodies derived from different human samples by separating the VH and VL domains of the variable region. Nanobodies present advantages such as a production cost reduction with respect to whole antibodies, stability and the reduction of immunogenicity.

Other antibody fragments are listed on the "definitions" section.

The antibodies according to the present invention have anti-angiogenic activity. The expression "having antiangioenic activity", as used herein, refers to the ability of the antibodies to inhibit S100A4-induced angiogenesis. The anti-angiogenic activity can be determined in vitro by determining the ability of the antibody or fragment thereof to block the migration of the S100A4-induced migration HUVEC cells as shown for instance in example 9 of the present application or in vivo by determining the ability of the antibody to block the formation of tumor vasculature in carcinomas derived from the implantation of tumor cells overexpressing S100A4 as described in example 11 of the present invention. According to the present invention, an anti-S100A4 antibody is considered as being antiangiogenic if it blocks at least 100%, at least 90%, at least 80%, at least 70%, at least 60%, at least 50%, at least 40%, at least 30%, at least 20% or at least 10% of the angiogenic activity of the S100A4 protein.

The antibody fragments included in the first aspect of the present invention conserve the capacity for binding to the S100A4 antigen of the whole antibody from which they derive and they also preserve the function of inhibiting the angiogenic activity of the S100A4 protein.

The term "preserve the anti-angiogenic activity of the specific anti-S100A4 protein", as used herein, refers to the ability of the antibody fragment to show substantially the anti-angiogenic activity than the complete antibody. The antiangiogenic activity can be determined in vitro by determining the ability of the antibody or fragment thereof to block the migration of the S100A4-induced migration HUVEC cells as shown for instance in example 9 of the present application or in vivo by determining the ability of the antibody to block the formation of tumor vasculature in carcinomas derived from the implantation of tumor cells overexpressing S100A4 as described in example 11 of the present invention. The inhibition of the formation of tumor vasculature can be measured as a decrease in the number of microvessels in comparison with animals not treated with the antibody or as a decrease in the density of microvessels in comparison with animals not treated with the antibody. An antibody fragment preserves the anti-angiogenic activity of the antibody if it shows at least 100%, 99%, 98%, 97%, 96%, 95%, 94%, 93%, 92%, 91%, 90%, 85%, 80%, 75%, 70%, 65%, 60%, 55% or 50% of the activity of the antibody.

The antibodies useful in the invention must be specific for the S100A4 protein. The term "specific" refers to the capacity of the antibodies for binding specifically to the S100A4 protein and not to other proteins of the S100 family.

To identify the antibodies with the desired specificity, immunochemical assays, such as immunofluorescence, flow cytometry, Western blot and ELISA assays, radioimmunoassays, immunohistochemical assays, immunoprecipitations or other immunochemical assays known in the art, can be used. A number of protocols for competitive binding or immunoradiometric assays are known in the state of the art. Said immunoassays typically involve measuring the formation of a complex between an antibody and an immunogen of the S100A4 protein.

The antibody or fragment thereof according to the first aspect of the invention is selected from the group consisting of:
(i) An antibody that recognizes an epitope of S100A4 comprising the sequence ELPSFLGKRT (SEQ ID NO: 3),
(ii) An antibody that recognizes an epitope of S100A4 comprising the sequence EGFPDKQPRKK (SEQ ID NO: 24) and
(iii) An antibody produced by the hybridoma ECACC 11051804.

The expression "antibody that recognizes an epitope of S100A4" indicates that the antibody is capable of showing specific binding to the epitope without showing substantial binding to other epitopes not comprising this sequence. Suitable means for determining whether an antibody is capable of specifically binding to an epitope is shown in example 14 of the present invention, wherein peptides representing the complete sequence of the target protein are tested against the antibody or fragment thereof. An antibody is considered to bind specifically to a given epitope if it binds to a peptide comprising the sequence of the epitope with substantially higher affinity than to a peptide which does not comprise the sequence of said epitope. The term "substantially higher affinity", as used herein, refers to an affinity level for a particular amino acid sequence which is distinguishable from a level of other amino acid sequence when detected with an intended measurement device or method. Preferably, the affinity of the binding between the antibody and peptide comprising the epitope is at least one order of magnitude higher, at least two orders of magnitude, at least three orders of magnitude higher, at least four orders of magnitude, at least five orders of magnitude higher, at least six orders of magnitude higher than the affinity of the binding between the antibody and a peptide which does not comprising the sequence of the epitope. The association constant (Ka) of binding with substantially high affinity is, for example, at least $10^7 M^{-1}$, preferably at least $10^8 M^{-1}$, and more preferably at least $10^9 M^{-1}$ or lower.

The term "S100A4" is defined in the "Definitions" section. The term also includes all the physiologically relevant post-translational chemical modifications forms, for example, glycosylation, phosphorylation or acetylation, etc., provided that the functionality of the protein is maintained. Said term encompasses the S100A4 of any mammal species, including but not being limited to domestic and farm animals (cows, horses, pigs, sheep, goats, dogs, cats or rodents), primates and humans. Preferably, the S100A4 is human.

The first aspect of the invention contemplates the use of functionally equivalent variants of S100A4. As it is used herein, "functionally equivalent variant of S100A4" is understood as any molecule sharing with S100A4 at least the angiogenic function described in the present invention associated with S100A4, both in vitro and in vivo, and having a minimal identity in the amino acid sequence. The variants of S100A4 can be both natural and artificial.

The expression "natural variant" refers to all those variants of human S100A4 mentioned above which occur naturally in other species, i.e., S100A4 orthologs. Said natural variants include but are not limited to S100A4 of cows, corresponding to the predicted sequence with accession number DAA31755.1 (version of 21 May 2010); S100A4 of rats, corresponding to the predicted sequence with accession number NP_036750.1 (version of 10 Apr. 2011); S100A4 of mouse, corresponding to the predicted sequence with accession number NP_035441.1 (version of 29 May 2011); S100A4 of dogs, corresponding to the predicted sequence with accession number NP_001003161.1 (version of 19 Feb. 2011). The natural variants of S100A4 suitable for use in the first aspect of the present invention can also be derived from said sequences by means of insertion, substitution or deletion of one or more amino acids and include natural alleles, variants resulting from alternative processing and secreted and truncated forms occurring naturally.

The S100A4 useful in the present invention can, therefore, be of a natural sequence when it comprises a polypeptide having the same amino acid sequence as the S100A4 derived from nature. Such polypeptides of a natural sequence can be isolated from nature or they can be produced by recombinant and/or synthetic means. Thus, the S100A4 of the invention can be a recombinant protein obtained by the expression of a polynucleotide encoding S100A4 or a functionally equivalent variant thereof in a heterologous organism, such as a bacterium, yeast or insect or mammal cell. Said recombinant protein can be obtained as a fusion protein with an amino-terminus tail of histidines facilitating the subsequent purification thereof. The expression and purification of said proteins can be performed according to methods known by the person skilled in the art and described in the state of the art.

In a preferred embodiment, the S100A4 is of human origin, preferably of sequence SEQ ID NO: 21. In another preferred embodiment, the S100A4 comes from the expression of a fusion protein comprising the sequence of human S100A4 with an amino-terminus tail of three additional amino acids, the sequence of which is SEQ ID NO: 25.

```
                                                      SEQ ID NO: 25
 1 GSHMACPLEK ALDVMVSTFH KYSGKEGDKF KLNKSELKEL LTRELPSFLG KRTDEAAFQK
61 LMSNLDSNRD NEVDFQEYCV FLSCIAMMCN EFFEGFPDKQ PRKK
```

Alternatively, the S100A4 can be an artificial functionally equivalent variant of S100A4 which can be obtained by recombinant and/or synthetic means.

More information about the term "variant" can be found on the "Definitions" section.

The variants of S100A4 contemplated in the first aspect of the present invention show at least one of the functions of S100A4 such as, without limitation:

The capacity for activating MMP9 matrix metalloproteinase activity, which can be determined by means of the method described in Example 8 of the present invention.

The capacity for inducing the endothelial cell migration, which can be determined by means of the method described in Example 9 of the present invention.

The capacity for inducing tumor development in nude mice, which can be determined by means of the method described in Example 10 of the present application.

The angiogenic capacity or the capacity of forming tumor microvasculature, which can be determined by means of the method described in Example 11 of the present application.

The capacity for inducing an inflammatory response in monocytes mediated by the secretion of IL8, which can be determined by means of the method described in Example 16 of the present application.

Additionally, the functionally equivalent variants of S100A4 contemplated in the first aspect of the invention, include polypeptides showing at least 60%, 65%, 70%, 72%, 74%, 76%, 78%, 80%, 90%, 95%, 97%, 99% similarity or identity with the different natural variants of S100A4 mentioned above. The degree of identity between two polypeptides is determined using algorithms implemented in a computer and methods which are widely known by the persons skilled in the art. The identity between two amino acid sequences is preferably determined using the BLASTP algorithm (BLAST Manual, Altschul, S. et al., NCBI NLM NIH Bethesda, Md. 20894, Altschul, S., et al., J., 1990, Mol. Biol. 215:403-410). The method for calculating the degree of identity is showed on the "Definitions" section.

The "expression substantially preserves the anti-angiogenic activity of said antibody" means that the antibody of the first aspect of the invention cannot lose completely the anti-angiogenic activity.

In general, modifications in the amino acid sequence of the antibody of the invention are also contemplated. For example, it can be desirable to improve the binding affinity and/or other biological properties of the antibody. The variants of the amino acid sequences of the antibody are prepared by introducing the suitable nucleotide changes in the nucleic acid encoding the antibody, or by means of peptide synthesis. Said modifications include, for example, eliminations and/or insertions and/or substitutions of residues in the amino acid sequences of the antibody. Any combination of elimination, insertion and substitution is performed to achieve the final construct, provided that the final construct has the desired characteristics, i.e., S100A4 binding specificity and antagonist anti-angiogenic activity of said protein. The changes in the amino acids can also alter the post-translational processes of the antibody, such as changing the number or the position of the sites of glycosylation.

Some insertions in the amino acid sequence include amino terminus and/or carboxy terminus fusions varying in length from one residue up to polypeptides containing one hundred or more residues, as well as insertions within the sequence of one or several amino acid residues. Some examples of terminal insertions include an antibody with an N-terminus methionyl residue, or the antibody fused to a cytotoxic polypeptide. Other variants by insertion of the antibody molecule include fusion with the N- or C-terminus of the antibody of an enzyme, or a polypeptide increasing the serum half-life of the antibody.

Another type of variant is a variant by amino acid substitution. These variants have at least one amino acid residue of the antibody substituted with a different residue. The sites of major interest for mutagenesis by antibody substitution include the hypervariable regions, but alterations in the FR are also contemplated.

In the context of the present invention, the term "antigen" refers to S100A4.

The specific anti-S100A4 antibody of the first aspect of the invention recognizes an epitope of the antigen S100A4. The inventors have found that the anti-angiogenic antibodies of the invention recognize epitopes contained in the region defined by the sequence ELPSFLGKRT (SEQ ID NO: 3) or by the sequence EGFPDKQPRKK (SEQ ID NO: 24) of S100A4. Thus, in a preferred embodiment the antibody recognizes an epitope of S100A4 comprising the sequence ELPSFLGKRT (SEQ ID NO: 3). In another preferred embodiment the antibody recognizes an epitope of S100A4 comprising the sequence EGFPDKQPRKK (SEQ ID NO: 24).

The expression "recognize an epitope" means that the antibody can bind to an epitope as defined in the "Definitions" section. The epitope can be formed by the entire sequence ELPSFLGKRT (SEQ ID NO: 3) or EGFPDKQPRKK (SEQ ID NO: 24) or by some amino acids of said sequences.

The specific anti-S100A4 antibody of the first aspect of the invention can also be a monoclonal antibody as defined previously and in the "Definitions" section. Thus, in a preferred embodiment, the specific anti-S100A4 antibody of the first aspect of the invention or a fragment thereof is a monoclonal antibody.

The present invention provides monoclonal antibodies produced by different hybridoma cell lines. In a preferred embodiment, the specific anti-S100A4 antibody or fragment thereof according to claim 2 is produced by a hybridoma selected from the group ECACC 10022401, ECACC 11051801, ECACC 11051802, ECACC 11051803 and ECACC 11051804 or a fragment thereof.

In the context of the present invention, "hybrid cell" or "hybridoma" is understood as the product of the fusion of a B-cell clone descendent of a single unique stem cell, and of a myeloma cell. Specifically, the monoclonal antibodies of the first aspect of the invention correspond with the anti-S100A4 monoclonal antibodies referred to in the experimental part of the present document as 5C3, 6B9, 5A3, 1E2 and 8B6, which have been obtained from the hybridomas generated by the inventors and identified as 5C3-1B8-1F4, 6B9-1E8-2A8, 5A3-4A6-5B6, 1E2-2H4-2G8 and 8B6-2F6-1H9-1H10, respectively. Said hybridomas have been deposited prior to filing the present patent application in the European Collection of Cell Cultures (ECACC), Porton Down, Salisbury, SP4 OJG, United Kingdom, as a legally recognized institution for that purpose in accordance with the Budapest Treaty, of 28 Apr. 1977, on the International Recognition of the Deposit of Microorganisms.

The depositors have been Francesc Mitjans and Marc Masa from Leitat Technological Center with address Baldiri Reixach 15-21 Helix Building, Barcelona, 08028, Spain.

The European Collection of Cell Cultures (ECACC) has assigned to hybridomas 5C3-1B8-1F4, 6B9-1E8-2A8, 5A3-4A6-5B6, 1E2-2H4-2G8 and 8B6-2F6-1H9-1H10 the respective deposit numbers ECACC 10022401, ECACC 11051801, ECACC 11051802, ECACC 11051803 and ECACC 11051804. The culture conditions of said hybridoma lines which allow obtaining the anti-S100A4 monoclonal antibodies of the invention are described in the context of the method for obtaining the monoclonal antibodies of the invention.

In the present document, hybridomas 5C3-1B8-1F4, 6B9-1E8-2A8, 5A3-4A6-5B6, 1E2-2H4-2G8 and 8B6-2F6-1H9-1H10 and the antibodies produced by said hybridomas are indicated by means of their abbreviated name 5C3, 6B9, 5A3, 1E2 and 8B6, respectively.

The invention also contemplates fragments of said specific anti-S100A4 monoclonal antibodies of the first aspect of the invention which maintain the capacity for binding to S100A4 and also the anti-angiogenic capacity. The capacity for binding can be checked by means of methods known by the person skilled in the art, such as ELISA or Western blot, as described in Examples 5, 6 and 7 of the present invention. The capacity for maintaining the anti-angiogenic capacity can be checked by means of methods known by the person skilled in the art, such as those described in Example 9 of the present invention.

Said "fragment" refers to a fragment of the antibody sequence that corresponds to one or several portions of the amino acid sequence of the mentioned monoclonal antibody which maintains the capacity for binding to S100A4, and therefore, the polypeptide must include the sequence of the 6 CDR regions, which can be used for obtaining the antibodies defined in the context of the first aspect of the invention, such as, without limitation, genetically engineered antibodies such as chimeric antibodies, humanized antibodies or bispecific antibodies. Said "fragment" can also be used for obtaining antibody fragments such as Fab, F(ab')2, Fab', single chain Fv fragments (scFv), diabodies or nanobodies. Additionally, the fragment maintains the capacity of blocking angiogenesis.

The Fab and F(ab')2 fragments can be obtained by means of enzymatic or chemical cleavage of the intact monoclonal antibodies of the first aspect of the invention.

Papain digestion of a monoclonal antibody of the invention produces two identical antigen binding fragments referred to as "Fab" fragments, each with a single antigen binding site. In turn, the "F(ab')2" fragment, which has two antigen binding sites, is obtained by pepsin treatment.

Additionally, the "fragment" allows obtaining another type of antibody fragments such as Fab' fragments, single chain Fv fragments (scFv) or diabodies by means of genetic engineering techniques.

In a preferred embodiment the specific anti-S100A4 antibody or fragment thereof is produced by the hybridoma ECACC 10022401.

The present invention provides an isolated amino acid sequence comprising SEQ ID NO: 1. This amino acid sequence encompasses the FRs and CDRs of the light chain of the variable region of a monoclonal antibody directed against S100A4. In particular, the sequences of the light chain of the variable region as well as the respective FRs and CDRs are as follows:

| SEQ ID NO. | region | Sequence |
|---|---|---|
| 1 | VL | DVLMTQTPLSLPVSLGDQASISCRSSQSIVHSNGNTYL EWYLQKTGQSPELLIYKVSNRLSGVPDRFSGSGSGTDF TLKISRVEAEDLGVYYCFQGSHVPFTFGSGTKLEIK |
| 7 | FRL1 | DVLMTQTPLSLPVSLGDQASISC |
| 8 | CDRL1 | RSSQSIVHSNGNTYLE |
| 9 | FRL2 | WYLQKTGQSPELLIY |
| 10 | CDRL2 | KVSNRLS |
| 11 | FRL3 | GVPDRFSGSGSGTDFTLKISRVEAEDLGVYYC |
| 12 | CDRL3 | FQGSHVPFT |
| 13 | FRL4 | FGSGTKLEIK |

The present invention provides an isolated amino acid sequence comprising SEQ ID NO: 2. This amino acid sequence encompasses the FRs and CDRs of the heavy chain of the variable region of a monoclonal antibody directed against human or murine S100A4. In particular, the sequences of the heavy chain of the variable region as well as the respective FRs and CDRs are as follows:

| SEQ ID NO. | region | Sequence |
|---|---|---|
| 2 | VH | EAQLQQSGAELVKPGASVKLSCTASGFNIQETYMHWVKQ RPEQGLEWIGRIDPANGNTKDDPKFQGKASITVDTSSNT AYLQLSSLTSEDTAVYYCASSYAMDYWGQGTSVTVSS |
| 14 | FRH1 | EAQLQQSGAELVKPGASVKLSCTASGFNIQ |
| 15 | CDRH1 | ETYMH |
| 16 | FRH2 | WVKQRPEQGLEWIG |
| 17 | CDRH2 | RIDPANGNTKDDPKFQG |
| 18 | FRH3 | KASITVDTSSNTAYLQLSSLTSEDTAVYYCAS |
| 19 | CDRH3 | SYAMDY |
| 20 | FRH4 | WGQGTSVTVSS |

Said sequences correspond to the antibody produced by the hybridoma ECACC 10022401. Thus, in a preferred embodiment the antibody or fragment thereof comprises at least a VL region comprising the sequence SEQ ID NO: 1 and at least a VH region comprising the sequence SEQ ID NO: 2 or a functionally equivalent variant thereof that maintains substantially the anti-angiogenic activity.

The term "VL region" refers to the variable region of the light chain of the antibody; whereas the term "VH region" refers to the variable region of the heavy chain of the antibody.

The expression "functionally equivalent variant thereof that maintains substantially the anti-angiogenic activity" refers to any molecule sharing with the antibody of the invention the anti-angiogenic function, both in vitro and in vivo, and having a minimal identity with the amino acid sequence. The functionally equivalent variants of the antibodies of the invention can be derived from said sequences by means of insertion, substitution or deletion of one or more amino acids and can be obtained by recombinant and/or synthetic means.

The functionally equivalent variants of the antibodies of the invention must conserve their capacity for binding to the S100A4 antigen and also the capacity for inhibiting the angiogenic function of the S100A4 protein, Said function can be checked by means of the methods known by the skilled in the art, for example by means of the endothelial migration assay with VEGF and S100A4 as described in Example 9 of the present application.

The functionally equivalent variants of the antibodies of the invention include polypeptides showing at least 60%, 65%, 70%, 72%, 74%, 76%, 78%, 80%, 90%, 95%, 97%, 99% identity with the polypeptide sequences mentioned before; preferably having at least 90% identity. The degree of identity between two polypeptides is determined using algorithms implemented in a computer and methods which are widely known by the persons skilled in the art. The identity between two amino acid sequences is preferably determined using the BLASTP algorithm (BLAST Manual, Altschul, S. et al., NCBI NLM NIH Bethesda, Md. 20894, Altschul, S., et al., J., 1990, Mol. Biol. 215:403-410). The degree of identity is calculated according to the method described in the "Definitions" section.

The present invention provides an isolated amino acid sequence comprising SEQ ID NO: 3. This amino acid corresponds to the epitope or antigenic determinant of a human or murine S100A4.

SEQ ID NO: 3
ELPSFLGKRT

In one embodiment of the present invention there is provided an antibody or fragment thereof that specifically binds to a polypeptide comprising SEQ ID NO: 3.

In one embodiment of the present invention there is provided an antibody or fragment thereof that specifically binds a human or murine S100A4 polypeptide produced by immunizing a mammal with a polypeptide comprising SEQ ID NO:3.

In one embodiment of the present invention, the antibody or fragment thereof is selected from a human antibody or a fragment thereof; a humanized antibody or a fragment thereof a polyclonal antibody or a fragment thereof a monoclonal antibody or a fragment thereof a Fab antibody; and a chimeric antibody or a fragment thereof.

In one embodiment of the present invention there is provided a monoclonal antibody comprising a light chain polypeptide comprising SEQ ID NO: 1.

In one embodiment of the present invention there is provided a monoclonal antibody comprising a heavy chain polypeptide comprising SEQ ID NO: 2.

In one embodiment of the present invention there is provided a monoclonal antibody comprising framework regions (FRs) and complementarity determining regions (CDRs), wherein the monoclonal antibody comprises a light chain comprising SEQ ID NO: 1 and a heavy chain comprising SEQ ID NO: 2.

In one embodiment of the present invention, the monoclonal antibody is selected from a human antibody; a humanized antibody; and a chimeric antibody or a fragment thereof.

In one embodiment of the present invention, the monoclonal antibody:
a) reacts only with a human or murine S100A4 protein; or
b) blocks a mechanism of action of a human or murine S100A4 protein; or
c) blocks in vitro or in vivo functional activity of a human or murine S100A4 protein; or
d) blocks a promigratory effect induced by a human or murine S100A4 protein or by a human or murine S100A4 protein combined with VEGF in endothelial cells; or
e) blocks tumor growth; or
f) blocks tumor development; or
g) blocks tumor angiogenesis; or
h) blocks cellular dissemination and metastatic establishment; or
i) blocks inflammatory processes; or
j) blocks cancer stem cells; or
k) any combination of a) to j) above.

In one embodiment of the present invention there is provided a monoclonal antibody or fragment thereof comprising SEQ ID NO: 1 and SEQ ID NO: 2, wherein said antibody or fragment is monovalent or bivalent. The present invention further provides a hybridoma cell line capable of producing the monoclonal antibody according to any one of the embodiments presented herein.

The present invention further provides a monoclonal antibody obtainable by a hybridoma cell line deposited under accession number 10022401 at the European Collection of Cell Cultures (ECACC).

In one embodiment of the present invention there is provided an isolated polynucleotide comprising SEQ ID NO: 4 coding for the FRs and CDRs of the light chain of the variable region of a monoclonal antibody.

```
                                                    SEQ ID NO: 4
  1 GATGTTTTGA TGACCCAAAC TCCACTCTCC CTGCCTGTCA GTCTTGGAGA TCAAGCCTCC

61 ATCTCTTGCA GATCTAGTCA GAGTATTGTA CATAGTAATG GAAACACCTA TTTAGAATGG

121 TACCTGCAGA AAACAGGCCA GTCTCCAGAG CTCCTGATCT ACAAAGTTTC CAACCGACTC

181 TCTGGGGTCC CAGACAGGTT CAGTGGCAGT GGATCAGGGA CAGATTTCAC ACTCAAGATC

241 AGCAGAGTGG AGGCTGAGGA TCTGGGAGTT TATTACTGCT TTCAAGGTTC ACATGTTCCA

301 TTCACGTTCG GCTCGGGGAC AAAGTTGGAA ATAAAA
```

In one embodiment of the present invention there is provided an isolated polynucleotide comprising SEQ ID NO: 5 coding for the FRs and CDRs of the heavy chain of the variable region of a monoclonal antibody.

In one embodiment of the present invention there is provided an isolated polynucleotide comprising SEQ ID NO: 6 coding for an epitope region of the human S100A4 protein.

```
                   SEQ ID NO: 6
GAGCTGCCCAGCTTCTTGGGGAAAAGGACA
```

In another preferred embodiment the specific anti-S100A4 antibody of the invention or fragment thereof is produced by the hybridoma ECACC 11051801.

In another preferred embodiment the specific anti-S100A4 antibody of the invention or fragment thereof is produced by the hybridoma ECACC 11051802.

In another preferred embodiment the specific anti-S100A4 antibody of the invention or fragment thereof is produced by the hybridoma ECACC 11051803.

In another preferred embodiment the specific anti-S100A4 antibody of the invention or fragment thereof is an antibody produced by the hybridoma ECACC 11051804.

The monoclonal antibodies of the first aspect of the invention have demonstrated that they are capable of stopping the migration capacity of human endothelial cells. Therefore, in a particular embodiment, the invention relates to a specific anti-S100A4 antibody having anti-angiogenic activity or a fragment thereof which substantially preserves the anti-angiogenic activity of said antibody which is capable of stopping the migration capacity of human endothelial cells.

"Stopping the migration capacity of human endothelial cells" is understood as the inhibition of the migration capacity of said cells by at least 20%, 25%, 30%, 35%, 40%, 45%, 50%, 60%, 70%, 75%, 80%, 85%, 90%, 95%, 99%, 100%; preferably at least 20%; more preferably at least 30%; still more preferably at least 45%. Said inhibition of the migration capacity or stop of the migration can be evaluated by means of the assays described in Example 9 of the present invention.

The expression "migration capacity of human endothelial cells" refers to the capacity of said cells of moving which is a key step in neovasculature formation. Human endothelial cells are cells lining all the vessels of a mammalian organism.

```
                                                    SEQ ID NO: 5
  1 GAGGCTCAGC TGCAGCAGTC TGGGGCAGAG CTTGTGAAGC CAGGGGCCTC TGTCAAGTTG

61 TCCTGCACAG CCTCTGGCTT CAACATTCAA GAGACCTATA TGCACTGGGT GAAGCAGAGG

121 CCTGAACAGG GCCTGGAGTG GATTGGAAGG ATTGATCCTG CGAATGGTAA TACCAAAGAT

181 GACCCGAAGT TCCAGGGCAA GGCCTCTATA ACAGTAGACA CATCCTCCAA CACAGCCTAC

241 CTGCAGCTCA GCAGCCTGAC ATCTGAGGAC ACTGCCGTCT ATTACTGTGC TTCAAGTTAT

301 GCTATGGACT ACTGGGGTCA AGGAACCTCA GTCACCGTCT CCTCA
```

Human endothelial cells included in said definition are, without limitation, human umbilical vein endothelial cells (HUVECs). In a preferred embodiment the human endothelial cells are HUVECs cells.

Hybridoma Cell Lines and Method for Obtaining the Monoclonal Antibodies of the Invention In another aspect, the invention relates to a method for obtaining a monoclonal antibody according to the first aspect of the invention which comprises culturing a hybridoma cell line selected from those cell lines deposited with accession number ECACC 10022401, ECACC 11051801, ECACC 11051802, ECACC 11051803 and ECACC 11051804 in conditions which allow the production of said antibody.

The method for obtaining the monoclonal antibodies of the first aspect of the invention can be performed according to conventional methods known in the state of the art. Basically, the method consists of culturing the hybridoma cell line in a culture medium suitable for the hybridoma cells to produce antibodies and to secrete them into the medium, and of subsequently collecting the supernatant of the culture medium containing the monoclonal antibodies produced. Said antibodies can optionally be purified by conventional means, such as affinity chromatography, protein A sepharose, hydroxyapatite chromatography, gel electrophoresis or dialysis.

The term "monoclonal antibody" has already been defined in the previous aspect.

"Culturing" a hybridoma cell line is understood as incubating the hybridoma cells in the presence of a suitable medium in culture vials for the necessary time and in the suitable conditions for the multiplication of said cells and the production of the monoclonal antibodies of the invention to occur. Said culture can involve the use of culture media with different compositions. Preferably, in a first step the cells are cultured in a medium containing serum to favor their multiplication and, after collecting the cells and washing them, they are cultured in a serum-free medium to obtain antibodies. Culture media suitable for obtaining the antibodies according to this method are, without limitation, DMEM/F12 supplemented with L-Glutamine and Fetal Calf Serum to favor cell multiplication and a mixture based on the DMEM/F12 medium supplemented with L-glutamine but lacking Fetal Calf Serum ("protein free medium") as an antibody collection medium. The medium for producing antibodies could also consist of any medium or mixture of synthetic cell culture mediums the composition and subsequent supplementation of which does not include proteins ("protein free medium") or said proteins are in a very low proportion ("serum free medium" or "low protein medium") and they do not belong to the group of immunoglobulins. Said medium must allow the cell growth and maintenance as well as the secretion of antibodies by the hybridoma cell line previously adapted to grow in the absence of Fetal Calf Serum. In a preferred embodiment the medium suitable for the culture of said cells is a medium comprising DMEM/F12 and L-glutamine. The conditions in which said culture are performed are preferably in a humid environment and at a temperature of 37° C. with standard air atmosphere or 5% CO2 enriched air.

Therefore, in another aspect the invention relates to a hybridoma cell line selected from the group consisting of a cell line deposited with accession number ECACC 10022401, ECACC 11051801, ECACC 11051802, ECACC 11051803 and ECACC 11051804. Preferably the cell line has the accession number ECACC 10022401. In another embodiment the hybridoma cell line is selected from the group consisting of a cell line deposited with accession number ECACC 11051801, ECACC 11051802, ECACC 11051803 and ECACC 11051804.

The expression "hybridoma cell line" refers to a cell line formed by hybrid cells or hybridomas as previously defined in the first aspect of the invention. Said hybridoma cell line has been obtained by standard methodologies as described in Example 4 of the present invention. Briefly, mice were immunized with a human recombinant S100A4 protein and cells were extracted from the spleen of the immunized mouse which were fused with myeloma cells in the presence of a fusion inducer such as PEG-1500. The hybridomas were selected in HAT medium and each selected clone was subcloned by limiting dilution. The clones suitable for expansion were adapted to the DMEM/F12 medium and were frozen, constituting the hybridoma cell lines ECACC 10022401, ECACC 11051801, ECACC 11051802, ECACC 11051803 and ECACC 11051804.

In preferred embodiments of the invention, the monoclonal antibody prepared by means of this method can be any of those produced by the hybridoma cell lines described in the context of the present invention.

The present invention further provides a method for the manufacture of a monoclonal antibody according to any one of the embodiments presented herein, said method comprising:

(i) immunizing a mouse with purified human or murine S100A4 protein or with purified human or murine S100A4 protein combined with an agent effective to induce an immune response against an antigen;
(ii) producing one or more hybridoma cells,
(iii) selecting one or more cells the supernatants of which:
  a) react only with a human or murine S100A4 protein; or
  b) block a mechanism of action of a human or murine S100A4 protein; or
  c) block in vitro or in vivo functional activity of a human or murine S100A4 protein; or
  d) block a promigratory effect induced by a human or murine S100A4 protein or by a human or murine S100A4 protein combined with VEGF in endothelial cells; or
  e) block tumor growth; or
  f) block tumor development; or
  g) block tumor angiogenesis; or
  h) block cellular dissemination and metastatic establishment; or
  i) block inflammatory processes; or
  j) block cancer stem cells; or
  k) any combination of a) to j) above.
(iv) producing a specific cell line from any one of the selected cells of step iii); and
(v) isolating the monoclonal antibody from said cell line.

Pharmaceutical Compositions Comprising Specific Anti-S100A4 Antibodies of the Invention In another aspect, the invention relates to a pharmaceutical composition comprising a pharmaceutically effective amount of at least one antibody according to the first aspect of the invention or a fragment thereof and at least one pharmaceutically acceptable excipient.

In a preferred embodiment the antibody according to the first aspect of the invention is produced by a hybridoma selected from the group ECACC 10022401, ECACC 11051801, ECACC11051802, ECACC 11051803 and ECACC 11051804 or a fragment thereof; preferably ECACC 10022401.

As it is used in the present invention, the expression "pharmaceutical composition" relates to a formulation that has been adapted for administering a predetermined dose of one or several therapeutic useful agents to a cell, a group of cells, an organ, a tissue or an animal in which there is an overexpression of the S100A4 protein.

"Pharmaceutically effective amount" is understood as an amount capable of providing a therapeutic effect, and which can be determined by the person skilled in the art by commonly used means.

The compositions of the invention can contain one or more antibodies according to the first aspect of the invention or one or more fragments thereof which substantially preserve the anti-angiogenic activity of said antibody.

The compositions of the invention can also contain one or several additional compounds for the prevention and/or treatment of pathologies in which there is an overexpression of the S100A4 protein, such as cancer or diseases associated with inflammation. Said additional compounds such as cytotoxic agents, antiangiogenic agents, antimetastatic agents or anti-inflammatory agents can form part of the pharmaceutical composition as independent entities of the monoclonal antibodies or also forming conjugates with said antibodies.

The pharmaceutical compositions are prepared by conventional means with one or more pharmaceutically acceptable excipients.

"Pharmaceutically acceptable excipient" is understood a therapeutically inactive substance said to be used for incorporating the active ingredient and which is acceptable for the patient from a pharmacological/toxicological point of view and for the pharmaceutical chemist who manufactures it from a physical/chemical point of view with respect to the composition, formulation, stability, acceptation of the patient and bioavailability.

The number and the nature of the pharmaceutically acceptable excipients depend on the desired dosage form. The pharmaceutically acceptable excipients are known by the person skilled in the art (Fauli y Trillo C. (1993) "Tratado de Farmacia Galénica", Luzán 5, S. A. Ediciones, Madrid). Said compositions can be prepared by means of the conventional methods known in the state of the art ("Remington: The Science and Practice of Pharmacy", 20th edition (2003) Genaro A. R., ed., Lippincott Williams & Wilkins, Philadelphia, US).

The pharmaceutical compositions of the invention can be administered by any type of suitable route, such as by oral route, topical route, by inhalation or parenteral route so that the pharmaceutically acceptable excipients necessary for the formulation of the desired dosage form will be included. The preferred route of administration of the pharmaceutical composition is the endovenous route.

"Oral route" is understood as the pharmaceutical composition incorporated into the organism after deglutition. In a particular embodiment, the pharmaceutical composition of the invention can be in a dosage form suitable for its administration by oral route, whether it is solid or liquid. The dosage forms suitable for their administration by oral route can be tablets, capsules, syrups or solutions, and can contain any conventional excipient known in the art, such as binders, for example syrup, acacia, gelatin, sorbitol or polyvinylpyrrolidone; filling agents, for example lactose, sugar, corn starch, calcium phosphate, sorbitol or glycine; lubricants for compression, for example magnesium stearate; disintegrating agents, for example starch, polyvinylpyrrolidone, sodium glycolate of starch or microcrystalline cellulose; or pharmaceutically acceptable wetting agents such as sodium lauryl sulfate. The solid oral compositions can be prepared by means of conventional processes of mixing, filling or compressing. Repetitive mixing operations can be used to completely distribute the active agent in those compositions that use high amounts of filling agents. Said operations are conventional in the art. The tablets can be prepared, for example, by means of wet or dry granulation, and optionally coating them according to the processes known in the common pharmaceutical practice, particularly with an enteric coating.

On the other hand, "topical route" is understood as an administration by non-systemic route, and includes the application of a pharmaceutical composition of the invention externally on the epidermis, in the oral cavity and the instillation of said composition into ears, eyes and nose, and in which it does not significantly enter the blood stream. "Systemic route" is understood as the administration by oral route, intravenous route, intraperitoneal route and intramuscular route. The amount of antibody required for the therapeutic or prophylactic effect will naturally vary according to the elected antibody, the nature and the severity of the illness that is going to be treated, and the patient.

"Inhalation" is understood as the administration by intranasal route and by oral inhalation. The dosage forms suitable for said administration, such as a formulation in aerosol or a meter dosed inhaler can be prepared by means of conventional techniques.

As it is used herein, the term "parenteral", includes administration by intravenous route, intraperitoneal route, intramuscular route or subcutaneous route. Subcutaneous, intramuscular and intravenous dosage forms of parenteral administration are generally preferred.

In one embodiment, the pharmaceutical compositions of the invention can be adapted for their parenteral administration, such as sterile solutions, suspensions or lyophilized products in the appropriate dosage unit form. The pharmaceutical compositions suitable for its injectable use include sterile aqueous solutions (when they are soluble in water), or dispersions and sterile powders for the extemporaneous preparation of sterile injectable solutions or dispersions. For its administration by intravenous route, some suitable carriers include saline solution buffered with phosphate (PBS). In all the cases, the composition must be sterile, and must be fluid to the point of which there exists easy ability to inject. It must be stable in the preparation and storage conditions, and must be protected from the contamination action of microorganisms such as bacteria and fungi. The carrier can be a solvent or a dispersion medium which contains, for example, water, ethanol, a pharmaceutically acceptable polyol such as glycerol, propylene glycol, liquid polyethylene glycol and suitable mixtures thereof. Suitable fluidity can be maintained, for example, by means of using a coating such as lecithin, by means of maintaining the particle size required in the case of a dispersion and by means of using surfactants. The prevention of the action of the microorganisms can be achieved by means of various antibacterial and antifungal agents, for example, parabens, chlorobutanol, phenol, ascorbic acid, thiomersal, and the like. In most cases, it will be preferable to include isotonic agents, for example, sugars; polyalcohols such as mannitol, sorbitol; or sodium chloride in the composition. The prolonged absorption of the injectable compositions may be caused by the inclusion of an agent which delays the absorption, for example, aluminum and gelatin monostearate.

The injectable sterile solutions can be prepared by incorporating the active compound in the required amount in a suitable solvent with one or a combination of the aforementioned ingredients, as needed, followed by sterilization by filtration through sterile membranes. Generally, the dispersions are prepared by incorporating the active compound in a sterile vehicle containing a basic dispersion medium and the rest of the ingredients required from among those previously listed. In the case of sterile powders for the preparation of injectable sterile solutions, the preferred preparation processes are vacuum drying and lyophilization which give rise to a powder with the active ingredient plus any desired additional ingredient from a previously filtered sterile solution thereof. The antibody will usually be stored in lyophilized form or in solution. The compositions of therapeutic antibody are generally housed in a packaging which has a sterile access opening, for example, an intravenous solution bag or vial having an adaptor which allows recovering the formulation, such as a stopper that can be perforated by a hypodermic injection needle.

The pharmaceutical composition can be suitably administered by means of pulse infusion, for example, with decreasing doses of the antibody. Preferably, the dose is administered by means of injections, more preferably intravenous or subcutaneous injections, partly depending if the administration is acute or chronic.

In one embodiment, the pharmaceutical composition which contains the antibody of the first aspect of the invention is prepared with carriers which will protect said antibody from a rapid elimination from the body, such as a controlled release formulation, including implants and microencapsulated administration systems. Biodegradable biocompatible polymers such as ethylene vinylacetate, polyanhydrides, polyglycolic acid, collagen, polyorthoesters and polylactic acid can be used. The processes for preparing said formulations will be clear for persons skilled in the art. The materials can also be commercially obtained in Alza Corporation and Nova Pharmaceuticals, Inc.

The sustained release compositions also include preparations of antibody crystals suspended in suitable formulations which can maintain the crystals in suspension. These preparations, when they are injected by subcutaneous or intraperitoneal route may produce a sustained release effect. Other compositions also include antibodies trapped in liposomes. The liposomes containing such antibodies are prepared by means of known methods such as Epstein et al., Proc. Natl. Acad. Sci. USA, (1985) 82:3688-3692; Hwang et al., Proc. Natl. Acad. Sci. USA, (1980) 77:4030-4034; EP 52,322; EP 36,676; EP 88,046; EP 143,949.

The compositions of the invention are suitable for the administration into any type of mammal, preferably a human being.

The present invention further provides a pharmaceutical composition comprising a monoclonal antibody according to any one of the embodiments presented herein, and a pharmaceutically acceptable carrier.

In one embodiment of the present invention, the pharmaceutical composition further comprises a chemotherapeutic agent.

In another embodiment of the present invention, the pharmaceutical composition further comprises an anti-inflammatory agent.

Pharmaceutical Compositions Comprising Specific Anti-S100A4 Antibodies and Antimetabolites The authors have surprisingly found that the combination of specific antibodies anti-S100A4 with an antimetabolite drug have a synergistic effect as a cytotoxic in the treatment of cancer (see example 15 of the present invention).

Thus, an aspect of the present invention is a pharmaceutical composition comprising a specific anti-S100A4 antibody and an antimetabolite.

As it is used in the present invention, the expression "pharmaceutical composition" relates to a formulation that has been adapted for administering a predetermined dose of one or several therapeutic useful agents to a cell, a group of cells, an organ, a tissue or an animal suffering from cancer.

The term "specific anti-S100A4 antibody", in the context of this aspect of the invention, refers to any antibody that recognizes specifically the S100A4 protein, including antibodies previously disclosed in the prior art.

"Antimetabolite", as used herein, relates, in a bro'd sense, to substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides).

Antimetabolites suitable for use in the present invention include, without limitation, folic acid antimetabolites (aminopterin, denopterin, methotrexate, edatrexate, trimetrexate, nolatrexed, lometrexol, pemetrexed, raltitrexed, piritrexim, pteropterin, leucovorin, 10-propargyl-5,8-dideazafolate (PDDF, CB3717)), purine analogs (cladribine, clofarabine, fludarabine, mercaptopurine, pentostatin, thioguanine) and pyrimidine analogs (capecitabine, cytarabine or ara-C, decitabine, fluorouracil, 5-fluorouracil, doxifluridine, floxuridine and gemcitabine). In a preferred embodiment the antimetabolite is selected from 5-fluorouracil and gemcitabine, more preferably gemcitabine. When the subject suffers from colon cancer the first line chemotherapeutic treatment are antimetabolites, preferably 5-fluorouracil. When the subject suffers from pancreatic cancer, bladder cancer or gallbladder cancer the first line chemotherapeutic treatment are antimetabolites, preferably gemcitabine.

In a preferred embodiment the antibody is a specific anti-S100A4 antibody having anti-angiogenic activity or a fragment thereof which substantially preserves the anti-angiogenic activity of said antibody wherein the antibody is selected from the group consisting of:
  (i) An antibody that recognizes an epitope of S100A4 comprising the sequence ELPSFLGKRT (SEQ ID NO: 3),
  (ii) An antibody that recognizes an epitope of S100A4 comprising the sequence EGFPDKQPRKK (SEQ ID NO: 24) and
  (iii) An antibody produced by the hybridoma ECACC 11051804.

In a preferred embodiment the antibody according to this aspect is a monoclonal antibody, preferably is a monoclonal antibody produced by a hybridoma selected from the group ECACC 10022401, ECACC 11051801, ECACC11051802, ECACC 11051803 and ECACC 11051804 or a fragment thereof; more preferably ECACC 10022401.

The authors have demonstrated that a combination of an anti-S100A4 antibody and an antimetabolite is capable of reducing the viability of tumor cells. Thus, in a preferred embodiment the composition is capable of reducing the viability of tumor cells.

"Reducing the viability of tumor cells" is understood as the reduction of the capacity of the cells to survive, grow and multiply by at least 30%, 40%, 50%, 60%, 65%, 70%, 75%, 80%, 85%, 90%, 95%, 99%, 100%; preferably at least 60%; still more preferably at least 65%; most preferably at least 70%. Said reduction of the viability can be evaluated by means of the assay described in Example 15 of the present invention.

"Tumor cell" is understood as a malignant cell, also known as a cancerous or carcinogenic cell which grows and divides beyond the normal limits, invading the surrounding tissue and sometimes causing metastasis. The tumor cells that can be treated with the antibodies of the present invention are cells which overexpress the S100A4 protein. Said cells include tumor cells from known and established cell lines and tumor cells present in the organism of a patient suffering from cancer. Several illustrative non-limiting examples of tumor lines which overexpress S100A4 are the Colo 205 colon adenocarcinoma tumor line, the MiaPACA-2 human pancreatic adenocarcinoma cell line, Panc1 human pancreatic carcinoma cell line, HCT116 colon adenocarcinoma cell line, cancer stem cells derived from a culture of MDA-MB-231 mammary adenocarcinoma cell line. Illustrative non-limiting examples of tumor cells present in a patient suffering from cancer and which overexpress S100A4 are tumor cells from breast carcinoma (Rudland P S et al. Cancer Res 2000. 60(6): 1595-1603), prostate carcinoma (Saleem M et al. PNAS 2006. 103(40): 14825-30), lung carcinoma (Tsuna M et al. Anticancer Res 2009. 29(7): 2547-54), colorectal carcinoma (Cho Y et al. World J Gastroent 2005. 11(31): 4852-6), pancreatic carcinoma (Rosty C et al. Am J Pathol 2002. 160(1): 45-50), renal carcinoma (Bandiera A et al. World J Surg 2009. 33(7): 1414-20), gastric carcinoma (Yonemura Y et al. Clin Cancer Res 2000. 6(11): 4234-42), ovarian carcinoma (Maelandsmo G M et al. Tumor Biol 2009. 30(1):15-25), papillary thyroid carcinoma (Min H S et al. Mod Pathol 2008. 21(6): 748-55), melanoma (Andersen K et al. Mod Pathol 2004. 17(8): 990-997), hepatocellular carcinoma (Cui J et al. J Can Res Clin Oncol 2004. 130(10): 615-22), bladder carcinoma (Agerbaek M et al. Eur Urol 2006. 50(4): 777-785), liposarcoma invasive carcinoma (Pazzaglia L et al. Anticancer Res 2004. 24(2B): 967-972), neuroblastoma (Bjornland K et al. J Pediatr Surg 2001. 36(7): 1040-44), esophageal squamous carcinoma (Ninomiya I et al. Int J Oncol 2001. 18(4): 715-20), osteosarcoma (Mathisen B et al. Clin Exp Metastasis 2003. 20(8): 701-11), gallbladder carcinoma (Nakamura T et al. Int J Oncol 2002. 20(5): 937-41), oral squamous carcinoma (Moriyama-Kita M et al. Oral Oncol 2004. 40(5): 496-500), endometrial carcinoma (Xie R et al. Lab Invest 2009. 89(8): 937-947), and medulloblastoma (Hernan R et al. Cancer Res 2003. 63(1): 140-148), amongst others.

The tumor cells which express the S100A4 protein can be identified by means of conventional methods such as ELISA or Western blot, according to the method described in the present invention.

In one embodiment, the tumor cells the viability of which is reduced by means of the antibodies of said aspect of the invention are tumor cells from pancreatic cancer or from colon cancer, preferably from pancreatic cancer.

In another aspect, the invention relates to a pharmaceutical composition comprising a specific anti-S100A4 antibody and a metabolite for use in the prevention and/or the treatment of cancer or metastasis.

In another aspect, the invention relates to the use of a pharmaceutical composition comprising a specific anti-S100A4 antibody and a metabolite for the preparation of a medicament for the prevention and/or the treatment of cancer or metastasis.

In another aspect, the invention relates to a method of treatment or prevention of cancer or metastasis in a subject which comprises the administration to said subject of a pharmaceutical composition comprising a specific anti-S 100A4 antibody and a metabolite.

The terms "prevention", "treatment", "cancer" and "metastasis" will be defined in the context of the therapeutic uses of the antibodies of the invention.

All the particular embodiments of the previous aspects are applicable to said aspects.

Therapeutic Uses of the Antibodies of the Invention
Angiogenesis and Cancer

The present invention further provides an antibody or fragment thereof or a monoclonal antibody according to any one of the embodiments presented herein, for use as a medicament.

The present invention also provides an antibody or fragment thereof or a monoclonal antibody according to any one of the embodiments presented herein, for use as a medicament for the treatment of tumors.

The present invention also provides the use of an antibody or fragment thereof or a monoclonal antibody according to any one of the embodiments presented herein, for the manufacture of a medicament for the treatment of tumors.

The present invention also provides a method for treating tumors comprising administering to a subject in need of said treatment a pharmaceutically effective amount of the antibody or fragment thereof or monoclonal antibody according to any one of the embodiments presented herein.

The anti-S 100A4 antibodies capable of binding specifically to the S100A4 protein have an application in those diseases in which said protein is overexpressed.

Specifically, the S100A4 protein is expressed, as has been described above, in a wide variety of cancers.

As a result, the S100A4 protein ligands, and more specifically, antibodies specific against this protein, are candidate drugs to be used in therapy for the treatment of said disease.

Thus, in one aspect the invention relates to an antibody or fragment thereof according to the first aspect of the invention for use in the prevention and/or treatment of a disease selected from metastasis and a disease associated to an undesired angiogenesis.

In another aspect, the invention relates to the use of an antibody or fragment thereof according to the first aspect of the invention for the preparation of a medicament for the prevention and/or treatment of a disease selected from metastasis and a disease associated to an undesired angiogenesis.

In another aspect, the invention relates to a method of treatment or prevention of a disease selected from metastasis and a disease associated to an undesired angiogenesis in a subject which comprises the administration to said subject of an antibody or fragment thereof according to the first aspect of the invention.

The terms "antibody" and "fragment" have been previously defined in the context of the first aspect of the invention.

"Prevention" is understood as the administration of an antibody or a fragment thereof according to the first aspect of the invention, or of a medicament containing it in an initial or early stage of the disease, or to also prevent its onset.

The term "treatment" is used to designate the administration of an antibody or a fragment thereof according to the first aspect of the invention or of a medicament containing it to control the progression of the disease before or after the clinical signs have appeared. Control of the progression of the disease is understood as the beneficial or desired clinical results which include but are not limited to reduction of the symptoms, reduction of the duration of the disease, stabilization of pathological conditions (specifically avoiding additional impairment), delaying the progression of the disease, improving the pathological condition and remission (both partial and complete). The control of the progression of the disease also involves a prolongation of survival in comparison to the expected survival if the treatment was not applied.

"Medicament" is understood as a pharmaceutical composition comprising an antibody or a fragment thereof according to the first aspect of the invention.

The term "metastasis" is understood as the distance propagation, fundamentally by the lymphatic or blood stream, of the cancer causing cells, and the growth of new tumors in the destination sites of said metastasis.

In the context of the present invention, "angiogenesis" is understood to mean the physiological process that consists of the formation of new blood vessels from existing blood vessels. Angiogenesis is also known as neovascularization.

The expression "diseases associated to an undesired angiogenesis" relates to all those diseases where pathogenic angiogenesis occur i.e. when said process is harmful or undesirable, whether cancerous or not. The scope of the present invention thus excludes the treatment of angiogenesis in situations where it is necessary, such as wound healing. Diseases associated to an undesired angiogenesis which may be treated with the compounds in accordance with the present invention, without limitation, are inflammatory diseases, especially chronic inflammatory diseases such as rheumatoid arthritis, psoriasis, sarcoidosis and such like; autoimmune diseases; viral diseases; genetic diseases; allergic diseases; bacterial diseases; ophthalmological diseases such as diabetic retinopathy, premature retinopathy, proliferative atrial retinopathy, retinal vein oclusion, macular degeneration, senile discoid macular degeneration, neovascular ocular glaucoma, choroidal neovascularization diseases, retinal neovascularization diseases, rubeosis (angle neovascularization), corneal graft rejection, retrolental fibroplasia, epidermal keratoconjunctivitis, vitamin A deficiency, contact lens exhaustion, atopical keratitis, superior limbic keratitis, pterygium dry eye, Sjögrens syndrome, acne rosacea, phlyctenulosis, syphilis, micobacterial infections, lipid degeneration, burns with corrosive substances, bacterial ulcers, mycotic ulcers, protozoan infections, Kaposi sarcoma, Mooren's ulcer, Terrien marginal degeneration, marginal keratolysis, scleritis, chronic retinal detachment and such like; atherosclerosis; endometriosis; obesity; cardiac insufficiency; advanced renal insufficiency; endotoxemia; toxic shock syndrome; meningitis; silicon-induced fibrosis; asbestos-induced fibrosis; apoplexia; periodontitis; gingivitis; macrocytic anaemia; refractory anaemia; 5q deletion syndrome; conditions where the vascularization is altered as infection by HIV, hepatitis, hemorrhagic telangiectasia or Rendu-Osler-Weber's disease.

In a preferred embodiment, the disease associated to an undesired angiogenesis is a disease selected from cancer, rheumatoid arthritis, psoriasis, sarcoidosis, diabetic retinopathy, premature retinopathy, retinal vein oclusion, senile discoid macular degeneration, atherosclerosis, endometriosis and obesity, preferably cancer.

In a particular embodiment the diseases associated to an undesired angiogenesis are inflammatory diseases. "Inflammatory disease" is understood to be any disease where there is an excessive or altered inflammatory response that leads to inflammatory symptoms. Said inflammatory diseases which may be treated by compounds of the invention include, without limitation, Addison's disease, acne vulgaris, alopecia greata, amyloidosis, ankylosing spondylitis, ulcerations, aphthous stomatitis, arthritis, arteriosclerosis, osteoarthritis, rheumatoid arthritis, bronchial asthma, Bechet's disease, Boeck's disease, intestinal inflammatory disease, Crohn's disease, choroiditis, ulcerative colitis, celiac's disease, cryoglobulinemia, macular degeneration, dermatitis, dermatitis herpetiformis, dermatomyositis, insulin dependent diabetes, juvenile diabetes, inflammatory demyelinating disease, Dupuytren contracture, encephalomyelitis, allergic encephalomyelitis, endophthalmia, allergic enteritis, autoimmune enteropathy syndrome, erythema nodosum leprosum, ankylosing spondylitis, idiopathic facial paralysis, chronic fatigue syndrome, rheumatic fever, cystic fibrosis, gingivitis, glomerulonephritis, Goodpasture syndrome, Graves syndrome, Hashimoto's disease, chronic hepatitis, histiocytosis, regional ileitis, iritis, disseminated lupus erythematous, systemic lupus erythematous, cutaneous lupus erythematous, lymphogranuloma, infectious mononucleosis, miastenia gravis, transverse myelitis, primary idiopathic myxedema, nephrosis, obesity, sympathetic ophthalmia, granulomatous orchitis, pancreatitis, panniculitis, pemphigus vulgaris, periodontitis, polyarteritis nodosa, chronic polyarthritis, polymyositis, acute polyradiculitis, psoriasis, chronic obstructive pulmonary disease, purpura, gangrenous pioderma, Reiter's syndrome, diabetic retinopathy, rosacea, sarcoidosis, ataxic sclerosis, progressive systemic sclerosis, scleritis, sclerodermia, multiple sclerosis, disseminated sclerosis, acute anterior uveitis, vitiligo, Whipple's disease, diseases associated to AIDS, severe combined immunodeficiency and Epstein Barr's virus such as Sjögren's syndrome, osteoarticular tuberculosis and parasitic diseases such as leishmaniasis. Preferred inflammatory diseases are rheumatoid arthritis, psoriasis, sarcoidosis, diabetic retinopathy, macular degeneration, arteriosclerosis and obesity.

In another preferred embodiment the disease is cancer.

The terms "cancer" and "tumor" relate to the physiological condition in mammals characterized by unregulated cell growth. The antibodies binding specifically to the S100A4 protein of the first aspect of the invention or its fragments are useful for the treatment of any cancer or tumor, such as, without limitation, breast, heart, lung, small intestine, colon, splenic, kidney, bladder, head, neck, ovarian, prostate, brain, pancreatic, skin, bone, bone marrow, blood, thymic, uterine, testicular and liver tumors. Particularly, tumors which can be treated with said antibodies include but are not limited to adenoma, angiosarcoma, astrocytoma, epithelial carcinoma, germinoma, glioblastoma, glioma, hemangioendothelioma, hemangiosarcoma, hematoma, hepatoblastoma, leukemia, lymphoma, medulloblastoma, melanoma, neuroblastoma, osteosarcoma, retinoblastoma, rhabdomyosarcoma, sarcoma and teratoma. Particularly, the tumor/cancer is selected from the group of acral lentiginous melanoma, actinic keratosis adenocarcinoma, adenoid cystic carcinoma, adenomas, adenosarcoma, adenosquamous carcinoma, astrocytic tumors, Bartholin gland carcinoma, basal cell carcinoma, bronchial gland carcinoma, capillary carcinoid, carcinoma, carcinosarcoma, cholangiocarcinoma, cystadenoma, endodermal sinus tumor, endometrial hyperplasia, endometrial stromal sarcoma, endometrioid adenocarcinoma, ependymal sarcoma, Swing's sarcoma, focal nodular hyperplasia, germline tumors, glioblastoma, glucagonoma, hemagioblastoma, hemangioendothelioma, hemangioma, hepatic adenoma, hepatic adenomatosis, hepatocellular carcinoma, insulinoma, intraepithelial neoplasia, interepithelial squamous cell neoplasia, invasive squamous cell carcinoma, large-cell carcinoma, leiomyosarcoma, melanoma, malignant melanoma, malignant mesothelial tumor, medulloblastoma, medulloepithelioma, mucoepidermoid carcinoma, neuroblastoma, neuroepithelial adenocarcinoma, nodular melanoma, osteosarcoma, papillary serous adenocarcinoma, pituitary tumors, plasmacytoma, pseudosarcoma, pulmonary blastoma, renal cell carcinoma, retinoblastoma, rhabdomyosarcoma, sarcoma, serous carcinoma, small-cell carcinoma, soft tissue carcinoma, somatostatin secreting tumor, squamous carcinoma, squamous cell carcinoma, undifferentiated carcinoma, uveal melanoma, verrucous carcinoma, vipoma, Wilm's tumor. In one embodiment of the present invention, the tumor is selected from the group consisting of: breast carcinoma, prostate carcinoma, lung carcinoma, colorectal carcinoma, pancreatic carcinoma, renal carcinoma, gastric carcinoma, ovarian carcinoma, papillary thyroid carcinoma, melanoma, hepatocellular carcinoma, bladder carcinoma, liposarcoma invasive carcinoma, neuroblastoma, esophageal squamous carcinoma, osteosarcoma, gallbladder carcinoma, oral squamous carcinoma, endometrial carcinoma, and medulloblastoma. In another embodiment, the tumor is selected from colorectal carcinoma, pancreatic carcinoma, and any other S100A4 mediated tumors.

In a preferred embodiment of the invention, the tumor/cancer to be prevented or treated with said antibodies is selected from pancreatic cancer and colorectal cancer, preferably pancreatic cancer.

The term "pancreatic cancer" is understood as any malignant neoplasm of the pancreas including adenocarcinoma and some variants thereof.

The term "colorectal cancer" is understood as a cancer characterized by neoplasia in the colon, rectum or vermiform appendix. Colorectal cancer is clinically distinct from anal cancer, which affects the anus.

In one embodiment of the present invention, the medicament comprises one or more antibodies according to the first aspect of the invention as the sole therapeutic agent. However, the medicament of the invention can also contain one or several additional compounds for the treatment of cancer. Therefore, in another embodiment of the present invention, the medicament is prepared for the combined administration of an antibody according to the invention and one or more therapeutic agents useful in the treatment of said disease.

The term "therapeutic agent useful in the treatment of said disease" refers to an agent suitable for being used in the treatment of cancer.

For the treatment of cancer, the antibody of the invention can be used in combination with an additional therapeutically active compound, such as a cytotoxic agent, an antiangiogenic agent or an antimetastatic agent.

Cytotoxic agents which can be used in combination with the antibodies of the invention for the treatment of cancer include but are not limited to anthracycline antibiotics such as doxorubicin and daunorubicin, taxanes such as Taxol™ and docetaxel, vinca alkaloids such as vincristine and vinblastine, 5-fluorouracil (5-FU), leucovorin, irinotecan, idarubicin, mitomycin C, oxaliplatin, raltitrexed, tamoxifen, cisplatin, carboplatin, methotrexate, actinomycin D, mitoxantrone, blenoxane or mithramycin. Antiangiogenic agents which can be used in combination with the antibodies of the invention for the treatment of cancer include but are not limited to an antiangiogenic agent selected from the group of paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastat, penicillamine, PTK787/ZK 222584, RPI.4610, squalamine lactate, SU5416, thalidomide, combretastatin, tamoxifen, COL-3, neovastat, BMS-275291, SU6668, anti-VEGF antibodies, Medi-522 (Vitaxin II), CAI, interleukin 12, IM862, amiloride, angiostatin, K1-3 angiostatin, K1-5 angiostatin, Captopril, DL-alpha-difluoromethylornithine, DL-alpha-difluoromethylornithine HCl, endostatin, fumagillin, herbimycin A, 4-hydroxyphenylretinamide, juglone, laminin, laminin hexapeptide, laminin pentapeptide, lavendustin A, medroxyprogesterone, minocycline, placenta ribonuclease inhibitor, suramin, thrombospondin, antibodies directed against proangiogenic factors (for example, Avastin, Erbitux, Vectibix, Herceptin); low molecular weight tyrosine kinase inhibitors of proangiogenic growth factors (for example Tarceva, Nexavar, Sutent, Iressa); mTOR inhibitors (for example Torisel); interferon alpha, beta and gamma, IL-12, matrix metalloproteinase inhibitors (for example, COL3, marimastat, batimastat); ZD6474, SU11248, vitaxin; PDGFR inhibitors (for example Gleevec); NM3 and 2-ME2; cyclopeptides such as cilengitide. Antimetastatic agents which can be used in combination with the antibodies of the invention for the treatment of cancer include but are not limited to any agent capable of acting as an antimetastatic agent, such as alkylating agents; antimetabolites such as 5-fluorouracil, pemetrexed (MTA), raltitrexed (TDX); platinum cytotoxic agents such as cisplatin or oxaliplatin; topoisomerase inhibitors; antimicrotubule agents; anthracyclines; plant alkaloids; GTPase inhibitors; angiogenesis inhibitors; matrix metalloproteinase inhibitors; inhibitors of the cell cycle regulating kinase, such as cyclin-dependent kinases and cyclin inhibitors; Wnt signaling inhibitors; inhibitors of the E2F transcription factor; histone deacetylase inhibitors; AKT kinase or ATPase inhibitors.

"Combined administration" is understood as the antibody according to the invention is able to be administered jointly or separately, simultaneously, at the same time or sequentially with a therapeutic agent useful in the treatment of cancer in any order. For example, the administration of the antibody of the invention can be done first, followed by the administration of one or more therapeutic agents useful in the treatment of said pathology; or the administration of the antibody of the invention can be done last, preceded by the administration of one or more therapeutic agents useful in the treatment of said pathology; or the administration of the antibody of the invention can be done at the same time as the administration of one or more therapeutic agents useful in the treatment of said pathology.

The person skilled in the art will understand that in the context of the present invention, the medicament for the combined administration of an antibody according to the invention and an additional therapeutic agent useful in the treatment of cancer can be prepared as a single dosage form or in separate dosage forms.

In a preferred embodiment the specific anti-S100A4 antibody having anti-angiogenic activity is a monoclonal antibody, preferably an antibody produced by a hybridoma selected from the group ECACC 10022401, ECACC 11051801, ECACC 11051802, ECACC 11051803 and ECACC 11051804; more preferably produced by the hybridoma ECACC 10022401.

In another aspect, the invention relates to a specific anti-S100A4 antibody or fragment thereof produced by a hybridoma selected from the group ECACC 10022401, ECACC 11051801, ECACC 11051802, ECACC 11051803 and ECACC 11051804 or a fragment thereof for its use in medicine, The present invention also provides an antibody or fragment thereof or a monoclonal antibody according to any one of the embodiments presented herein, for use as a medicament for the treatment of any S100A4 mediated diseases.

The present invention also provides the use of an antibody or fragment thereof or a monoclonal antibody according to any one of the embodiments presented herein, for the manufacture of a medicament for the treatment of S100A4 mediated diseases.

The present invention also provides a method for treating S100A4 mediated diseases comprising administering to a subject in need of said treatment a pharmaceutically effective amount of the antibody or fragment thereof or monoclonal antibody according to any one of the embodiments presented herein.

Inflammation

The inventors have found that specific anti-S100A4 antibodies are useful in the prevention and/or treatment of diseases associated with inflammation. Thus, an aspect of the invention relates to the use of an antibody that binds specifically to the S100A4 protein or of a fragment thereof with capacity for binding to the antigen for the preparation of a medicament for the prevention and/or treatment of a disease associate with inflammation.

In another aspect, the invention relates to an antibody that binds specifically to the S100A4 protein or of a fragment thereof with capacity for binding to the antigen for use in the prevention and/or treatment of a disease associated with inflammation.

In another aspect, the invention relates to a method of treatment or prevention of a disease associated with inflammation in a subject which comprises the administration to said subject of an antibody that binds specifically to the S100A4 protein or of a fragment thereof with capacity for binding to the antigen.

The expression "antibody that binds specifically to the S100A4 protein", in the context of this aspect of the invention, refers to any antibody that recognizes specifically the S100A4 protein and not other proteins of the S100 family. Said expression includes antibodies previously disclosed in the prior art.

The term "fragment" refers to a fragment of the antibody having capacity for binding to the antigen. It is not necessary that said fragment has anti-angiogenic activity.

The expression "disease associated with inflammation" relates to all those diseases where pathogenic inflammation occurs i.e. when said process is harmful or undesirable, whether cancerous or not. Diseases associated with inflammation include inflammatory diseases, where there is an excessive or altered inflammatory response that leads to inflammatory symptoms. Said inflammatory diseases which may be treated by the antibodies of the invention include, without limitation, Addison's disease, acne vulgaris, alopecia greata, amyloidosis, ankylosing spondylitis, ulcerations, aphthous stomatitis, arthritis, arteriosclerosis, osteoarthritis, rheumatoid arthritis, bronchial asthma, Bechet's disease, Boeck's disease, intestinal inflammatory disease, Crohn's disease, choroiditis, ulcerative colitis, celiac's disease, cryoglobulinemia, macular degeneration, dermatitis, dermatitis herpetiformis, dermatomyositis, insulin dependent diabetes, juvenile diabetes, inflammatory demyelinating disease, Dupuytren contracture, encephalomyelitis, allergic encephalomyelitis, endophthalmia, allergic enteritis, autoimmune enteropathy syndrome, erythema nodosum leprosum, ankylosing spondylitis, idiopathic facial paralysis, chronic fatigue syndrome, rheumatic fever, cystic fibrosis, gingivitis, glomerulonephritis, Goodpasture syndrome, Graves syndrome, Hashimoto's disease, chronic hepatitis, histiocytosis, regional ileitis, iritis, disseminated lupus erythematous, systemic lupus erythematous, cutaneous lupus erythematous, lymphogranuloma, infectious mononucleosis, miastenia gravis, transverse myelitis, primary idiopathic myxedema, nephrosis, obesity, sympathetic ophthalmia, granulomatous orchitis, pancreatitis, panniculitis, pemphigus vulgaris, periodontitis, polyarteritis nodosa, chronic polyarthritis, polymyositis, acute polyradiculitis, psoriasis, chronic obstructive pulmonary disease, purpura, gangrenous pioderma, Reiter's syndrome, diabetic retinopathy, rosacea, sarcoidosis, ataxic sclerosis, progressive systemic sclerosis, scleritis, sclerodermia, multiple sclerosis, disseminated sclerosis, acute anterior uveitis, vitiligo, Whipple's disease, diseases associated with AIDS, severe combined immunodeficiency and Epstein Barr's virus such as Sjögren's syndrome, osteoarticular tuberculosis and parasitic diseases such as leishmaniasis. Preferred inflammatory diseases are rheumatoid arthritis, arteriosclerosis, psoriasis, inflammatory bowel disease and graft-versus-host disease.

The terms "medicament", "prevention" and "treatment" are defined in the context of the therapeutic uses of the antibodies of the invention.

In a preferred embodiment, the antibody that binds specifically to the S100A4 protein or a fragment thereof is an anti-S100A4 antibody having anti-angiogenic activity or a fragment thereof which substantially preserves the anti-angiogenic activity of said antibody wherein the antibody is selected from the group consisting of:
  (i) An antibody that recognizes an epitope of S100A4 comprising the sequence ELPSFLGKRT (SEQ ID NO: 3),
  (ii) An antibody that recognizes an epitope of S100A4 comprising the sequence EGFPDKQPRKK (SEQ ID NO: 24) and
  (iii) An antibody produced by the hybridoma ECACC 11051804.

In a more preferred embodiment the antibody is produced by a hybridoma selected from the group ECACC 10022401, ECACC 11051801, ECACC 11051802, ECACC 11051803 and ECACC 11051804; more preferably the hybridoma is ECACC 10022401.

Conjugates of the Antibodies of the Invention and their Uses

Given that the antibodies of the first aspect of the invention are capable of binding to the S100A4 protein and that this protein is overexpressed in cancer, the specific anti-S100A4 antibody having anti-angiogenic activity or a fragment thereof according to the first aspect of the invention constitute agents suitable for carrying compounds with therapeutic activity towards the expression sites of S100A4.

The S100A4 protein is expressed, as has been detailed above, in a great variety of cancers. Said protein is also expressed in diseases associated with inflammation, such as rheumatoid arthritis.

Therefore, in another aspect, the invention relates to a conjugate comprising an antibody or a fragment thereof according to the first aspect of the invention and a second component selected from the group of:
  a) an antiangiogenic agent,
  b) an antimetastatic agent,
  c) a cytotoxic agent
  d) an anti-inflammatory agent In a preferred embodiment the second component is selected from the group of: a) an antiangiogenic agent, b) an antimetastatic agent, and c) a cytotoxic agent.

"Conjugate" in the context of the present invention is understood as an assembly formed by an antibody according to the first aspect of the invention bound, linked or associated to at least one second component.

The antibodies or fragment thereof according to the first aspect of the invention have been described in the context of said first aspect.

"Second component" is understood as a molecule with therapeutic activity which is directed to its action site by means of the monoclonal antibody of the invention.

The S100A4 protein is overexpressed in tumor cells. Therefore, the antibodies of the invention can be used to direct antitumor drugs to the expression sites.

As it is used in the present invention, the term "cytotoxic agent" relates to an agent which is capable of promoting cell death and which has capacity for reducing the growth, stopping the growth or destroying cells and, particularly, rapidly proliferating cells and, yet more particularly, tumor cells. Cell death can be caused by any mechanism, such as for example apoptosis, although it is not limited to this cause, by the metabolism inhibition, the interference with the organization of the cytoskeleton or the chemical modification of the DNA. The term cytotoxic agent comprises any chemotherapy agent including small organic molecules, peptides, oligonucleotides and the like; toxins; enzymes; cytokines; radioisotopes or radiotherapy agents.

"Chemotherapy agents" are understood as chemical compounds such as, without limitation, anthracycline antibiotics such as doxorubicin and daunorubicin, taxanes such as Taxol™ and docetaxel, vinca alkaloids such as vincristine and vinblastine, 5-fluorouracil (5-FU), leucovorin, irinotecan, idarubicin, mitomycin C, oxaliplatin, raltitrexed, tamoxifen, cisplatin, carboplatin, methotrexate, actinomycin D, mitoxantrone, blenoxane or mithramycin, antimetabolites such as gemcitabine.

"Toxin" is understood as a toxic agent which conjugates with the antibody of the invention forming an immunotoxin. The conjugation of determined toxins with antibodies reduces the toxicity of the former, enabling their use as therapeutic agents, because otherwise they would be too toxic. The binding between the toxin and the antibody is performed chemically, conserving its biological activity. Their separation generally occurs in the lysosomes of the target cells recognized by the antibody such that the mentioned chemical binding is only broken in the enclosed acidic cellular environment provided by the lysosomes. Toxins useful in the context of the present invention are plant toxins, bacterial toxins, toxins of fungal or animal origin and fragments thereof, such as, without limitation, the ricin A-chain, saponin, the diphtheria A-chain, active non-binding fragments of the diphtheria toxin, *Pseudomonas aeruginosa* exotoxin A-chain, abrin A-chain, modecin A-chain, α-sarcin, *Leurites fordii* A-proteins, dianthin proteins, *Phytolaca americana* (PAPI, PAPII and PAP-S) proteins, *Momordica charantia* inhibitor, curcine, crotin, *Saponaria officinalis* inhibitor, gelonin, mitogelin, restrictocin, phenomycin, enomycin and trichothecenes.

"Enzymes" are understood in the context of the present invention as toxin or drug activating enzymes, such as, without limitation, alkaline phosphatase which activates etoposide and doxorubicin; carboxypeptidase G2 which activates nitrogen mustards; beta-lactamase which activates doxorubicin, paclitaxel and mitomycin.

"Cytokines" are understood as peptides of different sizes and molecular weights which synthesize the cells of the immune system for the purpose of regulating the immune response, and they can be hormones, growth factors, necrosis factors, etc. They can be of natural origin or from recombinant cell cultures and biologically active equivalents of natural sequence cytokines. Their conjugation with antibodies gives rise to immunocytokines Cytokines useful in the present invention are, without limitation, TNF factor alpha, INF-gamma, GM-GSF factor or IL-2.

"Radioisotopes" is understood as radioactive isotopes such as, without limitation, $^{131}$I, $^{90}$Y, $^{177}$Lu, $^{188}$Re, $^{67}$Cu, $^{211}$At, $^{213}$Bi, $^{125}$I, $^{111}$In.

"Antiangiogenic agent" is understood as a chemical or biological substance which inhibits or reduces the formation of new blood vessels, i.e., angiogenesis. Examples of antiangiogenic agents that can be conjugated with the antibodies of the first aspect of the invention include, without limitation, an antiangiogenic agent selected from the group of paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastat, penicillamine, PTK787/ZK 222584, RPI.4610, squalamine lactate, SU5416, thalidomide, combretastatin, tamoxifen, COL-3, neovastat, BMS-275291, SU6668, anti-VEGF antibodies, Medi-522 (Vitaxin II), CAI, interleukin 12, IM862, amiloride, angiostatin, K1-3 angiostatin, K1-5 angiostatin, Captopril, DL-alpha-difluoromethylornithine, DL-alpha-difluoromethylornithine HCl, endostatin, fumagillin, herbimycin A, 4-Hydroxyphenylretinamide, juglone, laminin, laminin hexapeptide, laminin pentapeptide, lavendustin A, medroxyprogesterone, minocycline, placenta ribonuclease inhibitor, suramin, thrombospondin, antibodies directed against proangiogenic factors (for example, Avastin, Erbitux, Vectibix, Herceptin); low molecular weight tyrosine kinase inhibitors of proangiogenic growth factors (for example Tarceva, Nexavar, Sutent, Iressa); mTOR inhibitors (for example Torisel); interferon alpha, beta and gamma, IL-12, matrix metalloproteinase inhibitors (for example, COL3, marimastat, batimastat); ZD6474, SU11248, vitaxin; PDGFR inhibitors (for example Gleevec); NM3 and 2-ME2; cyclopeptides such as cilengitide.

"Antimetastatic agent" is understood as a chemical or biological substance which inhibits or reduces metastasis, i.e., the distance propagation, fundamentally by the lymphatic or blood stream, of the cancer causing cells, and the growth of new tumors in the destination sites of said metastasis.

Antimetastatic agents that can be conjugated with the antibodies of the first aspect of the invention include, without limitation, any cytotoxic agent capable of acting as an antimetastatic agent, such as alkylating agents; antimetabolites such as 5-fluorouracil, permetrexed (MTA), raltitrexed (TDX); platinum cytotoxic agents such as cisplatin or oxaliplatin; topoisomerase inhibitors; antimicrotubule agents; anthracyclines; plant alkaloids; GTPase inhibitors; angiogenesis inhibitors; matrix metalloproteinase inhibitors; inhibitors of the cell cycle regulating kinases, such as the cyclin-dependent kinases and cyclin inhibitors; Wnt signaling inhibitors; inhibitors of the E2F transcription factor; histone deacetylase inhibitors; AKT kinase or ATPase inhibitors.

The conjugates of the antibody and other agents can be created using a variety of coupling agents or bifunctional protein linkers. The linker can be a "detachable linker" which allows the release of the agent in the cell, such as an acid-labile linker, a peptidase-sensitive linker, a dimethyl linker or a linker containing disulphide.

The S100A4 protein is also expressed in diseases associated with inflammation. Therefore, the antibodies of the invention can be used to direct anti-inflammatory drugs to the expression sites.

The term "anti-inflammatory agent" means any anti-inflammatory drug that inhibits or blocks the prostaglandin synthesis. Anti-inflammatory agents useful are, without limitation, 5-aminosalicylic acid and medicaments containing it (sulfasalazine, mesalamine, mesalazine, olsalazine); acetylsalicylic acid; corticosteroids such as hydrocortisone, cortisone, triamcinolone, budesonide, prednisone, deflazacort, methotrexate; infliximab; adalimumab.

In a preferred embodiment the specific anti-S100A4 antibody of the conjugate of the invention is a monoclonal antibody, preferably a monoclonal antibody or fragment thereof produced by a hybridoma selected from the group ECACC 10022401, ECACC 11051801, ECACC 11051802, ECACC 11051803 and ECACC 11051804 or a fragment thereof; more preferably produced by the hybridoma ECACC 10022401.

Thus, in another aspect, the invention relates to conjugates comprising an antibody or a fragment thereof according to the first aspect of the invention for use in medicine.

In another aspect, the invention relates to the use of a conjugate comprising a specific anti-S100A4 antibody having anti-angiogenic activity or a fragment thereof according to the first aspect of the invention for the preparation of a medicament for the prevention and/or treatment of a disease selected from a metastasis, a disease associated to an undesired angiogenesis and a disease associated with inflammation; preferably a disease selected from a metastasis and a disease associated to an undesired angiogenesis.

In another aspect, the invention relates to a conjugate comprising a specific anti-S100A4 antibody having anti-angiogenic activity or a fragment thereof according to the first aspect of the invention for use in the prevention and/or treatment of a disease selected from a metastasis, a disease associated to an undesired angiogenesis and a disease associated with inflammation; preferably a disease selected from a metastasis and a disease associated to an undesired angiogenesis.

In another aspect, the invention relates to a method of treatment or prevention in a subject suffering from a disease selected from a metastasis, a disease associated to an undesired angiogenesis and a disease associated with inflammation which comprises administering to said subject a conjugate comprising a specific anti-S100A4 antibody having anti-angiogenic activity or a fragment thereof according to the first aspect of the invention. In a preferred embodiment the disease is selected from a metastasis and a disease associated to an undesired angiogenesis.

In preferred embodiments, the specific anti-S100A4 antibody is a monoclonal antibody, preferably a monoclonal antibody or fragment thereof produced by a hybridoma selected from the group ECACC 10022401, ECACC 11051801, ECACC 11051802, ECACC 11051803 and ECACC 11051804 or a fragment thereof; more preferably produced by the hybridoma ECACC 10022401.

"Medicament", in the context of these inventive aspects, is understood as a pharmaceutical composition comprising a conjugate of an antibody of the first aspect of the invention or a fragment thereof with a compound useful in the treatment of cancer, specifically in the treatment of a disease selected from a metastasis and a disease associated to an undesired angiogenesis, or with a compound useful in the treatment of a disease associated with inflammation.

The terms "prevention", "treatment", "metastasis", "disease associated to an undesired angiogenesis" and "disease associated with inflammation" have been previously defined in the context of the therapeutic uses of the invention.

Diagnostic Method of the Invention

Since the S100A4 protein is secreted into the extracellular medium by the tumor cells, its presence can be detected in various biofluids, it being able to be used for diagnosing cancer. Said protein has been found also in plasma and joint synovial fluid of patients suffering from diseases associated with inflammation such as rheumatoid arthritis.

Thus, in an aspect the invention relates to an in vitro method for diagnosing cancer or a disease associated with inflammation in a subject which comprises:
 (a) detecting the levels of the S100A4 protein or of a variant thereof in a biofluid of said subject by means of using a monoclonal antibody produced by a hybridoma selected from the group consisting of ECACC 10022401, ECACC 11051801, ECACC 11051802, ECACC 11051803 and ECACC 11051804 or a functional variant of said antibody
 (b) comparing said levels with a reference value
wherein increased levels of the S100A4 protein or of a variant thereof with respect to the reference value are indicative of the subject suffering from cancer or a disease associated with inflammation.

In the context of the present invention, "in vitro method for diagnosing cancer" is understood as a method which allows showing the existence of a malignant tumor in a subject by means of detecting the presence of the S100A4 protein soluble in a biofluid isolated from the patient. It is also useful for documenting the expression of S100A4 produced by a tumor prior to administering S100A4 selecting drugs to allow a suitable selection of patients and the determination of the optimal dose.

In the context of the present invention, "in vitro method for diagnosing a disease associated with inflammation" is understood as a method which allows showing the existence of an inflammatory disease in a subject by means of detecting to presence of the S100A4 protein soluble in a biofluid isolated from the patient.

"Subject" in the present invention is understood as any animal classified as mammal and includes but is not limited to domestic and farm animals, primates and humans, for example human beings, non-human primates, cows, horses, pigs, sheep, goats, dogs, cats or rodents. Preferably, the subject is a female or male human being of any race or age. In the context of the present invention, the subject is a subject who potentially suffers from cancer or a disease associated with inflammation or a subject who has been previously diagnosed with cancer or a disease associated with inflammation.

The first step of the method of the invention comprises determining the levels of the S100A4 protein or of a variant thereof in a biofluid of the study subject by using the monoclonal antibodies of the invention.

The term "biofluid" in the context of the present invention refers to any biological secretion or fluid, whether physiological or pathological, which is produced in the body of a subject. Such biofluids include, without limitation, blood, plasma, serum, bronchoalveolar washing fluid, urine, nasal secretion, ear secretion, urethral secretion, cerebrospinal fluid, pleural fluid, synovial fluid, peritoneal fluid, ascites fluid, pericardial liquid, amniotic fluid, gastric juice, lymphatic fluid, interstitial fluid, saliva, sputum, liquid deposition, tears, mucus, sweat, milk, semen, vaginal secretions, fluid coming from ulcer, blisters, abscesses and other surface eruptions. Said samples can be obtained by conventional methods, using processes known in the state of art by the person skilled in the art, such as blood extraction, instilling and aspirating liquid during bronchofibroscopy, cisternal, ventricular or lumbar puncture, pleural puncture or thoracocentesis, joint or synovial percutaneous puncture, abdominal puncture, amniocentesis, expectoration, peritoneal percutaneous puncture, pericardial percutaneous puncture, etc., or by simple harvesting.

In a preferred embodiment, the biofluid is selected from blood, plasma and serum, preferably serum, more preferably plasma. The blood sample is typically extracted by means of puncturing an artery or vein, normally a vein from the inner part of the elbow or from the back of the hand, the blood sample being collected in a air-tight vial or syringe. A capillary puncture normally on the heel or on the distal phalanxes of fingers can be performed for analysis by means of a micromethod. Serum can be obtained from the complete blood sample and in the absence of anticoagulant by leaving the sample to settle for 10 minutes so that it coagulates and subsequently centrifuging it at 1,500 rpm for 10 minutes for the purpose of separating the cells (precipitate) from the serum (supernatant). In turn, to obtain the plasma sample the complete blood is contacted with an anticoagulant and is centrifuged at 3,000 rpm for 20 minutes. The precipitate of said centrifugation corresponds to the formed elements, and the supernatant corresponds to the plasma.

The serum or the plasma obtained can be transferred to a storage tube for sample analysis by means of the method of the invention.

In another preferred embodiment the biofluid is joint synovial fluid.

The levels of expression of the S100A4 protein can be detected and quantified by means of conventional methods. Said methods include, without limitation, the detection of S100A4 by measuring its affinity to one of its ligands such as RAGE, and the subsequent quantification of the S100A4-ligand complex; or by means of using the monoclonal antibodies with capacity of binding specifically to the S100A4 protein (or fragments thereof which contain the antigenic determinants) produced by a hybridoma selected from the group consisting of ECACC 10022401, ECACC 11051801, ECACC 11051802, ECACC 11051803 and ECACC 11051804 or a functional variant of said antibody. Then, to resulting antigen-antibody complexes are quantified. In a preferred embodiment of the invention the antibody used is the antibody produced by the hybridoma ECACC 10022401.

The invention also contemplates the use of functional variants of said antibodies. "Functional variant" of the monoclonal antibodies of the invention is understood as any molecule sharing with said monoclonal antibodies one or more of the functions described in the present invention associated with said monoclonal antibodies, both in vitro and in vivo, and having a minimal identity in the amino acid sequence. The functional variants of the monoclonal antibodies of the invention can be derived from said sequences by means of insertion, substitution or deletion of one or more amino acids and can be obtained by recombinant and/or synthetic means.

The functional variants of the monoclonal antibodies of the invention must conserve their capacity for binding to the S100A4 antigen and also the capacity for inhibiting one or more characteristic functions of the S100A4 protein, such as the angiogenesis. Said functions can be determined by means of the methods described in the examples of the present invention.

The functional variants of the monoclonal antibodies of the invention include polypeptides showing at least 60%, 65%, 70%, 72%, 74%, 76%, 78%, 80%, 90%, 95%, 97%, 99% similarity or identity with the polypeptide sequence of said antibodies. The degree of identity between two polypeptides is determined using algorithms implemented in a computer and methods which are widely known by the persons skilled in the art. The identity between two amino acid sequences is preferably determined using the BLASTP algorithm (BLAST Manual, Altschul, S. et al., NCBI NLM NIH Bethesda, Md. 20894, Altschul, S., et al., J., 1990, Mol. Biol. 215:403-410).

In addition, the antibodies used in the method of the invention may or may not be labeled with a detectable agent. In a particular embodiment the antibody used is conjugated to a detectable agent.

In the context of the present invention, the terms "detectable agent" and "labeling" are synonyms and they refer to an agent the nature of which allows its detection by means of enzymatic, radioactive or fluorescence methods. The detectable compound can be an enzyme, a radioactively labeled compound or a radioactive isotope, a fluorochrome, a chemiluminescent reagent, an enzymatic substrate or cofactor, an enzymatic inhibitor, a particle, a dye, etc.

The compounds radioactively labeled by means of radioactive isotopes, also called radioisotopes or radionuclides, may include, without limitation, $^3H$, $^{14}C$, $^{15}N$, $^{35}S$, $^{90}Y$, $^{99}Tc$, $^{111}In$, $^{125}I$, $^{131}I$. The fluorescent labels may include, without limitation, rhodamine, phosphorus-lanthanides or FITC. The enzymatic labels may include, without limitation, horseradish peroxidase, β-galactosidase, luciferase or alkaline phosphatase. The preferred labeling include, but are not limited to, fluorescein, a phosphatase such as alkaline phosphatase, biotin, avidin, a peroxidase such as horseradish peroxidase and compounds related to biotin or compounds related to avidin (for example, streptavidin or ImmunoPure® NeutrAvidin available from Pierce, Rockford, Ill.).

There is a wide variety of well known assays which can be used in the present invention, these assays use primary non-labeled antibodies and secondary labeled antibodies: such techniques include Western-blot or Western transfer, ELISA (Enzyme Linked Immunosorbent Assay), RIA (radioimmunoassay), competitive EIA (competitive enzyme immunoassay), DAS-ELISA (double antibody sandwich ELISA), or techniques based on the use of protein microarrays or biochips which include specific antibodies or assays based on the colloidal precipitation in forms such as reactive strips. Other ways for detecting the S100A4 protein include techniques such as affinity chromatography, ligand binding assays, etc.

In a particular embodiment, the quantification of the levels of S100A4 is performed by means of Western-blot or ELISA.

In yet a more particular embodiment, the levels of the S100A4 protein or of its variants are determined by Western-blot. Western-blot is based on detecting the previously resolved proteins by means of electrophoresis in gel under denaturing conditions and being immobilized on a membrane, generally nitrocellulose, by means of incubation with a antibody specific for S100A4 and a development system (e.g. chemiluminescent).

In another preferred embodiment, the diagnostic is performed by means of ELISA. Said technique is based on the detection of the S100A4 protein in a sample by means of an anti-S100A4 antibody immobilized on a substrate and the subsequent detection of the S100A4-antibody complex by means of a second antibody.

The term "protein" as used herein refers to a molecular chain of amino acids, joined by covalent or non-covalent bonds. The term further includes all the physiologically relevant post-translational chemical modification forms. Post-translational modifications which fall within the scope of the present invention include, for example, signal peptide cleavage, glycosylation, acetylation, phosphorylation, isoprenylation, proteolysis, myristoylation, protein folding and proteolytic process, etc. Additionally, the proteins can include non-natural amino acids formed by post-translational modifications or by means of introducing non-natural amino acids during translation.

The term "S100A4" has been defined in the context of the first inventive aspect of the invention. For the diagnostic method of the invention, the detected S100A4 is that which corresponds to the species to which the subject from which the biofluid sample to be analyzed has been extracted belongs.

As mentioned above, variants of said protein can also be used to measure the levels of the S100A4 protein in the method of the invention.

Therefore, variants of the S100A4 protein can be: (i) those in which one or more of the amino acid residues are substituted by a conserved or non-conserved amino acid residue (preferably a conserved amino acid) and such substituted amino acid residue may or may not be encoded by the genetic code, (ii) those in which there are one or more modified amino acid residues, e.g. residues that are modified by the coupling of substituting groups, (iii) those in which the protein is an alternative splicing variant of the S100A4 and/or (iv) fragments of the protein. The fragments include proteins generated through proteolytic process (including proteolysis at multiple sites) of an original sequence. Said variants fall within the scope of the present invention.

Variants according to the present invention include amino acid sequences that are at least 60%, 70%, 80%, 90%, 95% or 96% similar or identical to the original amino acid sequence. As it is known, the "similarity" between two proteins is determined by means of comparing the amino acid sequence of a protein with a sequence of a second protein. The degree of identity between two proteins is determined using computer algorithms and methods that are widely known by the person skilled in the art, preferably using the BLASTP algorithm [BLASTManual, Altschul, S., et. al., NCBI NLM NIH Bethesda, Md. 20894, Altschul, S., et. al., J. Mol. Biol. 215: 403-410 (1990)].

In a particular embodiment, the variant is a variant from mammal, preferably a human variant, more preferably with at least 60%, 70%, 80%, 90%, 95% or 96% similarity or identity with the original amino acid sequence.

The person skilled in the art will appreciate that the method of the invention can be put into practice using both the absolute level and the relative level of expression of the S100A4 protein. Thus, in the present invention, the expression "levels of the S100A4 protein" is used to refer both the absolute levels and the relative levels of said protein.

The expression "absolute levels" refers to the total amount of the protein of interest in a sample. Said value may be given as the concentration of protein expressed in units of mass per unit of volume (e.g. in ng/ml of sample), in the number of protein molecules per unit of volume (e.g. in pmol protein/ml of sample), in the units of mass of S100A4 protein per unit of mass of total protein (pg S100A4/mg total protein) or in the number of S100A4 molecules per unit of mass of total protein (e.g. in pmol S100A4/mg of total protein).

The expression "relative levels" refers to the relationship between the levels of expression of the S100A4 protein object of the study and of a reference protein, i.e., the concentration of S100A4 protein in normalized form with respect to said reference protein is defined.

In order to normalize the values of protein between the different samples, it is possible to compare the levels of S100A4 protein in the samples to be analyzed with the expression of a control protein. "Control protein" in the present invention is understood as a protein the levels of expression of which do not change or only change in limited amounts in the tumor cells with respect to the non-tumor cells. Preferably, the control protein is a protein encoded by genes that are constitutively expressed, that are those genes always active or being transcribed constantly, such that these proteins are constitutively expressed and carry out essential cellular functions. Preferred control proteins that can be used in the present invention include, without limitation, β-2-microglobulin (B2M), ubiquitin, 18-S ribosomal protein, cyclophilin, GAPDH, PSMB4, tubulin and actin.

The person skilled in the art understands that mutations in the amino acid sequence of the S100A4 protein do not affect the detection of the expression thereof and, therefore, the variants of this protein generated by mutations of the amino acid sequence fall within the scope of the present invention.

Once the level of expression of S100A4 in a sample has been determined, step (b) of the invention which consists of comparing the levels of S100A4 obtained in step (a) with a reference value takes place.

The "reference value" derives from a sample collection formed preferably by a mixture of the biofluid to be analyzed from normal individuals not affected by cancer. Said reference value can be determined by means of techniques well known in the state of the art, for example, determining the mean of the levels of S100A4 protein measured in biofluids taken from healthy subjects. The reference value can also be obtained from the constitutively expressed proteins taken from the same subject to be analyzed.

Once the reference value is established, the value of the levels of S100A4 obtained in step (a) can be compared with this reference value and, therefore, allows detecting alterations in the levels of S100A4 protein of the subject with respect to the reference value. More specifically, in the method of the invention, an increase of the levels of S100A4 with respect to the reference value is indicative of the subject suffering from cancer or a disease associated with inflammation.

In the context of the present invention, "increased levels" with respect to the reference value is understood as a variation of the levels of S100A4 above the reference value of at least 1.1 times, 1.5 times, 5 times, 10 times, 20 times, 30 times, 40 times, 50 times, 60 times, 70 times, 80 times, 90 times, 100 times or even more times as compared to the reference value.

Therefore, once said comparison has been performed, the method of the invention allows diagnosing if the subject suffers from cancer or a disease associated with inflammation. In a particular embodiment, the method is suitable for diagnosing cancer, particularly pancreatic cancer and colorectal cancer.

In another particular embodiment, the method is suitable for diagnosing a disease associated with inflammation, preferably rheumatoid arthritis.

The terms "cancer" and "disease associated with inflammation" have been defined previously.

Methods for Detecting S100A4

The antibodies as defined in the first aspect of the invention can also be useful for detecting S100A4 in biological samples of another type different from a biofluid. Said detection processes are advantageously applied for the diagnosis and/or prognosis of cancer or diseases associated with inflammation the cells of which are cells which express the S100A4 protein.

These antibodies can be used for identifying cells and tissues which express the S100A4 protein by means of standard techniques such as immunofluorescence, flow cytometry, affinity chromatography or immunoprecipitation. For example, a monoclonal antibody of the invention can facilitate the identification of a tumor cell which expresses an S100A4 protein and allows diagnosing cancer in a subject.

Thus, in another aspect, the invention relates to an in vitro method for diagnosing cancer or a disease associated with inflammation in a subject which comprises:
  (i) detecting the levels of the S100A4 protein or of a variant thereof in a cell or tissue of said subject by means of a specific anti-S100A4 monoclonal antibody produced by a hybridoma selected from the group of ECACC 10022401, ECACC 11051801, ECACC 11051802, ECACC 11051803 and ECACC 11051804 or a functional variant of said antibody
  (ii) comparing said levels with a reference value
wherein increased levels of the S100A4 protein or of a variant thereof with respect to the reference value are indicative of the subject suffering from cancer or a disease associated with inflammation.

The term "in vitro method" implies that said method is carried out in a biological sample isolated from the subject from whom it is taken. Said biological sample can be a cell, such as a blood cell, an epithelial cell, a germ cell, etc. or also a biopsy sample of a tissue.

The terms "levels of the S100A4 protein", "variant", "reference value" and "increased levels" have already been defined in the context of the diagnostic method of the invention.

The detection can be facilitated by means of the coupling (i.e., physical binding) of the antibody to a labeling group.

In another aspect, the invention relates to a method for detecting S100A4 in a sample which comprises:
(i) contacting a sample suspected of containing S100A4 with a specific anti-S100A4 antibody or a fragment thereof as defined in the first aspect of the invention and
(ii) detecting the formation of immune complexes between S100A4 and the antibody or the fragment thereof
wherein the detection of immune complexes between S100A4 and the antibody is indicative of the presence of S100A4 in the sample.

In a preferred embodiment of the method for detecting S100A4 the specific anti-S100A4 antibody is a monoclonal antibody produced by a hybridoma selected from the group of ECACC 10022401, ECACC 11051801, ECACC 11051802, ECACC 11051803 and ECACC 11051804 or a functional variant of said antibody.

Given that the monoclonal antibodies of the invention recognize the S100A4 protein, they can be used for purifying said protein from a sample.

Preferably, for use in the purification of S100A4, the monoclonal antibodies of the first aspect of the invention are used by associating them with a support or substrate. In principle, any type of support can be used in the methods of the invention, although the use of polymeric type supports such as Sephadex, dextran, polyamino acids soluble in water, polyethylene glycol (PEG), polyglutamic acid (PGA), polylactic acid (PLA), polylactic-co-glycolic acid (PLGA), poly(D,L-lactide-co-glycolide) (PLA/PLGA), poly(hydroxyalkyl-methacrylamide), a polyglycerol, a polyamidoamine (PAMAM) and a polyethyleneimine (PEI) is preferable.

Typically, the purification of S100A4 using the monoclonal antibodies of the first aspect of the invention is carried out by means of a process which comprises the steps of:
(i) contacting the sample from which the S100A4 protein is to be purified with an antibody produced by a hybridoma selected from the group of ECACC 10022401, ECACC 11051801, ECACC 11051802, 11051803 and ECACC 11051804 or a fragment thereof immobilized on a support in conditions suitable for the binding between the antibody and the S100A4 protein to take place;
(ii) washing the complexes formed in step (i) to remove all those compounds from the sample that are nonspecifically bound to the support-antibody conjugate and
(iii) eluting the S100A4 protein that is bound to the compound.

The method for purifying the S100A4 protein of the invention can be carried out using any known protein purification method by means of affinity, including, for example, affinity chromatography columns the stationary phase of which is formed by the monoclonal antibodies according to the first aspect of the invention conjugated to a solid support.

Kits of the Invention and Uses Thereof

In another aspect, the invention relates to a kit for diagnosing cancer or a disease associated with inflammation in a biofluid which comprises at least one antibody or a fragment thereof according to the first aspect of the invention. In a preferred embodiment the antibody is an antibody produced by a hybridoma selected from the group of ECACC 10022401, ECACC 11051801, ECACC 11051802, 11051803 and ECACC 11051804 or a fragment thereof. In a particular embodiment the disease is cancer, preferably pancreatic cancer o colorectal cancer. In another preferred embodiment the disease is a disease associated with inflammation, preferably rheumatoid arthritis.

In another aspect, the invention relates to the use of a kit as previously defined for diagnosing cancer or a disease associated with inflammation in the biofluid of a subject. In a particular embodiment the disease is cancer, preferably pancreatic cancer o colorectal cancer. In another preferred embodiment the disease is a disease associated with inflammation, preferably rheumatoid arthritis.

The term "kit", as used in the present document, refers to a combination of a set of reagents suitable for detecting the levels of S100A4 together with one or more types of elements or components (for example, other types of biochemical reagents, containers, packaging suitable for its commercial sale, substrates to which the reagents are bound, electronic hardware components, etc.)

In the present invention, "reagent suitable for detecting the levels of S100A4" is understood as a specific anti-S 100A4 monoclonal antibody produced by a hybridoma selected from the group of ECACC 10022401, ECACC 11051801, ECACC 11051802, ECACC 11051803 and ECACC 11051804 or a fragment thereof and, optionally, reagents for detecting one or more constitutive proteins.

As it will be understood by the person skilled in the art, the antibodies of the kit of the invention can be used in all the techniques for determining the levels of protein known to be suitable for the analysis of a biofluid, such as Western-blot or Western transfer, ELISA, RIA, competitive EIA, DAS-ELISA, techniques based on the use of biochips, protein microarrays, assays of colloidal precipitation in reactive strips, etc.

The antibodies can be fixed to a solid support such as a membrane, a plastic or a glass, optionally treated to facilitate the fixation of said antibodies to the support. Said solid support comprises, at least, a set of antibodies which specifically recognize the S100A4 protein, and which can be used for detecting the levels of expression of said protein.

The kits of the invention additionally comprise reagents for detecting a protein encoded by a constitutive gene. The availability of said additional reagents allows normalizing the measurements performed in different samples (for example, the sample to be analyzed and the control sample) to rule out that the differences in the expression of the biomarkers are due to a different quantity of total protein amount in the sample more than the real differences in the relative levels of expression. The constitutive genes in the present invention are genes that are always active or being transcribed constantly and which encode for proteins that are expressed constitutively and carry out essential cellular functions. Proteins that are expressed constitutively and can be used in the present invention include, without limitation, $\beta$-2-microglobulin (B2M), ubiquitin, 18-S ribosomal protein, cyclophilin, GAPDH, PSMB4, tubulin and actin.

All the particular embodiments of the method of the present invention are applicable to the kits of the invention and to their uses.

Methods for Customizing Therapy

The inventors have found that the treatment of a subject suffering from cancer with a monoclonal antibody according to the invention blocks the totality of circulant S100A4 protein that was higher before the treatment.

Thus, in another aspect, the invention relates to an in vitro method for designing a customized therapy for a subject diagnosed with cancer which comprises
(i) determining the levels of the S100A4 protein or of a variant thereof in a biofluid of said subject and (ii) comparing the levels of S100A4 protein with a reference value wherein increased the levels of S100A4 protein or of a variant thereof with respect to a reference level is indicative that the patient is to be treated with a specific anti-S100A4 antibody having anti-angiogenic activity or a fragment thereof which substantially preserves the anti-angiogenic activity of said antibody wherein the antibody is selected from the group consisting of
   (a) an antibody that recognizes an epitope of S100A4 comprising the sequence ELPSFLGKRT (SEQ ID NO: 3),
   (b) an antibody that recognizes an epitope of S100A4 comprising the sequence EGFPDKQPRKK (SEQ ID NO: 24) and
   (c) an antibody produced by the hybridoma ECACC 11051804.

The term "designing a customized therapy" means that the results obtained by said method are useful to decide if the subject is a candidate for a treatment with the monoclonal antibodies of the invention.

The term "subject" means human and non-human animals diagnosed with cancer. Non-human animals includes all vertebrates, e.g., mammals and non-mammals, such as primates and non-human primates, sheep, dog, rabbits, rats, mice, cow, chickens, amphibians, and reptiles.

The terms "cancer", "S100A4 protein", "variant of said protein", "biofluid", "monoclonal antibody", "hybridoma", "functional variant of the antibody" have been defined previously.

In the context of the present aspect, the subject is selected for being treated with at least a monoclonal antibody of the invention and the same antibody is used to monitor the levels of S100A4. When the levels of S100A4 protein are higher than a reference level, the subject is a candidate for a therapy with the monoclonal antibody of the invention administered.

The expression level of the S100A4 protein can be quantified by means of any conventional method which allows detecting and quantifying said protein in a sample from a patient. The antibodies which are used in these assays can be labeled or not. Illustrative examples of markers which can be used include radioactive isotopes, enzymes, fluorophores, chemiluminescent reagents, enzymatic substrates or cofactors, enzymatic inhibitors, particles, dyes, etc. There is a wide variety of known assays which can be used in the present invention which use non-labeled antibodies (primary antibody) and labeled antibodies (secondary antibody); these techniques include Western blot, ELISA (enzyme-linked immunosorbent assay), RIA (radioimmunoassay), competitive EIA (competitive enzymatic immunoassay), DAS-ELISA (double antibody sandwich ELISA), immunocytochemical and immunohistochemical techniques, techniques based on the use of protein biochips or microarrays including specific antibodies or assays based on colloidal precipitation in formats such as dipsticks.

In a preferred embodiment, the determination of the levels of the S100A4 protein in step (i) is carried out by means of using a monoclonal antibody produced by a hybridoma selected from the group consisting of ECACC 10022401, ECACC 11051801, ECACC 11051802, ECACC 11051803 and ECACC 11051804 or a functional variant of said antibody.

In a particular embodiment, the levels of S100A4 protein are quantified by means of Western blot, immunohistochemistry or ELISA.

Other Aspects of the Invention

The present invention further provides the use of an antibody or fragment thereof or a monoclonal antibody according to any one of the embodiments presented herein, as a marker for the identification, location, assessment, diagnosis, prognosis, or monitoring of a tumor or any other S100A4 mediated diseases in a subject.

The present invention further provides a product containing an antibody or fragment thereof or a monoclonal antibody according to any one of the embodiments presented herein, and an anti-cancer agent, as a combined preparation for simultaneous, separate or sequential use in the treatment of tumors.

The present invention further provides a product containing an antibody or fragment thereof or a monoclonal antibody according to any one of the embodiments presented herein, and a therapeutic agent, as a combined preparation for simultaneous, separate or sequential use in the treatment of S100A4 mediated diseases.

An antibody or fragment thereof that specifically binds a human or murine S100A4 polypeptide for use as a medicament for the treatment of tumors.

Definitions

The terms "S100A4", "S100A4 protein", "S100 calcium-binding protein A4", "calcium protein", "calvasculin", "metastasin", "murine placental homolog", "MTS1", "CAPL", "p9Ka", "18A2", "pEL98", "42A", "FSP1", "fibroblast-specific protein-1", "malignant transformation suppression 1", "leukemia multidrug resistance associated protein", "OTTHUMP00000015469", OTTHUMP00000032895", are used interchangeably, and include as well variants, isoforms, species homologs of human or murine S100A4, and analogs having at least one common epitope with human or murine S100A4.

The complete cDNA sequence for human S100A4 has the Genbank accession number M80563 (31 Oct. 1994).

The complete cDNA sequence for murine S100A4 has the Genbank accession number D00208 (5 Dec. 1997).

The complete protein sequence for human S100A4 has the UniProt accession number P26447 (Aug. 1, 1992):

```
                                                  SEQ ID NO: 21
MACPLEKALDVMVSTFHKYSGKEGDKFKLNKSELKELLTRELPSFLGKRT

DEAAFQKLMSNLDSNRDNEVDFQEYCVFLSCIAMMCNEFFEGFPDKQPRK

K
```

The complete protein sequence for murine S100A4 has the UniProt accession number P07091 (Apr. 1, 1988).

The term "antibody" is used herein in the broadest sense and covers monoclonal antibodies (including full length monoclonal antibodies), polyclonal antibodies, multispecific antibodies (e.g. bispecific antibodies), and antibody fragments so long as they exhibit the desired biological activity.

An intact "antibody" includes heteromultimeric glycoproteins comprising at least two heavy (H) chains and two light (L) chains inter-connected by disulfide bonds. Typically, each light chain is linked to a heavy chain by one covalent disulfide bond while the number of disulfide linkages between the heavy chains of different immunoglobulin isotypes varies. Each heavy and light chain also has intrachain disulfide bridges. Each heavy chain has at one end a heavy chain variable region (abbreviated herein as HCVR or VH) followed by a heavy chain constant region. The heavy chain constant region is comprised of three domains, CH1, CH2, and CH3. Each light chain has a light chain variable region (abbreviated herein as LCVR or VL) and a light chain constant region at its other end. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions are not directly involved in the binding of the antibody to the antigen but exhibit various effector functions such as participation in antibody dependent cell-mediated cytotoxicity (ADCC), phagocytosis via binding to Fcγ receptor, half-life/clearance rate via neonatal Fc receptor (FcRn) and complement dependent cytotoxicity via the C1q component of the complement cascade.

The term "fragment" when referring to an antibody, means antigen binding fragments of an antibody comprising a partial heavy or light chain variable sequence, which retain capacity to bind human or murine S100A4. Examples of fragments include, without being limited to, (i) a Fab fragment, a monovalent fragment consisting of the VL, VH, CL, and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (Ward et al., (1989) *Nature* 341:544-546), which consists of a VH domain; and (vi) an isolated complementarity determining region (CDR). Fragments can be prepared by recombinant techniques or enzymatic or chemical cleavage of intact antibodies, e.g. papain digestion (see for example, WO94/29348).

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al. (1988) *Science* 242:423-426; and Huston et al. (1988) *Proc. Natl. Acad. Sci. USA* 85:5879-5883). Such single chain antibodies are included by reference to the term "antibody".

The term "monoclonal antibody" refers to a preparation of antibody molecules of homogeneous molecular composition i.e. the individual antibodies comprising the population are identical except for possible naturally occurring mutations that may be present in minor amounts. A monoclonal antibody composition displays a single binding specificity and affinity for a particular epitope or antigenic binding site. The monoclonal antibodies are produced by a hybrid cell product of the fusion of a B-cell clone descendent of a single unique parent cell and a tumor plasma cell. Furthermore, in contrast to polyclonal antibody preparations that typically include different antibodies directed against different determinants (epitopes), each monoclonal antibody is directed against a single determinant on the antigen.

The term "diclonal antibody" refers to a preparation of at least two antibodies to murine or human S100A4. Typically, the different antibodies bind different epitopes.

The term "oligoclonal antibody" refers to a preparation of 3 to 100 different antibodies to murine or human S100A4. Typically, the antibodies in such a preparation bind to a range of different epitopes.

The term "polyclonal antibody" refers to a preparation of more than 1 (two or more) different antibodies to murine or human S100A4 derived from different B-cell lines, i.e., antibodies which are a mixture of immunoglobulins, secreted against a specific antigen (S100A4). Such a preparation includes antibodies binding to a range of different epitopes.

The term "bispecific antibody" refers to that antibody having two different binding specificities, see. e.g., U.S. Pat. Nos. 5,922,845 and 5,837,243; Zeilder (1999) J. Immunol. 163: 1246-1252; Somasundaram (1999) Hum. Antibodies 9:47-54; Keler (1997) Cancer Res. 57:4008-4014. For example, a bispecific antibody may have one binding site for a cell surface antigen, and a second binding site for an Fc receptor on the surface of an effector cell. The exemplary bispecific antibodies can bind to two different epitopes of the B-cell surface marker. Others of the said antibodies can bind to a first B-cell marker and additionally bind to a second B-cell surface marker. Alternatively, a binding arm of an anti-B cell marker can be combined with an arm which binds to a triggering molecule in a leukocyte, such as a T-cell receptor molecule (for example, CD2 or CD3), or Fc receptors for IgG (FcγR), such as FcγRI (CD64), FcγRII (CD32) and FcγRIII (CD 16), such that the mechanisms of cell defense are concentrated in the B-cell. Bispecific antibodies can also be used to locate cytotoxic agents against the B-cell. These antibodies have a binding arm to the marker of the lymphocyte and an arm which binds to the cytotoxic agent (for example, saporin, anti-interferon-α, vinca alkaloid, ricin A-chain, methotrexate or a radioactive hapten isotope). Bispecific antibodies can be prepared as whole antibodies or as antibody fragments (for example, F(ab)2 bispecific antibodies).

Bispecific antibodies further include diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (See, e.g., Holliger, P., et al. (1993) *Proc. Natl. Acad. Sci. USA* 90:6444-6448; Poljak, R J., et al. (1994) Structure 2:1121-1123).

The term "multispecific antibody" refers to that antibody having at least three binding sites or specificities.

The term "epitope" refers to a protein determinant capable of specific binding to an antibody, or the place where an antibody binds its Ag, or by extension to the peptide presented in an MHC molecule to which a T-cell receptor binds. Epitopes consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The term "isolated" means identified and separated or removed from its natural environment. For example, a polynucleotide or a polypeptide naturally present in a living organism is not "isolated," but the same polynucleotide or polypeptide separated from the coexisting materials of its natural state is "isolated," including but not limited to when such polynucleotide or polypeptide is introduced back into a cell, even if the cell is of the same species or type as that from which the polynucleotide or polypeptide was separated.

The phrase "an agent effective to induce an immune response against an antigen" refers to a different substance than the monoclonal antibody of the present invention that acts as a stimulator of immune responses thereby increasing the response to the vaccine, without having any specific antigenic effect in itself. This agent is also known in the art as an adjuvant. Examples include lipid A, *Bordetella pertussis* or *Mycobacterium tuberculosis* derived proteins, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2,-7, or -12, may also be used as adjuvants.

The phrase "specifically binds" when referring to antibodies and antigen binding fragments thereof means that the antibody binds murine or human S100A4 with no or insignificant binding to other murine or human proteins. The term however does not exclude the fact that antibodies of the invention may also be cross-reactive with other forms of S100A4.

The phrase "specifically binds" to a binding reaction that is determinative of the presence of the protein in a heterogeneous population of proteins and other biologics. Typically, the antibody binds with an association constant ($K_a$) of at least about $1 \times 10^6$ $M^{-1}$ or $10^7$ $M^{-1}$, or about $10^8$ $M^{-1}$ to $10^9$ $M^{-1}$, or about $10^{10}$ $M^{-1}$ to $10^{11}$ $M^{-1}$ or higher, and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

The phrase "specifically bind(s)" or "bind(s) specifically" when referring to a peptide refers to a peptide molecule which has intermediate or high binding affinity, exclusively or predominately, to a target molecule. The phrase "specifically binds to" refers to a binding reaction that is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions may require a binding moiety that is selected for its specificity for a particular target antigen. A variety of assay formats may be used to select ligands that are specifically reactive with a particular protein. For example, solid-phase ELISA immunoassays, immunoprecipitation, Biacore, and Western blot are used to identify peptides that specifically react with HUMAN or murine S100A4. Typically a specific or selective reaction will be at least twice background signal or noise and more typically more than 10 times background.

The term "blocks" as used throughout the present specification in relation to antibodies and antigen binding fragments thereof of the invention means that the biological activity of human or murine S100A4 is reduced in the presence of the antibodies and antigen binding fragments thereof of the present invention in comparison to the activity of human or murine S100A4 in the absence of such antibodies and antigen binding fragments thereof. Blocking may be due to but not limited to one or more of neutralizing ligand binding, preventing the ligand activating the receptor, down regulating the human or murine S100A4 or affecting effector functionality. Levels of blockade can be measured in several ways, for example by use of the assays as set out in the examples below, proteolytic activity, cell migration, tumor development, tumor angiogenesis and tumor dissemination (metastasis).

If an antibody or antigen binding fragment thereof is capable of blocking then this is indicative of inhibition of the interaction between murine or human S100A4 binding protein and its receptor.

The phrase "a mechanism of action of a human or murine S100A4 protein" refers to each of the intracellular and extracellular functions of the S100A4 protein. The intracellular functions of S100A4 protein include those of interfering with vital cellular functions such as cell motility, invasion, cell division, and survival (Kriajevska M V et al. J Biol Chem 1994. 269(31):19679-82 and Grigorian M et al. J Biol Chem 2001. 276(25):22699-708); binding to several intracellular target proteins and modulating their function, such us to the heavy chain of non-muscle myosin II (Kriajevska M V et al. J Biol Chem 1994. 269(31):19679-82 and Ford H L et al. Oncogene 1995. 10(8):1597-1605); and Liprinβ1(Kriajevska M et al. J Biol Chem 2002. 277(7):5229-35); interacting with the tumor suppressor protein p53 and regulating its transactivational function, thereby differentially modulating p53-target genes expression in a cell-specific manner (Grigorian M et al. J Biol Chem 2001. 276(25):22699-708). The extracellular functions of S100A4 protein include those of cell-specific modulator of tumor cell motility, survival, and apoptosis; acting as an angiogenic factor (Ambartsumian N et al. Oncogene 2001. 20(34):4685-95; Pedersen M V et al. J Neurosci Res 2004. 77(6):777-86; Belot N et al. Biochim Biophys Acta 2002. 1600(1-2):74-83 and Pedersen K B et al. BMC Cancer 2004. 19; 452); metastasis-promoter; enhancer of the blood vessel network of tumors; stimulator of neovascularisation; increasing endothelial cell motility; remodeling tumor cell cytoskeleton; promoting cell motility and adhesion; facilitating the degradation of extracellular matrix via induction of proteolytically active MMPs. Extracellular S100A4 functions also include those of targeting tumor endothelial cells, by binding to the receptor RAGE and triggering a cascade of events either through signal transduction or internalization followed by interaction with the intracellular target proteins (p53, non-muscle myosin and others). As a result, tumor cells acquire a more progressed metastatic phenotype activity. Additional extracellular S100A4 functions include targeting of endothelial cells thereby stimulating their motility, enhancing tumor angiogenesis, and therefore providing routes for metastatic dissemination (Schmidt-Hansen B et al. J Biol Chem 2004. 279(23):24498-504).

The term "high affinity" for an IgG antibody refers to an equilibrium association constant ($K_a$) of at least about $10^7 M^{-1}$, at least about $10^8 M^{-1}$, at least about $10^9 M^{-1}$, at least about $10^{10}$ $M^{-1}$, at least about $10^{11}$ $M^{-1}$, or at least about $10^{12} M^{-1}$ or greater, e.g., up to $10^{13} M^{-1}$ or $10^{14} M^{-1}$ or greater. However, "high affinity" binding can vary for other antibody isotypes.

The term "$K_a$", as used herein, is intended to refer to the equilibrium association constant of a particular antibody-antigen interaction. This constant has units of 1/M.

The term "$K_d$", as used herein, is intended to refer to the equilibrium dissociation constant of a particular antibody-antigen interaction. This constant has units of M.

The term "$k_a$", as used herein, is intended to refer to the kinetic association constant of a particular antibody-antigen interaction. This constant has units of 1/Ms.

The term "$k_d$", as used herein, is intended to refer to the kinetic dissociation constant of a particular antibody-antigen interaction. This constant has units of 1/s.

The phrase "particular antibody-antigen interactions" refers to the experimental conditions under which the equilibrium and kinetic constants are measured.

The phrase "particular antibody-antigen interactions" refers to the experimental conditions under which the equilibrium and kinetic constants are measured.

The term "isotype" refers to the antibody class (e.g., IgM or IgG1) that is encoded by heavy chain constant region genes.

The term "nucleic acid" or "polynucleotide" is intended to include DNA molecules and RNA molecules. A nucleic acid can be single-stranded or double-stranded.

The term "isolated nucleic acid" or "isolated polynucleotide" in reference to nucleic acids encoding antibodies or antibody fragments thereof (e.g., VR, VL, CDR3) that bind to human or murine S100A4, is intended to refer to a nucleic acid in which the nucleotide sequences encoding the antibody or antibody portion are free of other nucleotide sequences encoding antibodies or antibody portions that bind antigens other than human or murine S100A4, which other sequences may naturally flank the nucleic acid in human genomic DNA.

The term "stability" as used in relation to antibodies and fragments thereof refers to the activity of the antibody or antigen binding fragment when determined by direct binding ELISA is comparable 12 days after incubation in serum to the $EC_{50}$ starting values at −20° C., 4° C., or 37° C.

The term "human antibody" includes antibodies having variable and constant regions (if present) derived from human germline immunoglobulin sequences. The human sequence antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences (i.e., humanized antibodies).

The term "chimeric antibody" refers to a type of engineered antibody which contains a naturally-occurring variable domain (light chain and heavy chains) derived from a donor antibody in association with light and heavy chain constant regions derived from an acceptor antibody.

The term "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl. Acad Sci USA, 86:10029-10032 (1989), Hodgson et al., Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanised antibodies—see for example EP-A-0239400 and EP-A-054951.

The term "donor antibody" refers to an antibody (monoclonal, and/or recombinant) that contributes the amino acid sequences of its variable domains, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but preferably all) of the amino acid sequences encoding its heavy and/or light chain framework regions and/or its heavy and/or light chain constant regions to the first immunoglobulin partner. The human antibody is the acceptor antibody.

The acronym "CDRs" refers to the complementarity determining region amino acid sequences of an antibody which are the hypervariable domains of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable domains; Nature 342, p877-883. CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

Throughout this specification, amino acid residues in antibody sequences are numbered according to the Kabat scheme. Similarly, the terms "CDR", "CDRL1", "CDRL2", "CDRL3", "CDRH1", "CDRH2", "CDRH3" follow the Kabat numbering system as set forth in Kabat et al; Sequences of proteins of Immunological Interest NIH, 1987. It will be apparent to those skilled in the art that there are alternative definitions of CDR sequences such as for example those set out in Chothia et al. (1989).

It will be apparent to those skilled in the art that the term "derived" is intended to define not only the source in the sense of it being the physical origin for the material but also to define material which is structurally identical (in terms of primary amino acid sequence) to the material but which does not originate from the reference source. Thus, for example, "residues found in the donor antibody from which CDRH3 is derived" need not necessarily have been purified from the donor antibody.

The terms "VH" and "VL" refer to the heavy chain variable domain and light chain variable domain respectively of an antibody.

The term "effector function" as used herein is meant to refer to one or more of Antibody dependant cell mediated cytotoxic activity (ADCC) and complement dependant cytotoxic activity (CDC) mediated responses, Fc-mediated phagocytosis and antibody recycling via the FcRn receptor. The interaction between the constant region of an antibody and various Fc receptors (FcR) is believed to mediate the effector functions of the antibody. Significant biological effects can be a consequence of effector functionality, in particular, antibody-dependent cellular cytotoxicity (ADCC), fixation of complement (complement dependent cytotoxicity or CDC), phagocytosis (antibody-dependent cell-mediated phagocytosis or ADCP) and halflife/clearance of the antibody. Usually, the ability to mediate effector function requires binding of the antibody to an antigen and not all antibodies will mediate every effector function. Effector function can be measured in a number of ways including for example via binding of the FcyRlll to Natural Killer cells or via FcyRI to monocytes/macrophages to measure for ADCC effector function.

Various modifications to the heavy chain constant region of antibodies may be carried out depending on the desired effector property. Human constant regions which essentially lack the functions of a) activation of complement by the classical pathway; and b) mediating antibody-dependent cellular cytotoxicity include the IgG4 constant region and the IgG2 constant region. IgG1 constant regions containing specific mutations have separately been described to reduce binding to Fc receptors and therefore reduce ADCC and CDC (Duncan et al. Nature 1988, 332; 563-564; Lund et al. J. Immunol. 1991, 147; 2657-2662; Chappel et al. PNAS 1991, 88; 9036-9040; Burton and Woof, Adv. Immunol. 1992, 51; 1-84; Morgan et al., Immunology 1995, 86; 319-324; Hezareh et al., J. Virol. 2001, 75 (24); 12161-12168). Human IgG1 constant regions containing specific mutations or altered glycosylation on residue Asn297 have also been described to enhance binding to Fc receptors. These have also been shown to enhance ADCC and CDC, in some cases (Lazar et al. PNAS 2006, 103; 4005-4010; Shields et al. J Biol Chem 2001, 276; 6591-6604; Nechansky et al. Mollmmunol, 2007, 44; 1815-1817).

For IgG antibodies, effector functionalities including ADCC and ADCP are mediated by the interaction of the heavy chain constant region with a family of Fcγ receptors present on the surface of immune cells. In humans these include FcγRI (CD64), FcγRII (CD32) and FcγRIII (CD16). Interaction between the antibody bound to antigen and the formation of the Fc/Fcγ complex induces a range of effects including cytotoxicity, immune cell activation, phagocytosis and release of inflammatory cytokines. Specific substitutions in the constant region (including S239D/1332E) are known to increase the affinity of the heavy chain constant region for certain Fc receptors, thus enhancing the effector functionality of the antibody (Lazar et al. PNAS 2006).

The term "homology" or "sequence homology" refers to the degree of similarity between sequences, that is due to their shared ancestry. There exists various sequence database similarity search tools known by the skilled in the art, such as FASTA, BLAST, to calculate homologies.

The term "identity" or "sequence identity" means, for polynucleotides and polypeptides, as the case may be, the comparison calculated using an algorithm provided in (1) and (2) below:

(1) Identity for polynucleotides is calculated by multiplying the total number of nucleotides in a given sequence by the integer defining the percent identity divided by 100 and then subtracting that product from said total number of nucleotides in said sequence, or:

$$nn \leq xn - (xn \cdot y),$$

wherein nn is the number of nucleotide alterations, xn is the total number of nucleotides in a given sequence, y is 0.95 for 95%, 0.97 for 97% or 1.00 for 100%, and · is the symbol for the multiplication operator, and wherein any non-integer product of xn and y is rounded down to the nearest integer prior to subtracting it from xn. Alterations of a polynucleotide sequence encoding a polypeptide may create nonsense, missense or frameshift mutations in this coding sequence and thereby alter the polypeptide encoded by the polynucleotide following such alterations.

(2) Identity for polypeptides is calculated by multiplying the total number of amino acids by the integer defining the percent identity divided by 100 and then subtracting that product from said total number of amino acids, or:

$$na \leq xa - (xa \cdot y),$$

wherein na is the number of amino acid alterations, xa is the total number of amino acids in the sequence, y is 0.95 for 95%, 0.97 for 97% or 1.00 for 100%, and · is the symbol for the multiplication operator, and wherein any non-integer product of xa and y is rounded down to the nearest integer prior to subtracting it from xa.

The term "variant(s)" refers to a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant mayor may not alter the amino acid sequence of a polypeptide encoded by the reference polynucleotide. Nucleotide changes may result in amino acid substitutions, additions, deletions, fusion proteins and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue mayor may not be one encoded by the genetic code. It is well recognized in the art that certain amino acid substitutions are regarded as being "conservative". Amino acids are divided into groups based on common side-chain properties and substitutions within groups that maintain all or substantially all of the binding affinity of the antibody of the invention or antigen binding fragment thereof are regarded as conservative substitutions, see table below:

| Side chain | Members |
| --- | --- |
| hydrophobic | Met, Ala, Val, Leu, Ile |
| neutral hydrophilic | Cys, Ser, Thr |
| acidic | Asp, Glu |
| basic | Asn, Gln, His, Lys, Arg |
| residues that influence chain orientation | Gly, Pro |
| aromatic | Trp, Tyr, Phe |

In some aspects of the invention variants in which several, for example 5-10, 1-5, 1-3, 1-2 amino acid residues or 1 amino acid residue are substituted, deleted, or added in any combination may be included. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

Production of Chimeric and Humanized Antibodies

The use of intact non-human antibodies in the treatment of human diseases or disorders carries with it the potential for the now well established problems of immunogenicity, that is the immune system of the patient may recognise the non-human intact antibody as non-self and mount a neutralizing response. This is particularly evident upon multiple administration of the non-human antibody to a human patient. Various techniques have been developed over the years to overcome these problems and generally involve reducing the composition of non-human amino acid sequences in the intact antibody whilst retaining the relative ease in obtaining non-human antibodies from an immunised animal e.g. mouse, rat or rabbit. Broadly two approaches have been used to achieve this. The first are chimeric antibodies, which generally comprise a non-human (e.g. rodent such as mouse) variable domain fused to a human constant region. Because the antigen-binding site of an antibody is localised within the variable domains the chimeric antibody retains its binding affinity for the antigen but acquires the effector functions of the human constant region and are therefore able to perform effector functions such as described supra. Chimeric antibodies are typically produced using recombinant DNA methods. DNA encoding the antibodies (e.g. cDNA) is isolated and sequenced using conventional procedures (e.g. by using oligonucleotide probes that are capable of binding specifically to genes encoding the H and L chains of the antibody of the invention. Hybridoma cells serve as a typical source of such DNA. Once isolated, the DNA is placed into expression vectors which are then transfected into host cells such as E. Coli, COS cells, CHO cells or myeloma cells that do not otherwise produce immunoglobulin protein to obtain synthesis of the antibody. The DNA may be modified by substituting the coding sequence for human L and H chains for the corresponding non-human (e.g. murine) H and L constant regions, see e.g. Morrison; PNAS 81, 6851 (1984).

The second approach involves the generation of humanized antibodies wherein the non-human content of the antibody is reduced by humanizing the variable domains. Two techniques for humanization have gained popularity. The first is humanization by CDR grafting. CDRs build loops close to the antibody's N-terminus where they form a surface mounted in a scaffold provided by the framework regions. Antigen-binding specificity of the antibody is mainly defined by the topography and by the chemical characteristics of its CDR surface. These features are in turn determined by the conformation of the individual CDRs, by the relative disposition of the CDRs, and by the nature and disposition of the side chains of the residues comprising the CDRs. A large decrease in immunogenicity can be achieved by grafting only the CDRs of non-human (e.g. murine) antibodies ("donor" antibodies) onto human framework ("acceptor framework") and constant regions (see Jones et al (1986) Nature 321, 522-525 and Verhoeyen M et al (1988) Science 239, 1534-1536). However, CDR grafting per se may not result in the complete retention of antigen-binding properties and it is frequently found that some framework residues (sometimes referred to as "back mutations") of the donor antibody need to be preserved in the humanized molecule if significant antigen-binding affinity is to be recovered (see Queen C et al (1989) PNAS 86, 10029-10033, Co, M et al (1991) Nature 351, 501-502). In this case, human variable domains showing the greatest sequence homology to the non-human donor antibody are chosen from a database in order to provide the human framework (FR). The selection of human FRs can be made either from human consensus or individual human antibodies. Where needed, key residues from the donor antibody are substituted into the human acceptor framework to preserve CDR conformations. Computer modeling of the antibody maybe used to help identify such structurally important residues, see WO99/48523.

Alternatively, humanization maybe achieved by a process of "veneering". A statistical analysis of unique human and murine immunoglobulin heavy and light chain variable domains revealed that the precise patterns of exposed residues are different in human and murine antibodies, and most individual surface positions have a strong preference for a small number of different residues (see Padlan E. A. et al; (1991) Mol. Immunol. 28, 489-498 and Pedersen J. T. et al (1994) J. Mol. Biol. 235; 959-973).

Therefore it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable domain "invisible" to the human immune system (see also Mark G. E. et al (1994) in Handbook of Experimental Pharmacology vol. 113: The pharmacology of monoclonal Antibodies, Springer-Verlag, pp 105-134). This procedure of humanization is referred to as "veneering" because only the surface of the antibody is altered, the supporting residues remain undisturbed.

Production of Human Antibodies

The monoclonal antibodies (mAbs) of the invention can be produced by a variety of techniques, including conventional monoclonal antibody methodology e.g., the standard somatic cell hybridization technique of Kohler and Milstein, *Nature* 256: 495 (1975). Any technique for producing monoclonal antibody can be employed e.g., viral or oncogenic transformation of B lymphocytes. One animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known (see, e.g., Harlow and Lane (1988), *Antibodies, A Laboratory Manual*, Cold Spring Harbor Laboratory Press, Cold Spring Harbor N.Y.).

Human monoclonal antibodies directed against murine or human S100A4 can be generated using transgenic mice carrying a human immune system rather than the mouse system. Several strains of transgenic mice are now available wherein their mouse immunoglobulin loci has been replaced with human immunoglobulin gene segments (see Tomizuka K, (2000) PNAS 97, 722-727; Fishwild D. M (1996) Nature Biotechnol. 14, 845-851, Mendez M J, 1997, Nature Genetics, 15, 146-156). Upon antigen challenge such mice are capable of producing a repertoire of human antibodies from which antibodies of interest can be selected. Of particular note is the Trimera™ system (see Eren R et al, (1998) Immunology 93:154-161) where human lymphocytes are transplanted into irradiated mice, the Selected Lymphocyte Antibody System (SLAM, see Babcook et al, PNAS (1996) 93:7843-7848) where human (or other species) lymphocytes are effectively put through a massive pooled in vitro antibody generation procedure followed by deconvulated, limiting dilution and selection procedure and the Xenomouse II™ (Abgenix Inc). An alternative approach is available from Morphotek Inc using the Morphodoma™ technology.

Detailed procedures to generate fully human monoclonal antibodies to human or murine S100A4 are described in the Examples below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA, and mice with sufficient titers of anti-S100A4 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen.

To purify human anti-S100A4 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected human anti-S100A4 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using human or murine S100A4 coated-ELISA plates. Biotinylated MAb binding can be detected with a strep-avidin-alkaline phosphatase probe.

To determine the isotype of purified antibodies, isotype ELISAs can be performed. Wells of microtiter plates can be coated with 1 µg/ml of anti-human IgG overnight at 4° C. After blocking with 1% BSA, the plates are reacted with 1 µg/ml or less of monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

To demonstrate binding of monoclonal antibodies to live cells expressing the human or murine S100A4, flow cytometry can be used. Briefly, cell lines expressing human or murine S100A4 (grown under standard growth conditions) are mixed with various concentrations of monoclonal antibodies in PBS containing 0.1% BSA and 10% fetal calf serum, and incubated at 37° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-S100A4 human IgGs can be further tested for reactivity with human or murine S100A4 antigen by Western blotting. Briefly, cell extracts from cells expressing human or murine S100A4 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Phage display technology can be used to produce human antibodies (and fragments thereof), see McCafferty; Nature, 348, 552-553 (1990) and Griffiths A D et al (1994) EMBO 13:3245-3260. According to this technique antibody variable domain genes are cloned in frame into either a major or minor coat of protein gene of a filamentous bacteriophage such as M13 or fd and displayed (usually with the aid of a helper phage) as functional antigen binding fragments thereof on the surface of the phage particle. Selections based on the functional properties of the antibody result in selection of the gene encoding the antibody exhibiting those properties. The phage display technique can be used to select antigen specific antibodies from libraries made from human B cells taken from individuals afflicted with a disease or disorder described above or alternatively from unimmunized human donors (see Marks; J. Mol. Bio. 222, 581-597, 1991). Where an intact human antibody is desired comprising a constant domain it is necessary to redone the phage displayed derived fragment into a mammalian expression vectors comprising the desired constant regions and establishing stable expressing cell lines.

The technique of affinity maturation (Marks; Bio/technol 10, 779-783 (1992)) may be used to improve binding affinity wherein the affinity of the primary human antibody is improved by sequentially replacing the H and L chain variable domains with naturally occurring variants and selecting on the basis of improved binding affinities. Variants of this technique such as "epitope imprinting" are also available: see WO93/06213. See also Waterhouse; Nucl. Acids Res 21, 2265-2266 (1993).

Pharmaceutical Compositions

The present invention provides pharmaceutical compositions comprising one or a combination of monoclonal antibodies or fragments thereof formulated together with a pharmaceutically acceptable carrier. Some compositions include a combination of multiple (e.g., two or more) isolated antibodies or fragments thereof of the invention. In some compositions, each of the antibodies or fragments thereof of the composition is a monoclonal antibody that binds to a distinct, pre-selected epitope of human or murine S100A4.

Regardless of the route of administration selected, the compounds of the present invention, which may be used in a suitable hydrated form, or the pharmaceutical compositions of the present invention, are formulated into pharmaceutically acceptable dosage forms by conventional methods known to those of skill in the art.

For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. Doses for nucleic acids encoding immunogens range from about 10 ng to 1 g, 100 ng to 100 mg, 1 µg to 10 mg, or 30-300 µg DNA per patient. Doses for infectious viral vectors vary from 10-100, or more, virions per dose.

For therapeutic applications, the pharmaceutical compositions are administered to a patient suffering from established disease in an amount sufficient to arrest or inhibit further development or reverse or eliminate the disease, its symptoms or biochemical markers. For prophylactic applications, the pharmaceutical compositions are administered to a patient susceptible or at risk of a disease in an amount sufficient to delay, inhibit or prevent development of the disease, its symptoms and biochemical markers. An amount adequate to accomplish this is defined as a "therapeutically-" or "prophylactically-effective dose." Dosage depends on the disease being treated, the subject's size, the severity of the subject's symptoms, and the particular composition or route of administration selected. Specifically, in treatment of tumors, a "therapeutically effective dosage" can inhibit tumor growth by at least about 20%, or at least about 40%, or at least about 60%, or at least about 80% relative to untreated subjects. The ability of a compound to inhibit cancer can be evaluated in an animal model system predictive of efficacy in human tumors. Alternatively, this property of a composition can be evaluated by examining the ability of the compound to inhibit by conventional assays in vitro. A therapeutically effective amount of a therapeutic compound can decrease tumor size, or otherwise ameliorate symptoms in a subject.

A composition of the present invention can be administered by a variety of methods known in the art. The route and mode of administration vary depending upon the desired results. For the therapeutic compositions, formulations of the present invention include those suitable for oral, nasal, topical (including buccal and sublingual), rectal, vaginal, and parenteral administration. The formulations may be prepared by any methods known in the art of pharmacy, preferably in full compliance with Good Manufacturing Practice (GMP) regulations of the U.S. Food and Drug Administration.

The phrases "parenteral administration" and "administered parenterally" mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Pharmaceutically acceptable carriers include solvents, dispersion media, coatings, antibacterial and antifungal agents, isotonic and absorption delaying agents, and the like that are physiologically compatible. The carrier can be suitable for intravenous, intramuscular, subcutaneous, parenteral, spinal or epidermal administration (e.g., by injection or infusion). Depending on the route of administration, the active compound, i.e., antibody or fragment thereof, bispecific and multispecific molecule, may be coated in a material to protect the compound from the action of acids and other natural conditions that may inactivate the compound.

The active compounds can be prepared with carriers that protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27). When the active compound is suitably protected, as described above, the compound may be orally administered, for example, with an inert diluent or an assimilable edible carrier.

Typical pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile, substantially isotonic, and stable under the conditions of manufacture and storage. They should be fluid to the extent that easy injectability exists, and should be preserved against the contaminating action of microorganisms such as bacteria and fungi. The composition can be formulated as a solution, micro emulsion, liposome, or other ordered structure suitable to high drug concentration. The carrier can be a solvent or dispersion medium containing, for example, water, isotonic buffered saline solution, ethanol, polyol (for example, glycerol, propylene glycol, and liquid polyethylene glycol, and the like), and suitable mixtures thereof, vegetable oils, such as olive oil, and injectable organic esters, such as ethyl oleate. The proper fluidity can be maintained, for example, by the use of a coating such as lecithin, by the maintenance of the required particle size in the case of dispersion and by the use of surfactants. In many cases, it is preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying (lyophilization) that yield a powder of the active ingredient plus any additional desired ingredient from a previously sterile-filtered solution thereof.

These compositions may also contain excipients such as preservatives, wetting agents, anti-oxidants, emulsifying agents, and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Therapeutic compositions can also be administered with medical devices known in the art. For example, in a preferred embodiment, a therapeutic composition of the invention can be administered with a needleless hypodermic injection device, implantable micro-infusion pump for dispensing medication at a controlled rate, and the like.

When the compounds of the present invention are administered as pharmaceuticals, to humans and animals, they can be given alone or as a pharmaceutical composition containing, for example, 0.01 to 99.5% (or 0.1 to 90%) of active ingredient in combination with a pharmaceutically acceptable carrier.

Methods and Uses of the Invention

The monoclonal antibodies and fragments thereof to human or murine S100A4 and derivatives or conjugates thereof, of the present invention have in vitro and in vivo diagnostic and therapeutic utilities. For example, these molecules can be administered to cells in culture, tissues, organs, e.g. in vitro or ex vivo, or in a subject, e.g., in vivo, to treat, prevent, monitor, or diagnose a variety of disorders.

The term "subject" includes human and non-human animals. Non-human animals includes all vertebrates, e.g., mammals and non-mammals, such as primates and non-human primates, sheep, dog, rabbits, rats, mice, cow, chickens, amphibians, and reptiles. Except when noted, the terms "patient" or "subject" are used interchangeably.

The methods can be used to treat any kind of cancer including but being not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In some embodiments, the cancer cells being treated are metastatic. In other embodiments, the cancer cells being treated are resistant to anticancer or antiangiogenic agents.

In particular, the antibodies and fragments thereof of the present invention, may be used for treating tumors, wherein the tumor is selected from the group consisting of: breast carcinoma, prostate carcinoma, lung carcinoma, colorectal carcinoma, pancreatic carcinoma, renal carcinoma, gastric carcinoma, ovarian carcinoma, papillary thyroid carcinoma, melanoma, hepatocellular carcinoma, bladder carcinoma, liposarcoma invasive carcinoma, neuroblastoma, esophageal squamous carcinoma, osteosarcoma, gallbladder carcinoma, oral squamous carcinoma, endometrial carcinoma, medulloblastoma, and any other S100A4 expressing tumor.

In particular, the antibodies and fragments thereof of the present invention may be used for treating nephropathy, reumathoid arthritis, pulmonary hypertension, psoriasis, and any other S100A4 mediated diseases.

Evidence of the role of S100A4 in developing or mediating nephropathy has been provided by Inoue, T., Okada, H., Takenaka, T., Watanabe, Y. & Suzuki, H. 2009 (A case report suggesting the occurrence of epithelial-mesenchymal transition in obstructive nephropathy. *Clin. Exp. Nephrol* 13, 385-388); Yamaguchi, Y. et al. 2009 (Epithelial-mesenchymal transition as a potential explanation for podocyte depletion in diabetic nephropathy. *Am. J. Kidney Dis* 54, 653-664); Le Hir, M., Hegyi, I., Cueni-Loffing, D., Loffing, J. & Kaissling, B. 2005 (Characterization of renal interstitial fibroblast-specific protein 1/S100A4-positive cells in healthy and inflamed rodent kidneys. *Histochem. Cell Biol* 123, 335-346); among others.

Evidence of the role of S100A4 in developing or mediating reumathoid arthritis has been provided by Bo, G. et al. 2009 (Analyses of differential proteome of human synovial fibroblasts obtained from arthritis. *Clin. Rheumatol* 28, 191-199); Oslejsková, L. et al. 2009 (Metastasis-inducing S100A4 protein is associated with the disease activity of rheumatoid arthritis. *Rheumatology* (Oxford) 48, 1590-1594); Masuda, K. et al. 2002 (Molecular profile of synovial fibroblasts in rheumatoid arthritis depends on the stage of proliferation. *Arthritis Res* 4, R8); among others.

Evidence of the role of S100A4 in developing or mediating pulmonary hypertension has been provided by Peng, T. et al. 2009 (Plasma levels of S100A4 in portopulmonary hypertension. *Biomarkers* 14, 156-160); Hodge, S. et al. 2009 (Post-transplant bronchiolitis obliterans syndrome is associated with bronchial epithelial to mesenchymal transition. *Am. J. Transplant* 9, 727-733); Spiekerkoetter, E. et al. 2008 (Reactivation of gammaHV68 induces neointimal lesions in pulmonary arteries of S100A4/Mts1-overexpressing mice in association with degradation of elastin. *Am. J. Physiol. Lung Cell Mol. Physiol.* 294, L276-289); Brisset, A. C. et al. 2007 (Intimal smooth muscle cells of porcine and human coronary artery express S100A4, a marker of the rhomboid phenotype in vitro. *Circ. Res* 100, 1055-1062); Lawrie, A. et al. 2005 (Interdependent serotonin transporter and receptor pathways regulate S100A4/Mts1, a gene associated with pulmonary vascular disease. Circ. Res 97, 227-235); Merklinger, S. L. et al. 2005 (Increased fibulin-5 and elastin in S100A4/Mts1 mice with pulmonary hypertension. *Circ. Res* 97, 596-604); Greenway, S. et al. 2004 (S100A4/Mts1 produces murine pulmonary artery changes resembling plexogenic arteriopathy and is increased in human plexogenic arteriopathy. *Am. J. Pathol* 164, 253-262); among others.

Evidence of the role of S100A4 in developing or mediating psoriasis has been provided by Zibert, J R, Skov, L. Thyssen J P, Jacobsen G K, Grigorian M. 2010 (Significance of the S100A4 protein in psoriasis. J Invest Dermatology. 130(1): 150-60); Eckert R L, Broome A M, Ruse M, Robinson N, Ryan D, Lee K. 2004 (J Invest Dermatol. 123(1): 23-33); among others.

The term "treating" includes the administration of the compounds or agents of the present invention to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

Kits-of-Parts

The present invention further relates to a product containing an antibody or fragment thereof or a monoclonal antibody according to any one of the embodiments presented herein, and an anti-cancer agent as a combined preparation for simultaneous, separate or sequential use in the treatment of tumors.

When antibodies against S100A4 are administered together with another agent, the two can be administered simultaneously, separately, or sequentially. Thus, the antibodies and fragments thereof of the invention can also be administered in combination therapy, i.e., combined with other agents. For example, in treatment of cancer, the combination therapy can include an antibody composition of the present invention with at least one anti-tumor agent or other conventional therapy, such as radiation treatment.

This anti-tumor agent or other conventional therapy include, without being limited to, apoptosis modulating agents, chemotherapeutic antineoplastics, immunotherapeutics, antimicrobials, antivirals, antifungals, anti-inflammatory agents, as well as surgical intervention, and radiotherapy.

A number of suitable anticancer agents are contemplated for combination or co-administration to treat, prevent, or ameliorate any of the aforementioned diseases, maladies, or disorders such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with S100A4; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-.alpha.) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteasome inhibitors: NF-KB modulators; anti-CDK compounds; HDAC inhibitors; and the like.

Apoptosis modulating agents include, without being limited to, radiation (e.g., X-rays, gamma rays, UV); tumor necrosis factor (TNF)-related factors (e.g., TNF family receptor proteins, TNF family ligands, TRAIL, antibodies to TRAILR1 or TRAILR2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as imatinib mesylate); antisense molecules; antibodies (e.g., trastuzumab, rituximab, ibritumomab tiuxetan, and bevacizumab); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, dexamethasone, hydroxychloroquine, oxyphenbutazone, phenylbutazone, prednisolone, prednisone); and cancer chemotherapeutic drugs (e.g., irinotecan, fludarabine, dacarbazine, mitoxantrone, gemtuzumab ozogamicin, etoposide phosphate, cisplatin, carboplatin, oxaliplatin, fluorouracil, doxorubicin, gemcitabine, bortezomib, gefltinib, bevacizumab, or paclitaxel); cellular signaling molecules; ceramides and cytokines; staurosporine, and the like.

Antineoplastic or anti-hyperproliferative agents include alkylating agents, antimetabolites, and natural products (e.g., herbs and other plant and animal derived compounds).

Alkylating agents include, without being limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine; lomustine; semustine; and streptozocin); and 5) triazenes (e.g., dacarbazine; dimethyltriazenoimid-azolecarboxamide).

Antimetabolites include, without being limited to: 1) folic acid analogs (e.g., methotrexate (amethopterin)); 2) pyrimidine analogs (e.g., fluorouracil, floxuridine, and cytarabine (cytosine arabinoside)); and 3) purine analogs (e.g., mercaptopurine, thioguanine, and pentostatin).

Chemotherapeutic agents include, without being limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Other conventional anticancer agents include, without being limited to, adriamycin, 5-fluorouracil, etoposide, camptothecin, actinomycin D, mitomycin C, cisplatin, docetaxel, gemcitabine, carboplatin, oxaliplatin, bortezomib, gefitinib, bevacizumab, demethylating agents, inhibitors of her-2, inhibitors of IGF-IR, vascular endothelial growth factor (VEGF), inhibitors of VEGFR, mTOR inhibitors, mitotic inhibitors, Smad inhibitors and taxanes. These agents can be prepared and used singularly, in combined therapeutic compositions, in kits, or in combination with immunotherapeutic agents, and the like.

Any type of radiation can be administered to a patient, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation).

The present invention is also directed to:

[1]. An isolated amino acid sequence comprising a sequence selected from SEQ ID NO: 1, SEQ ID NO: 2, and SEQ ID NO: 3.

[2]. An antibody or fragment thereof that specifically binds to a polypeptide comprising SEQ ID NO: 3.

[3]. An antibody or fragment thereof that specifically binds a human or murine S100A4 polypeptide produced by immunizing a mammal with a polypeptide comprising SEQ ID NO: 3.

[4]. The antibody or fragment thereof of [2] or [3], wherein the antibody or fragment thereof is selected from a human antibody or a fragment thereof; a humanized antibody or a fragment thereof; a polyclonal antibody or a fragment thereof; a monoclonal antibody or a fragment thereof; a Fab antibody; and a chimeric antibody or a fragment thereof

[5]. A monoclonal antibody wherein said monoclonal antibody comprises a light chain polypeptide comprising SEQ ID NO: 1, or said monoclonal antibody comprises a heavy chain polypeptide comprising SEQ ID NO: 2.

[6]. A monoclonal antibody comprising framework regions (FRs) and complementarity determining regions (CDRs), wherein the monoclonal antibody comprises a light chain comprising SEQ ID NO: 1 and a heavy chain comprising SEQ ID NO: 2.

[7]. The monoclonal antibody of [5] or [6], wherein the monoclonal antibody is selected from a human antibody; a humanized antibody; and a chimeric antibody or a fragment thereof.

[8]. The monoclonal antibody according to [5], [6] or [7], wherein said monoclonal antibody:
  a) reacts only with a human or murine S100A4 protein; or
  b) blocks a mechanism of action of a human or murine S100A4 protein; or c) blocks in vitro or in vivo functional activity of a human or murine S100A4 protein; or
d) blocks a promigratory effect induced by a human or murine S100A4 protein or by a human or murine S100A4 protein combined with vascular endothelial growth factor (VEGF) in endothelial cells; or
e) blocks tumor growth; or
f) blocks tumor development; or
g) blocks tumor angiogenesis; or
h) blocks cellular dissemination and metastatic establishment; or
i) blocks cancer stem cells; or
j) any combination of a) to i) above.

[9]. A monoclonal antibody or fragment thereof comprising SEQ ID NO: 1 and SEQ ID NO: 2, wherein said antibody or fragment is monovalent or bivalent.

[10]. A hybridoma cell line capable of producing the monoclonal antibody according to [5], [6], [7], [8] or [9].

[11]. A monoclonal antibody obtainable by a hybridoma cell line deposited under accession number 10022401 at the European Collection of Cell Cultures (ECACC).

[12]. An isolated polynucleotide wherein said isolated polynucleotide comprises SEQ ID NO: 4 coding for the FRs and CDRs of the light chain of the variable region of a monoclonal antibody, or said isolated polynucleotide comprises SEQ ID NO: 5 coding for the FRs and CDRs of the heavy chain of the variable region of a monoclonal antibody.

[13]. An isolated polynucleotide comprising SEQ ID NO: 6 coding for an epitope region of the human S100A4 protein.

[14]. A method for the manufacture of a monoclonal antibody according to [5], [6], [7], [8], [9] or [11], said method comprising:
(i) immunizing a mouse with purified human or murine S100A4 protein or with purified human or murine S100A4 protein combined with an agent effective to induce an immune response against an antigen;
(ii) producing one or more hybridoma cells;
(iii) selecting one or more cells the supernatants of which:
 a) react only with a human or murine S100A4 protein; or
 b) block a mechanism of action of a human or murine S100A4 protein; or
 c) block in vitro or in vivo functional activity of a human or murine S100A4 protein; or
 d) block a promigratory effect induced by a human or murine S100A4 protein or by a human or murine S100A4 protein combined with VEGF in endothelial cells; or
 e) block tumor growth; or
 f) block tumor development; or
 g) block tumor angiogenesis; or
 h) block cellular dissemination and metastatic establishment; or
 i) blocks cancer stem cells; or
 j) any combination of a) to i) above.
(iv) producing a specific cell line from any one of the selected cells of step iii); and
(v) isolating the monoclonal antibody from said cell line.

[15]. A pharmaceutical composition comprising a monoclonal antibody according to [5], [6], [7], [8], [9] or [11], and a pharmaceutically acceptable carrier.

[16]. The pharmaceutical composition according to [15], further comprising a chemotherapeutic agent.

[17]. The antibody or fragment thereof according to [2], [3] or [4], or the monoclonal antibody according to [5], [6], [7], [8] or [9] or [11], for use as a medicament.

[18]. The antibody or fragment thereof according to [2], [3] or [4], or the monoclonal antibody according to [5], [6], [7], [8], [9] or [11], for use as a medicament for the treatment of tumors.

[19]. Use of an antibody or fragment thereof according to [2], [3] or [4], or a monoclonal antibody according to [5], [6], [7], [8], [9] or [11], for the manufacture of a medicament for the treatment of tumors.

[20]. A method for treating tumors comprising administering to a subject in need of said treatment a pharmaceutically effective amount of the monoclonal antibody according to [5], [6], [7], [8], [9] or [11].

[21]. The antibody or fragment thereof or monoclonal antibody according to [18], the use according to [19], or the method for treating tumors according to [20], wherein the tumor is selected from the group consisting of: breast carcinoma, prostate carcinoma, lung carcinoma, colorectal carcinoma, pancreatic carcinoma, renal carcinoma, gastric carcinoma, ovarian carcinoma, papillary thyroid carcinoma, melanoma, hepatocellular carcinoma, bladder carcinoma, liposarcoma invasive carcinoma, neuroblastoma, esophageal squamous carcinoma, osteosarcoma, gallbladder carcinoma, oral squamous carcinoma, endometrial carcinoma, medulloblastoma, and any other S100A4 mediated tumors.

[22]. Use of an antibody or fragment thereof according to [2], [3] or [4], or a monoclonal antibody according to [5], [6], [7], [8], [9] or [11], as a marker for the identification, location, assessment, diagnosis, prognosis, or monitoring of a tumor or any other S100A4 mediated diseases in a subject.

[23]. A product containing an antibody or fragment thereof according to [2], [3] or [4], or a monoclonal antibody according to [5], [6], [7], [8], [9] or [11], and an anti-cancer agent, as a combined preparation for simultaneous, separate or sequential use in the treatment of tumors.

[24]. An antibody or fragment thereof that specifically binds a human or murine S100A4 polypeptide for use as a medicament for the treatment of tumors.

The invention is described hereinafter by way of the following examples which are to be construed as merely illustrative and not limitative of the invention.

EXAMPLES

Preparation of Recombinant Human S100A4 Protein and Monoclonal Antibody

Example 1

Origin and Preparation of Tumor Cell Lines and Cultures

Human Umbilical Vein Endothelial Cells (HUVECs, Lonza) were cultured on 1% Type B gelatin from bovine skin (Sigma) in Endothelial cell Basal Medium EBM (Lonza), supplemented with hEGF, hydrocortisone, brain bovine extract and gentamicine (EGM, Lonza), and 10% FCS (Invitrogen). HUVECs were used between passages 6-9 and all experiments were carried out at 80-85% of confluence, with the same batch of cells.

Colon adenocarcinoma HCT-116 (ATCC, No.:CCL-247) and pancreatic adenocarcinoma MiaPACA-2 (ECACC, No.: 85062806) cell lines were cultured in DMEM High-glucose (PAA) supplemented with 10% FCS (Invitrogen) plus 2 mM L-glutamine.

Myeloma cells were cultured in RPMI 1640 (PAA) supplemented with 10% FCS (PAA; Australian origin) plus 2 mM GlutaMAX™-I (Invitrogen).

All cells were cultured at 37° C. in a humidified 5% CO2-atmosphere, and were consistently free of mycoplasma as evaluated by EZ-PCR mycoplasma test kit (Biological Industries).

Example 2

Origin and Preparation of Animals

Mice for antibody production (female BALB/cAnNHsd); 6 weeks old) and for tumor models ("nude mice": female athymic (Hsd:Athymic Nude-Foxnlnu; 6-7 weeks old) were from Harlan Laboratories Models, S.L. (Barcelona, Spain). Nude mice were maintained in sterile room in micro-isolator cages, and were given sterilized food and water ad libitum. All manipulations were performed in a laminar flow hood.

Example 3

Obtention of Recombinant Human S100A4 Protein

A fragment encoding the full-length human S100A4 was obtained by RT-PCR from mRNA of the cell line HCT-116, derived from human colon adenocarcinoma. Specific primers used in the PCR were:

```
                                            SEQ ID NO: 22
5'-ACTCACATATGGCGTGCCCTCTGGAGAAGGCCCTGGATGTG-3'
and
                                            SEQ ID NO: 23
5'-ACTCATGAGCTCATCATTTCTTCCTGGGCTGCTTATCTGGGAA-3'
```

S100A4 cDNA was cloned into the NdeI site of bacterial expression vector pET28a(+) (Novagen) and positive clones were selected and confirmed by DNA sequencing. This construct was transformed into *E. coli* Tuner™ (DE3) Competent Cells (Novagen), and the protein was induced with 1 mM isopropyl-D-thiogalacto-pyranoside (IPTG; Sigma) for 6 hours. Then, bacteria were harvested and lysed by sonication in buffer A (100 μg/mL lisozim, 0.5 M NaCl, 10 mM $Na_2HPO_4.2H_2O$, 10 mM $NaH_2PO_4.2H_2O$ and 10 mM imidazole pH 7.5). The lysate was cleared by centrifugation and filtered through a HiTrap™ Chelating affinity column (Amersham). The protein was eluted with buffer B (0.5 M NaCl, 10 mM $Na_2HPO_4.2H_2O$, 10 mM $NaH_2PO_4.2H_2O$ and 300 mM imidazole pH 7.5). In some experiments the histidine tag was cleaved using Thrombin protease (Novagen, recognition sequence is Leu-Val-Pro-Arg-Gly-Ser, cleavage site between Arg and Gly). Therefore, the final full-length recombinant S100A4 protein has an additional Gly-Ser-His at the N-terminus. Following digestion the remaining poly-his chain was removed by HiTrap™ Chelating affinity column (Amersham) using the poly-histidine sequence tag and the purity of the supernatant containing the recombinant S100A4 protein was checked by SDS-12% (w/v) polyacrylamide gel electrophoresis.

Example 4

Obtention of Monoclonal Antibodies Against S100A4

Monoclonal antibody (MAb) fusion, ELISA screening and subcloning were performed using standard technologies. Maintenance, expansion and scale up of cultures were done in a humidified atmosphere (94% air and 6% CO2) at 37° C.

For each monoclonal antibody, five animals were immunized with human recombinant S100A4 according to the following protocol. Fifty micrograms of S100A4 protein diluted in PBS (137 mM NaCl, 2.8 mM KCl, 8.1 mM $Na_2HPO_4$, 1.5 mM $KH_2PO_4$; pH 7.2) was used as an emulsion with Complete Freund's adjuvant (Sigma) for the initial subcutaneous (s.c.) immunization and with Incomplete Freund's adjuvant (Sigma) for subsequent injections at days 19 and 35 (s.c.). Ten days after the third injection, sera were obtained and tested. At day-51 a final boost of 25 μg of S100A4 protein diluted in PBS was given intravenously to the mouse with the highest titer serum.

Fusion was done four days after the last injection. Mabs obtained were derived from one fusion of myeloma cells with spleen cells from the selected mouse at a ratio 1/10 respectively using PEG-1500 (Roche Diagnostics) as fusion inducer. After then, cells were plated in 96 microwell plates in medium containing HAT (Invitrogen) for selection of hybrids.

Hybridoma supernatants were screened for reactivity with recombinant human S100A4 by ELISA. 50 μl of S100A4 protein (3 μg/mL in PBS) was coated on MaxiSorp 96 microwell plates (NUNC) overnight at 4° C. After washing with PBS and blocking (1% skimmed milk in PBS; 1 h; 37° C.), 50 μl of hybridoma supernatants were added to each well and incubated for two hours at 37° C. After washing, at room temperature, five times with calcium-magnesium free PBS-HT (274 mM NaCl, 2.8 mM KCl, 8.1 mM $Na_2HPO_4$, 1.5 mM $KH_2PO_4$, 0.1% Tween-20; pH 7.2), bound immunoglobulins were detected with HRP-conjugated goat anti-mouse IgG/IgM (Jackson ImmunoResearch) using Tetramethylbenzidine 3,3 5,5 (TBM, Sigma) as substrate.

Wells with an optical density greater than three times the plate background were chosen for cloning. Clones corresponding to monoclonal antibody 5C3 (internal code 5C3-1B8-1F4; ECACC 10022401), 1E2 (internal code 1E2-2H4-2G8; ECACC 11051803), 6B9 (internal code 6B9-1E8-2A8; ECACC 11051801), 8B6 (internal code 8B6-2F6-1H9-1H10; ECACC 11051804) and 5A3 (internal code 5A3-4A6-5B6; ECACC 11051802) were selected for in vitro and in vivo analysis and subcloned by limiting dilution. Only those subclones that grew at 0.1 and 0.01 cell per well were considered suitable for expansion and were adapted to DMEM/F12 medium (PAA) and frozen.

For large scale purification, hybridoma cells were cultured in DMEM/F12 containing 10% of Fetal Bovine Serum (PAA, Australian origin) and 2 mM of L-Glutamine (GlutaMAX™-I, Invitrogen) in 175 $cm^2$ culture flask. When cell concentration reached $0.8 \times 10^6$ cells/mL (viability over 85%) the culture medium was removed and the cells were washed twice with DMEM/F12 medium without serum. After then, 50 ml of a medium containing 80% DMEM/F12, 20% CDHybridoma (Invitrogen) and 2 mM of L-Glutamine was added to each flask and incubated for 96 hours. At the end, serum-free medium was collected, centrifuged and frozen until purification.

Six liters of serum free supernatant from the hybridoma was obtained. After filtration, purification was made using a 5 ml HiTrap Protein G HP affinity column (Amersham). Eluted antibody was concentrated and diafiltrated in PBS with Amicon® Ultra-15 centrifugal filter devices with low-binding Ultracel® membranes (30000 NMWL, Millipore). Final conditioned antibodies were quantified at 280 nm.

Example 5

Cross-reactivity Characterization of Monoclonal Antibodies 5C3, 1E2, 6B9, 8B6, 5A3: Monoclonal Antibodies React Only with S100A4

Monoclonal antibodies 5C3, 1E2, 6B9, 8B6 and 5A3 were screened for cross-reaction against other members of the S100 family: recombinant human S100A1, S100A2, S100A6 (Abnova), recombinant human S100A7, S100P (cloned from the MDA-MD-468 breast adenocarcinoma cell line and from the HeLa cervix adenocarcinoma cell line, respectively, at Leitat Biomed Division), and recombinant murine S100A4 (cloned from the NIH/3T3 mouse embryo fibroblast adenocarcinoma cell line at Leitat Biomed Division). The immunoglobulin isotype for monoclonal antibodies against S100A4 were determined using the Mouse immunoglobulin subtyping kit (Sigma).

Antibodies screening by ELISA on purified human S100A4, human S100A1, human S100A2, human S100A6, human S100A7, human S100P, and murine S100A4 revealed that monoclonal antibody 5C3, 1E2, 8B6 and 5A3 reacted with human and murine S100A4 and with the same intensity whereas 6B9 only recognized the human S100A4 (Table 1).

Division) at 1 μg/mL; polyclonal rabbit anti-tubulin (ICN Biomedicals) at 1:5000 dilution; goat anti-mouse (Jackson ImmunoResearch) at 0.04 μg/ml and goat anti-rabbit (Sigma) at 1:25000 dilution, as secondary antibodies.

Figure 1:
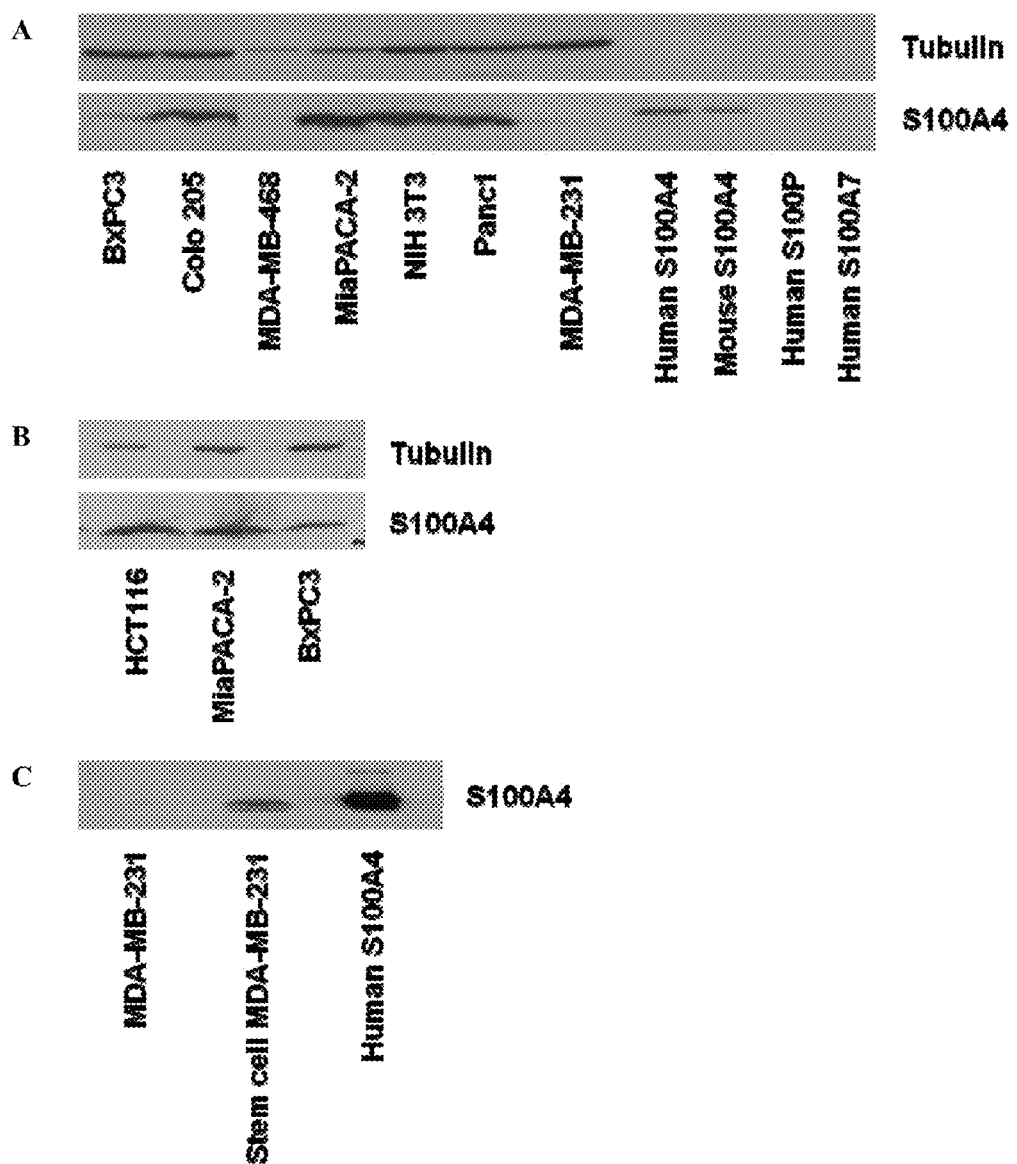
FIG. 1. S100A4 protein expression determined by Western-blot analysis. (A) Levels of S100A4 expression in total extracts from tumor cell lines of different origins and the mouse embryonic fibroblast cell line NIH3T3. (B) Levels of S100A4 expression in total extract from tumor derived HCT116, MiaPACA-2 and BxPC3 xenograft models. (C) Levels of S100A4 expression in total extracts from tumor cell line MDA-MB-231 and cancer stem cells derived from this cell line.

FIG. 1a-1b shows expression pattern of S100A4 protein in several tumor cells lines, in mouse embryonic fibroblast cell line NIH3T3 and tumor samples derived from a HCT116, MiaPACA-2 and BxPC3 cell line xenograft models. Human pancreatic adenocarcinoma cell lines MiaPACA-2 and Panc1 showed higher levels of expression than BxPC3, another human pancreatic adenocarcinoma cell line. As we can see in the FIG. 1b, tumors derived from BxPC3 showed higher levels of expression of S100A4 than own BxPC3 in culture. This increase of the S100A4 levels might indicate a direct role of the protein in the generation of malignant invasive tumors (which is also observed in the immunohistological sections). These increased levels may be produced either by tumor cells themselves or by the tumor stromal cells. Mammary adenocarcinoma cell lines MDA-MB-231 and 468 showed insignificant levels of S100A4 protein, but we can see in FIG. 1c that cancer stem cells derived from a culture of MDA-MB-231 showed elevated levels of S100A4 expression. Colon adenocarcinoma cell line Colo 205 and tumors derived from

TABLE 1

5C3, 1E2, 6B9, 8B6, 5A3 specificity analyzed by ELISA.
Reaction Pattern of mAb in ELISA

| Antibody | Immunogen | Isotype | Human S100A4 | Mouse S100A4 | Human S100A1 | Human S100A2 | Human S100A6 | Human S100A7 | Human S100P |
|---|---|---|---|---|---|---|---|---|---|
| 5C3 | Human S100A4 | IgG1 | ++++ | ++++ | — | — | — | — | — |
| 1E2 | Human S100A4 | IgG2a | ++++ | ++++ | na | na | na | — | — |
| 6B9 | Human S100A4 | IgG1 | ++++ | — | na | na | na | — | — |
| 8B6 | Human S100A4 | IgG1 | ++++ | ++++ | na | na | na | — | — |
| 5A3 | Human S100A4 | IgG1 | ++++ | ++++ | na | na | na | — | — |

++++ positive reaction, — no reaction, na not analized

Example 6

Immune-characterizations of 5C3 by Western-blot

Cell and tumors samples were rinsed twice with PBS and immediately lysed with ice cold Cell Lysis Buffer (150 mM NaCl, 1% IGEPAL CA630, 5 mM EDTA, 100 μg/mL PMSF, 1 mM $Na_3VO_4$, 1 mM NaF and 50 mM Tris pH 7.4). Lysates were cleared by centrifugation and the protein concentration was quantified with the Bradford reagent (Bio-Rad). Total extracts (50 μg) were resolved in a 12% SDS-polyacrilamide gel (PAGE) electrophoresis under reduced conditions and transferred to BioTrace™ PVDF membranes (PALL corporation). Membranes were blocked for 1 hour in TBS plus 0.1% Tween-20 with 5% skimmed dried milk, incubated overnight with the relevant primary antibody and then with the secondary antibodies for 1 hour in blocking buffer, washing three times for 10 min in TBS plus 0.1% Tween-20 after each incubation. Signals were developed using the ECL™ Western Blotting Detection Reagents (Amersham) and exposed to Hyperfilm™ ECL (Amersham).

The concentrations of the antibodies were as follows: monoclonal mouse anti-human S100A4 5C3 (Leitat Biomed HCT116, another colon adenocarcinoma cell line, showed high levels of expression of the protein.

FIG. 1a showed that 5C3 not only react with human S100A4, but also with murine S100A4 (NIH-3T3 mouse fibroblast).

Same results obtained with 5C3 could be extensible also for the others mAbs with exception of the 8B6 that did not react with denaturalized S100A4 protein (data not shown).

Example 7

Immune-characterizations of 5C3 by Immunohistochemistry four micrometer-thick sections from the tumor blocks were deparaffinised, rehydrated in grade alcohols and processed. Briefly, antigen retrieval was performed in a microwave oven for 15 min in 10 mM sodium citrate pH 6.0 with 0.05% Tween-20. Endogenous peroxidase activity was blocked with a 3% $H_2O_2$ solution in distilled water, and the slides were incubated in 5% normal goat serum for 30 min to prevent nonspecific staining. Then, they were incubated overnight at 4° C. with the appropriately diluted primary antibodies. The following antibodies were used: mouse monoclonal antibody 5C3 (1 µg/mL), rabbit polyclonal anti-S100A4 antibody from Dako (dil 1:200) and mouse monoclonal anti-polyhistidine antibody from R&D systems (5 µg/mL). Thereafter the sections were incubated with the appropriately biotinylated goat anti-mouse IgG (H+L) (Vector Laboratories) at 2 µg/mL, and biotinylated goat anti-rabbit IgG (H+L) (Vector Laboratories) at 2 µg/mL, for 60 min and ABC complex (Dako) for 30 min at room temperature. NovaRed (Dako) was used as chromogen. As a negative control, non-related monoclonal antibody (anti-polyhistidine) was substituted for the primary antibody.

Figure 2:
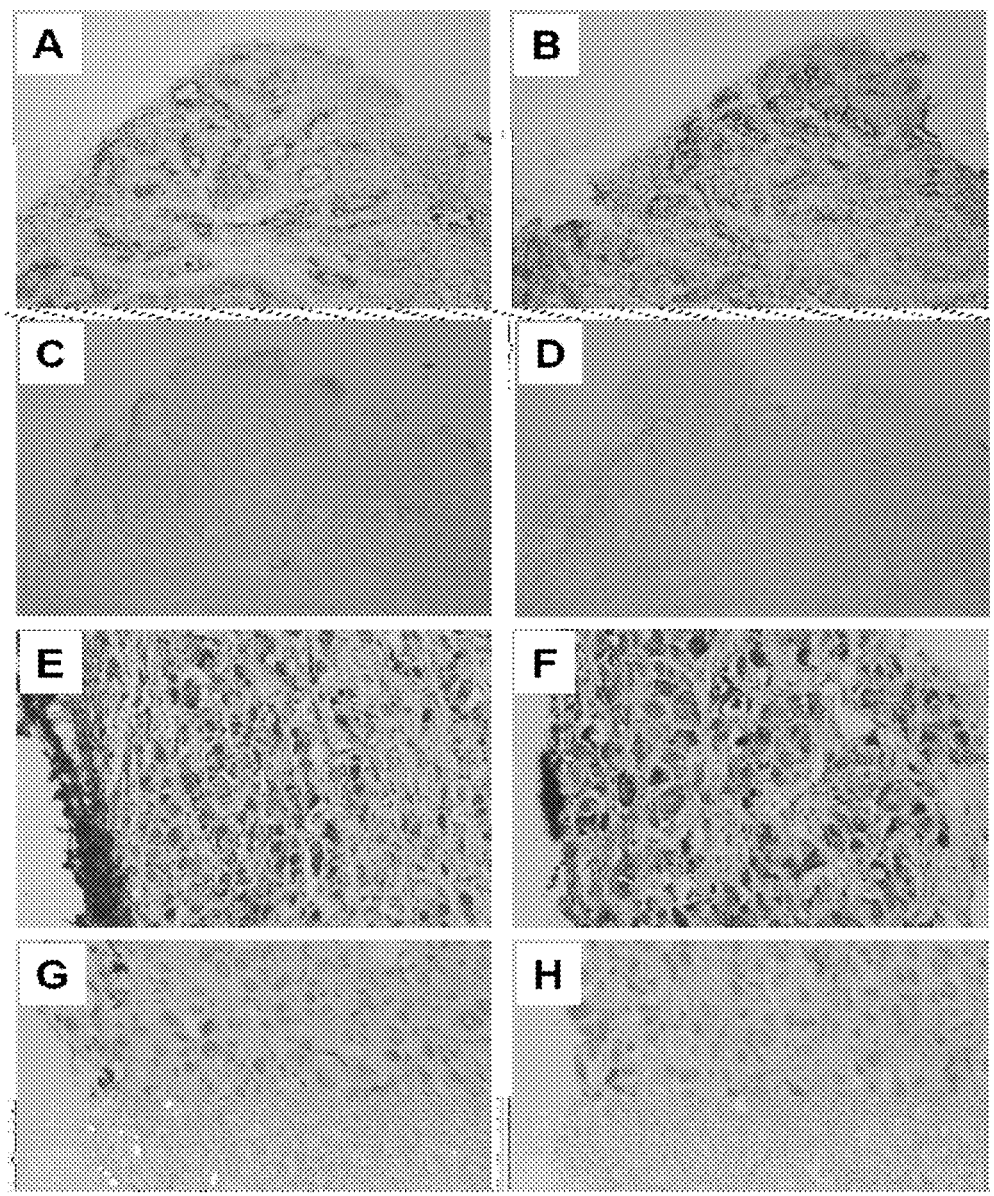
FIG. 2. Immunohistochemical analysis of S100A4 expression. Comparative immunohistochemical analysis of S100A4 expression and distribution, in tumors derived from two pancreatic adenocarcinoma cell lines Panc1 and BxPC3, between 5C3 and the most cited rabbit polyclonal antibody (Dako) against S100A4 used for histology. Images (A-D) were taken at a magnification X 40. Images (E-H) were taken at a magnification X 120 (A) A case showing stronger expression of S100A4 in the invasive fronts than in the center of the tumor in a sample derived from BxPC3 cell line xenograft model, stained with the mouse monoclonal antibody 5C3. (B) A case showing stronger expression of S100A4 in the invasive fronts than in the center of the tumor in a sample derived from BxPC3 cell line xenograft model, stained with a rabbit polyclonal antibody from Dako. (C) Staining with a non-related mouse monoclonal antibody anti-polyhistidine used as a negative control in a tumor derived from BxPC3 cell line xenograft model. (D) Negative control staining without primary antibody in tumor sample derived from BxPC3 cell line xenograft model. (E) Strong expression of S100A4 in the cytoplasm and nuclei of a tumor derived from Panc-1 cell line xenograft model, stained with the mouse monoclonal antibody 5C3. (F) Strong expression of S100A4 in the cytoplasm and nuclei of a tumor derived from Panc-1 cell line xenograft model, stained with a rabbit polyclonal antibody from Dako. (G) Staining with a non-related mouse monoclonal antibody anti-polyhistidine used as a negative control in a tumor derived from Panc-1 cell line xenograft model. (H) Negative control staining without primary antibody in tumor sample derived from Panc-1 cell line xenograft model.

The immunohistochemical analysis (FIG. 2) using the 5C3 monoclonal antibody showed a higher level of S100A4 expression in the invasive front than in the center of the tumor derived from either Panc 1 or BxPC3 pancreatic adenocarcimona xenograft models. Also, analyses at high magnification (×120) showed the presence of the protein not only in the cytoplasm but also in the nuclei of tumor cells. When we used the most cited antibody against S100A4 for immunohistochemistry analysis (rabbit polyclonal antibody from Dako) we observed the same distribution pattern.

Taken together all these results, we affirm that tested monoclonal antibodies can be used as a tool in diagnostic analyses.

Example 8

5C3 Modulates the MMP9 Matrix Metalloproteinase Activity Induced by S100A4

A quantitative protein substrate zymography method is validated as indicator of the destruction of the extracellular matrix, mobilisation of growth factors, processing of surface molecules and is correlated with the migratory and invasive process of stromal and tumor cells. In patients with cancer, this standard laboratory technique appears to reflect a measure of clinical degrees of the disease. Analyses of MMP's activity in serum patients may have diagnostic value for discriminating subgroups of cancer and determinate higher metastatic potentialities.

HUVECs were grown in EBM plus supplements (EGM) and 10% FCS, in 24-well culture plates. Before stimulation, cells were maintained 4 hours in EBM in the absence of serum or other supplements. Then, S100A4 (0.3-1-3 µM), in EBM were added to the culture to analyze their capacity to increase the secretion of active forms of matrix metalloproteinases (MMPs). To test the inhibitory effect of the 5C3 blocking the S100A4 stimulation, 1-2 µM of the antibody were incubated one hour with S100A4 (1 µM), before adding both to the culture. After 24 hours at 37° C., supernatants were centrifuged to remove the debris. Then, 10 µL of Laemmli sample buffer without reducing agent (80 mM Tris-HCl pH 6.8, 4% SDS, 10% glycerol, 0.01% bromophenol blue) was added to 10 µl of each of the clear supernatants that were loaded without boiling in a 8% SDS-polyacrylamide gel copolymerized with Type A gelatine from porcine skin (Sigma) at a final concentration of 1 mg/mL. After electrophoresis, SDS was removed by washing the gel three times for 15 minutes with 2.5% Triton X-100 in $H_2O$. Activation was revealed through 48 hours of incubation of the gel at 37° C. in the presence of 50 mM Tris-HCl pH 7.5, 10 mM $CaCl_2$ and 0.02% $NaN_3$. Staining was performed for 1 hour at RT with 0.1% naphthol amido black (Sigma) in acetic acid, methanol and water at a proportion of 1:3:6 in volume. Then, gels were washed with destaining solution until clear bands were observed over a dark background. Bands were quantified using the NIH ImageJ imaging software.

Figure 3:
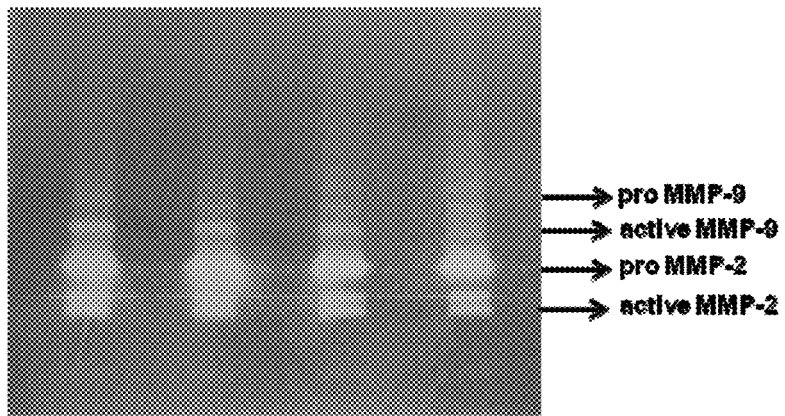
FIG. 3. 5C3 neutralizes the MMP9 proteolytic activity induced by S100A4. Proteolytic activity of MMPs in HUVECs conditioned media. HUVECs were treated with the different stimulus for 24 hours. Supernatants were centrifuged to eliminate the debris and analyzed by gelatin zymography. The clearer band represents MMP9 and MMP2 activity. (A) S100A4 increases the secretion of active forms of MMP9 in a dose-dependent manner. (B) Monoclonal antibody 5C3 neutralized the production of active forms of MMP9 induced by the recombinant S100A4 protein.
Figure 3:
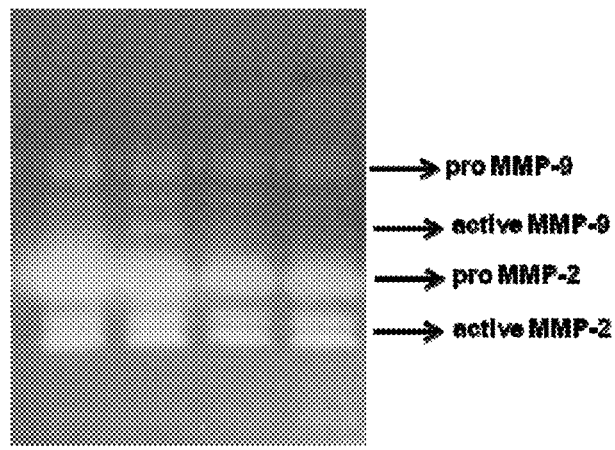

We attempted to determine part of the mechanism of action of S100A4 in the induction of the endothelial cell migration, analyzing the production and activation of MMPs in the conditioned media from HUVECs. The conditioned media from cells treated with S100A4 (0.3-1-3 µM) contained substantially more active forms of MMP9 protein than from non-treated cells. This activity was dose-dependent (FIG. 3A). These differences were detected at 24 h of treatment. The activity of MMP9 in the media was completely reduced when anti-S100A4 antibody 5C3 was added together with the S100A4 protein (FIG. 3B). S100A4 did not induce changes in MMP2 activity in this cellular model.

We can speculate that enhanced proteolytic activity detected in the conditioned media of HUVECs treated with S100A4 is correlated with the stimulation of migration when VEGF plus S100A4 is added to the culture. This should be at least in part be dependent on the activity of MMP9.

Example 9

S100A4 and VEGF Exert a Synergistic Effect on HUVECs Migration and Monoclonal Antibodies 5C3, 1E2, 6B9, 8B6 and 5A3 Block this Activity Endothelial cells (EC) are lining all the vessels of any mammalian organism. EC are the responsible cells to initiate new vessel formation under a specific stimulus that may be originated by a pathologic or a physiologic situation. EC migration is currently accepted as being a key step in such neovasculature formation. Accordingly EC migration studies are fully indicative of the therapeutic activity profile of anti-angiogenic drugs.

Twenty-four-well cell culture plates with light-opaque PET membrane filter inserts with 8 µm-pores (Transwell HTS FluoroBlok™ Multiwell Insert Systems from Becton Dickinson) were used to test the migratory activity. The upper and lower surfaces of the Transwell membranes were coated for 2 hours at 37° C. with 15 µg/mL of Type I Collagen (Upstate). Endothelial cells ($5 \times 10^4$ HUVEC's) suspended in 100 µl of EBM in the absence of serum or other supplements were seeded, after the collagen coating, onto the upper side of each Transwell chamber and incubated for 4 hours at 37° C. Then, S100A4 (1 µM), alone or in combination with VEGF (3 ng/mL) in EBM were added to the lower compartment of the 24-well plates to test their chemotactic capacity. To test the inhibitory effect of the anti-S100A4 (5C3, 1E2, 6B9, 8B6, 5A3) monoclonal antibodies (Leitat Biomed Division), several concentrations (see FIG. 4) of the antibodies were incubated 2 hours with S100A4 and VEGF or VEGF alone, before adding both to the lower chamber of the transwell to initiate migration. Other monoclonal antibody anti-S100A4 called 5H4 (Leitat Biomed Division) was used to compare the activity. After 24 hours at 37° C., cells that had migrated to the lower side of the transwell were incubated with 5 µM Calcein-AM (Calbiochem) for 25-30 minutes at 37° C. Migrated cells were counted under a light microscope at a magnification of ×10. Comparisons between groups were made using the two-tailed nonparametric Mann Whitney U test. Differences for which P value was less than 0.05 were considered statistically significant.

Figure 4:
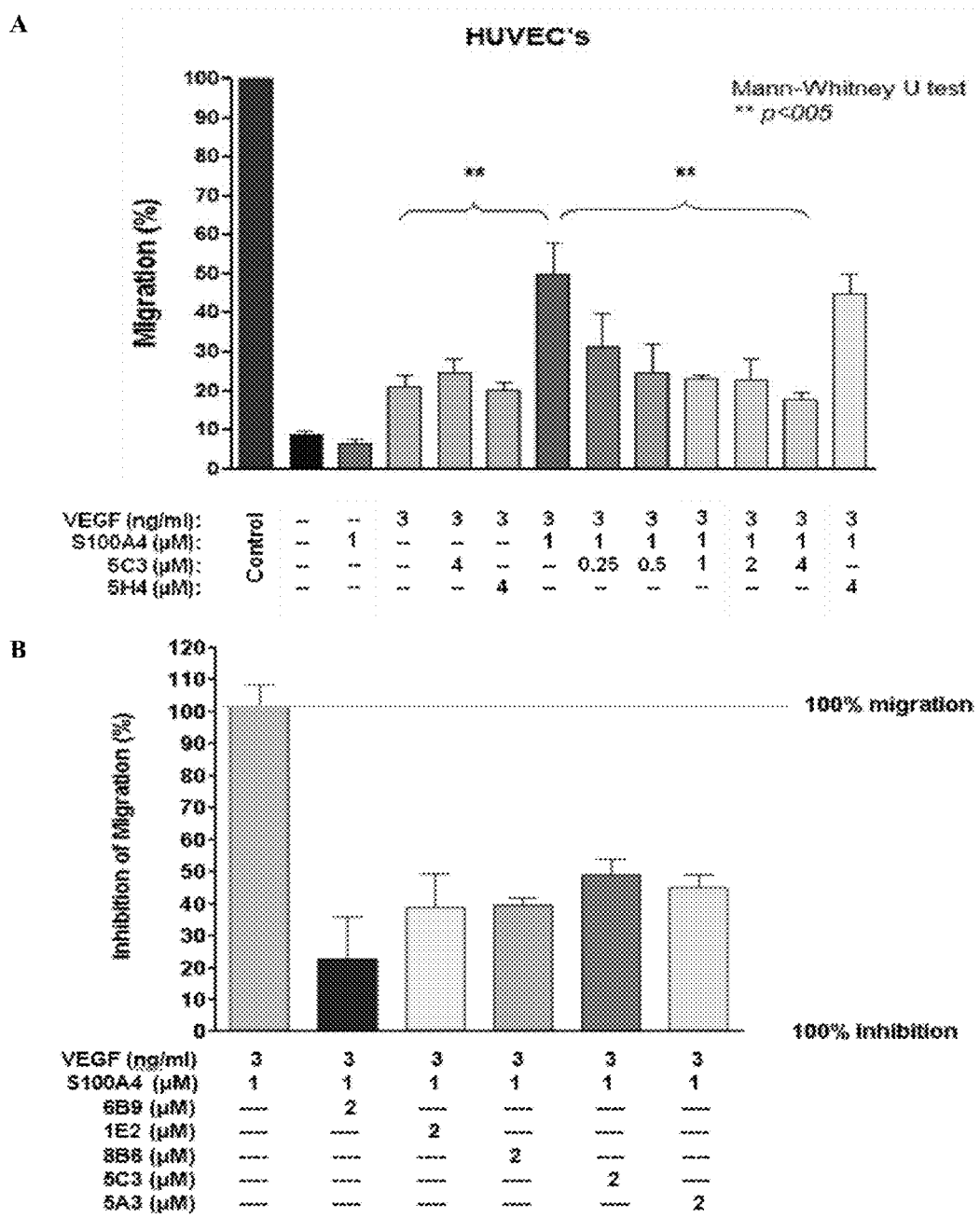
FIG. 4 Inhibitory effect of several monoclonal antibodies against S100A4 in HUVEC's migration. Before induction of migration, antibodies were incubated with the S100A4 protein for 2 h at 37° C. HUVEC's were treated with S100A4 (1 µM), VEGF (3 ng/ml), the combination of VEGF plus S100A4 or the combination of these proteins with the antibodies (5C3, 1E2, 8B6, 6B9, 5A3, 5H4) for 24 h. (A) Cells were treated with 5C3 (0.25, 0.5, 1, 2, and 4 µM) and the 5H4 (4 µM), for 24 h. Each data point is normalized to the positive control (left bar) that represents the 100% of migration. The positive control corresponds to cells incubated with EBM plus supplements (EGM) and FCS (complete medium). (B) Cells were treated with 5C3, 1E2, 8B6, 6B9, 5A3 (2 µM) for 24 h. Each data point is normalized to the migration induced by VEGF plus S100A4 that represents the 100% of migration. Bars show the mean±s-d. **p<0.005 ("Mann-Whitney U test").

This experiment demonstrated for the first time that the combination of S100A4 and other angiogenic factor (VEGF) increased synergistically the migratory activity of HUVECs. S100A4 was tested in a dose of 1 µM, exhibiting no significant activity as compared to the control -EBM. Incubation of HUVECs with 3 ng/mL of VEGF alone increased migration in a 2.4-fold, respectively, as compared to the EBM. When VEGF (3 ng/mL) was combined with S100A4 (1 µM), synergistic effect were observed (FIG. 4). In particular, when recombinant S100A4 (1 µM) was added together with VEGF (3 ng/mL), migration was increased by 235% compared to the effect of VEGF alone.

We also used the monoclonal antibodies anti-S100A4 (5C3, 1E2, 6B9, 8B6, 5A3) to inhibit the promigratory activity of S100A4. As shown in FIG. 4A, 250 nM of 5C3 abolished the synergistic effect of the combination of VEGF (3 ng/mL) plus S100A4 (1 µM) on HUVECs migration. The inhibition of migration due to 5C3 was dose-dependent. The antibody did not affect migration induced by VEGF alone. By contrast, other monoclonal antibody anti-S100A4 called 5H4 did not show neutralizing effect. FIG. 4B shown the inhibitory activity of others monoclonal antibodies against S100A4 compared with 5C3 working all at 2 µM. Taken together, with the biochemical data, these results demonstrate that 5C3, 1E2, 6B9, 8B6 and 5A3 specifically binds S100A4 and shows in vitro neutralizing activity induced by S100A4 on HUVECs migration.

Example 10

5C3 Blocks MiaPACA-2 and HCT116 Tumor Development in Nude Mice

Tumor xenografts are commonly used to evaluate response, where chemotherapeutic results have potential clinical relevance for cancer chemotherapy. Tumor xenografts are thus good models to correlate xenograft data with the clinical data. Drug testing with different types of xenotransplanted tumors has shown that the response of xenografts obtained in immune-deficient animals is comparable to that in clinical practice. In addition, xenografts of a particular tumor type are able to identify agents of known clinical activity against that disease.

MiaPACA-2 human pancreatic adenocarcinoma cell line and HCT116 human colorectal adenocarciona cell line in exponential growth were harvested with trypsin-EDTA (0.05%/0.02%) (Invitrogen), washed, and examined for viability by trypan blue dye exclusion. Viability was greater than 95%. For primary tumor growth, cells (either $5\times10^6$ or $1\times10^6$ cells for MiaPACA-2 or HCT116 respectively in 0.1 mL DMEM high glucose) were subcutaneously injected into the flanks of nude mice. Tumor volumes between 65-160 mm$^3$ for MiaPACA-2 and volumes between 155-370 mm$^3$ for HCT116 were used to divide the mice into two groups of either ten mice each (MiaPACA-2) or seven mice each (HCT116), such that the mean tumor size was equal between groups (approximately 100 mm$^3$ for MiaPACA-2 or 220 mm$^3$ for HCT 116). Tumor growth was followed by measuring tumor diameters with calipers and the tumor volume was calculated using an approximated formula for a prolate ellipsoid:

$$\text{volume} = (D \times d^2)/2$$

where D is the longest axis of the tumor and d the shortest. Mice were treated either with vehicle (PBS) or with the antibody, i.p. three times per week at 25 mg/Kg/100 µL of sterile PBS, starting the treatment at defined tumor volume (100 mm$^3$ and 220 mm$^3$). At the end of the experiment animals were killed, tumors were surgically removed, weighed and half tumor were embedded in OCT compound for subsequent CD31 immunostaining analyses and the other half tumor were fixed in formaldehyde for subsequent analyses. Blood samples from animals bearing MiaPACA-2 or HCT116 tumors were collected at the end of the experiment (all animals), using EDTA-coated material. Immediately after, plasma samples were centrifuged for 10 min at 5000 rpm, at room temperature and stored at −20° C. until analysis.

Comparisons between groups were made using the two-tailed nonparametric Mann Whitney U test. Differences for which P value was less than 0.05 were considered statistically significant.

Figure 5:
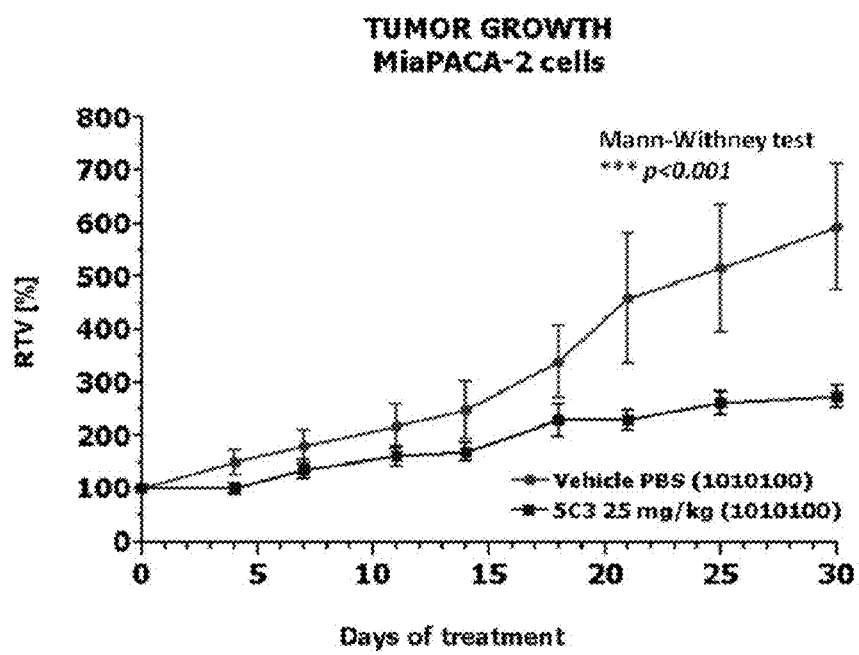
FIG. 5. Anti-tumor activity of 5C3 antibody in human pancreatic (MiaPACA-2) tumors. Female, athymic, nude mice were inoculated subcutaneously with $5 \times 10^6$ MiaPACA-2 cells in 0.1 ml culture medium without supplements, into the right upper flank of mice on day 0. When tumors reached 65-160 mm³ for MiaPACA-2 cells, the treatment was initiated. Treatment groups had 10 animals. PBS (negative control) or 5C3 (25 mg/kg) was given intraperitoneally three times a week (1010100). Final formulation buffer was given as vehicle control. Tumor size was measured three times per week and tumor volume was calculated according to the equation: tumor size=width². length/2. At the end of experiment (day 30 for MiaPACA-2 cells), mice bearing tumors were sacrificed and tumors were removed and weighted. (A, B) Results for MiaPACA-2 experiment. Graphs of relative tumor volume and tumor weight show the mean±s-d ns p>0.05, *p<0.05, ***p<0.001 ("Mann-Whitney U test").
Figure 5:
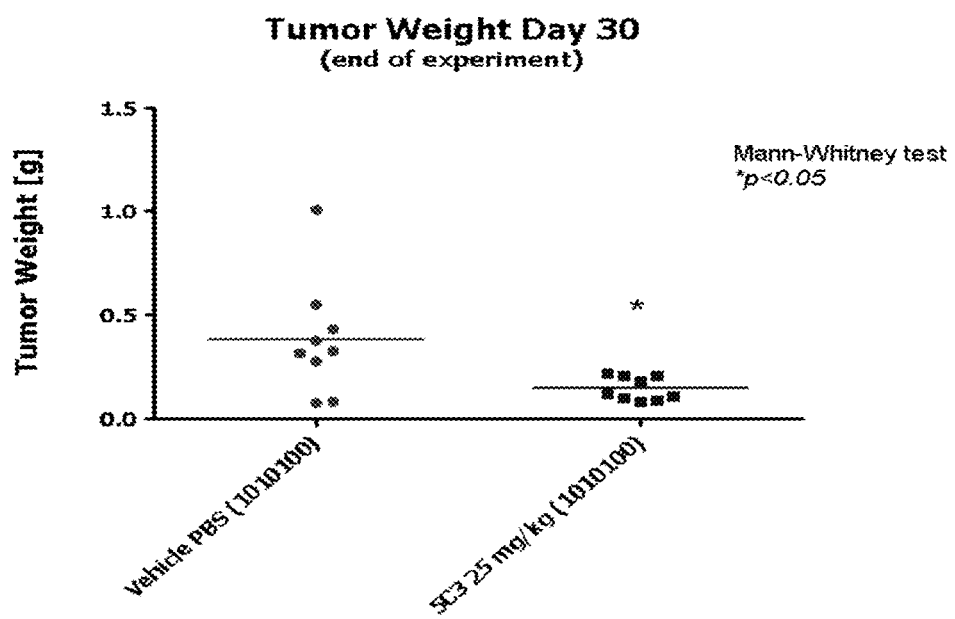

The inventors investigated the effect of the 5C3 on the subcutaneous development of MiaPACA-2 (FIG. 5) or HCT116 tumors in athymic nude mice. Either MiaPACA-2/HCT116 cell lines or developed tumors from MiaPACA-2/HCT116 in nude mice show high levels of S100A4 protein expression and secretion of the protein into the culture media and into the blood, respectively (data not shown). Due to the role of S100A4 in pancreatic and colorectal tumors and the evidence that the protein is secreted by these cell line, we decided to try this model to test the in vivo activity of our monoclonal antibody 5C3.

Figure 6:
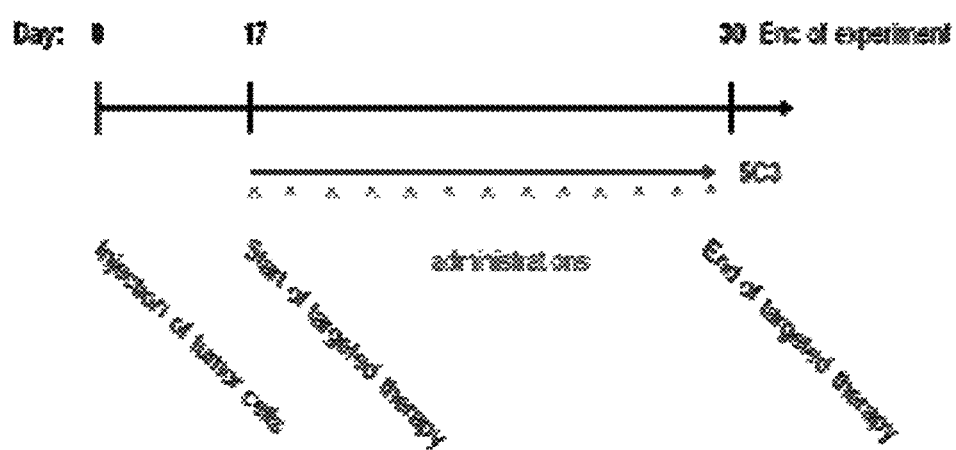
FIG. 6. Dosing schedule with monoclonal antibody 5C3 in nude mice.

Xenografts were implanted and grown, tumor-bearing animals randomly assigned and treated as described above. Treatment was initiated 17 days after cell implantation for MiaPACA-2 (mean tumor volume of each group higher than 100 mm$^3$) (day 0), and tumors were collected at day 30 after treatment. Treatment was initiated 23 days after cell implantation for HCT116 (mean tumor volume of each group higher than 220 mm$^3$) (day 0). 5C3 was given by intraperitoneal route (25 mg/kg), administered three times at week dosing schedule as shown in FIG. 6 (example for MiaPACA-2).

FIG. 5A shows the comparative analysis of the antitumoral activity of 5C3 along time for MiaPACA-2 tumor-bearing mice. Control group (vehicle) exhibited maximum tumor growth with mean relative tumor volume of 592% respect to the initial volume (before treatment). Tumor volume changes in 5C3-injected mice showed maximum mean relative tumor volume of 274% (day 30) respect to the initial volume. In connection with these data, we have observed (FIG. 5B) that treatment with 5C3, also induced a statistically significant decrease in tumor weight compared with the control group at the end of experiment (day 30). In addition, these differences are reflected on the T/C ratios of tumor volume and tumor weight calculated; 46%, and 38%, respectively.

Antitumoral activity of 5C3 along time for HCT116 tumor-bearing mice. Control group (vehicle) exhibited maximum tumor growth with mean relative tumor volume of 557% respect to the initial volume (before treatment). Tumor volume changes in 5C3-injected mice showed maximum mean relative tumor volume of 511% (day 21) respect to the initial volume. In connection with these data, we have observed (data not shown) that treatment with 5C3, induced a decrease in tumor weight compared with the control group at the end of experiment (day 21) higher than the observed in tumor volume valuation. In addition, these differences are reflected on the T/C ratios (Treatment vs Control group) of tumor volume and tumor weight calculated; 91%, and 74%, respectively.

Therefore, we demonstrate for the first time that treatment with a monoclonal antibody against S100A4 induced a statistically significant marked delay in tumor growth compared with non-treatment group (vehicle) for MiaPACA-2 human pancreatic tumor and an increased in intratumoral necrosis in HCT116 human colorectal tumor affecting the tumour weight.

Example 11

5C3 Blocks the Tumor Microvasculature Formation

Experimental evidence suggests that the growth of a tumor beyond a certain size requires angiogenesis, which may also permit metastasis. To investigate how tumor angiogenesis correlates with metastases in carcinomas, investigators counted microvessels (capillaries and venules) and graded the density of microvessels within the initial invasive carcinomas. The microvessel count and density grade also correlated with distant metastases. Assessment of tumor angiogenesis may therefore prove valuable in selecting patients with early breast carcinoma for aggressive therapy.

Tumors from MiaPACA-2 xenograft tumor model were OCT (Tissue-Tek®, Sakura) embedded and frozen. One cryosection (5 μm) corresponding to the central part of each tumor was analyzed. Sections were fixed in acetone/chloroform (1:1) at −20° C. for 5 min, were dried over night at room temperature, washed with PBS and treated for 10 min at 4° C. in a dark chamber with $H_2O_2$ (0.03%) in PBS. Then, sections were washed with PBS and blocked for 20 min at 4° C. using PBS-BSA (2%) plus rabbit serum (5%) (Vector) and with Avidin-biotin blocking solution (Dako) for 10 min each one at 4° C. Samples were incubated for 1 hour at room temperature with primary antibody; a monoclonal rat anti-mouse antibody directed against CD31 (dil 1:200, BD PharMingen) diluted in blocking buffer. After incubation sections were incubated with a polyclonal biotinilated anti-rat antibody as secondary antibody (dil 1:500, Vector) for 30 min at room temperature and were incubated with the ABC reagent (Pierce) for 30 min at room temperature. Finally, sections were incubated with NovaRed (Vector) for 20 min at 4° C., stained with hematoxilin Harris (Sigma) for 10 seconds and mounted using DPX non aqueous mounting medium (Sigma).

Angiogenesis quantification was measured using two criteria:

$$M.V.D(v.p./mm^2) = 10^6 \times \frac{\text{Sum of vessels of each tumour (image } A + \text{image } B + \ldots + \text{image } N)}{\text{Area of one tumour in } \mu m^2 (\text{area } A + \text{area } B + \ldots + \text{area } N)}$$

$$A.A(\text{fractional area of vessels}) = \frac{\text{Area of vessels of each tumour (image } A + \text{image } B + \ldots + \text{image } N)}{\text{Area of one tumour in } \mu m^2 (\text{area } A + \text{area } B + \ldots + \text{area } N)}$$

8 and 39 pictures per slice, depending on the size of tumours, were taken and analyzed using the NIH ImageJ imaging software.

Comparisons between groups were made using the two-tailed nonparametric Mann Whitney U test. Differences for which P value was less than 0.05 were considered statistically significant.

The inventors investigated whether the 5C3 would actually affect tumor angiogenesis in vivo. The evaluation of tumor angiogenesis was made based on the CD31 immunostaining and two analytics approximations: MicroVessel Density (M.V.D.) and the fractional area of vessels (A.A.).

Table 2 shows all taken data, animal by animal, in relation to the number of analyzed pictures for each subcutaneous MiaPACA-2 tumor, total area of vessels, number of vessels, total area of tumor, and the M.V.D. and % A.A. quantifications.

TABLE 2

Comparison of tumor angiogenesis quantification between control group and 5C3 treated group.

|  | N° pictures | Area of vessels (mm$^2$) | N° of vessels | Area of tumor (mm$^2$) | M.V.D. (v.p./mm$^2$) | % A.A. |
|---|---|---|---|---|---|---|
| G1#1 | 17 | 163232.8 | 445 | 9835265.19 | 45.25 | 1.66 |
| G1#2 | 23 | 91308.11 | 420 | 13570619.39 | 30.95 | 0.67 |
| G1#5 | 23 | 186919.87 | 647 | 12925880.79 | 50.05 | 1.45 |
| G1#6 | 20 | 120203.31 | 395 | 10467766.84 | 37.73 | 1.15 |
| G1#7 | 30 | 128668.51 | 428 | 17116234.97 | 25.01 | 0.75 |
| G1#8 | 8 | 57991.79 | 177 | 4401690.15 | 40.21 | 1.32 |
| G1#9 | 23 | 191851.7 | 691 | 13201926.3 | 52.34 | 1.45 |
| G1#10 | 39 | 201871.47 | 758 | 21987453.76 | 34.47 | 0.92 |
| G2#1 | 29 | 185583.19 | 514 | 16290934.48 | 31.55 | 1.14 |
| G2#2 | 19 | 130528.29 | 460 | 10367720.6 | 44.37 | 1.26 |

TABLE 2-continued

Comparison of tumor angiogenesis quantification between control group and 5C3 treated group.

| | | | | | |
|---|---|---|---|---|---|
| G2#3 | 21 | 62690.42 | 240 | 11861612.23 | 20.23 | 0.53 |
| G2#4 | 21 | 49860.26 | 203 | 12078084.8 | 16.81 | 0.41 |
| G2#5 | 26 | 96805.14 | 440 | 14742897.14 | 29.84 | 0.66 |
| G2#6 | 21 | 84539.29 | 426 | 11757524.57 | 36.23 | 0.72 |
| G2#7 | 16 | 29042.45 | 158 | 9126560.08 | 17.31 | 0.32 |
| G2#9 | 14 | 39705.98 | 174 | 7550280.16 | 23.05 | 0.53 |

| | AA (%) Median | AA (%) Mean | SEM | MVD (v.p./mm$^2$) Median | MVD (v.p./mm$^2$) Mean | SEM |
|---|---|---|---|---|---|---|
| G1 (PBS) | 1.23 | 1.17 | 0.13 | 38.97 | 39.50 | 3.33 |
| G2 (5C3) | 0.59 | 0.69 | 0.12 | 26.45 | 27.42 | 3.47 |

G1 (Vehicle control group), G2 (5C3 treatment group).
M.V.D. (MicroVascular Density) and % A.A. (Fractional area of vessels) quanfitications.

Figure 7:
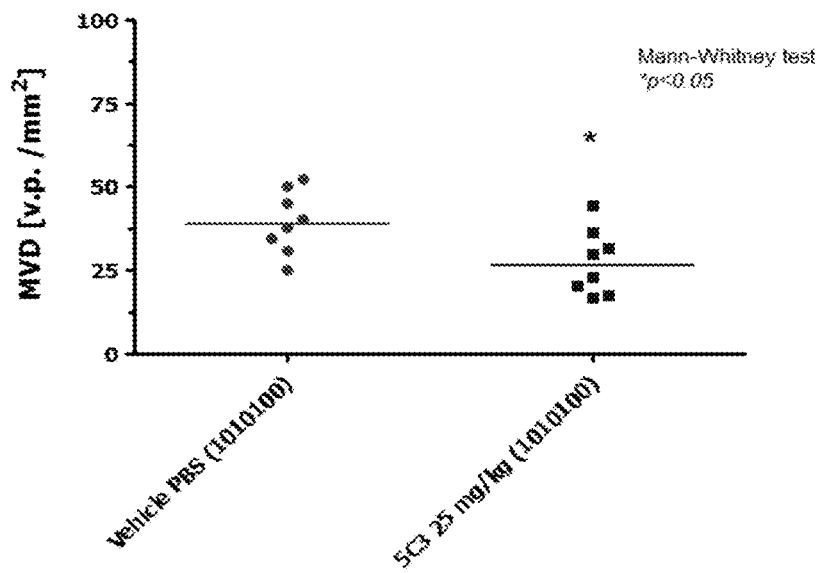
FIG. 7. Quantification of tumor microvasculature. Immunohistological analisis of microvasculature (murine CD31 monoclonal antibody) from MiaPACA-2 tumors. Levels of vasculature were measured at the end of experiment (day 30) comparing PBS control group and animals treated whit monoclonal antibody 5C3. (A) Vascular density in a defined tumor area (MVD) expressed as the mean of vascular profiles (v.p.) per mm². (B) Quantification of vessel area in the tumor (Aa).
Figure 7:
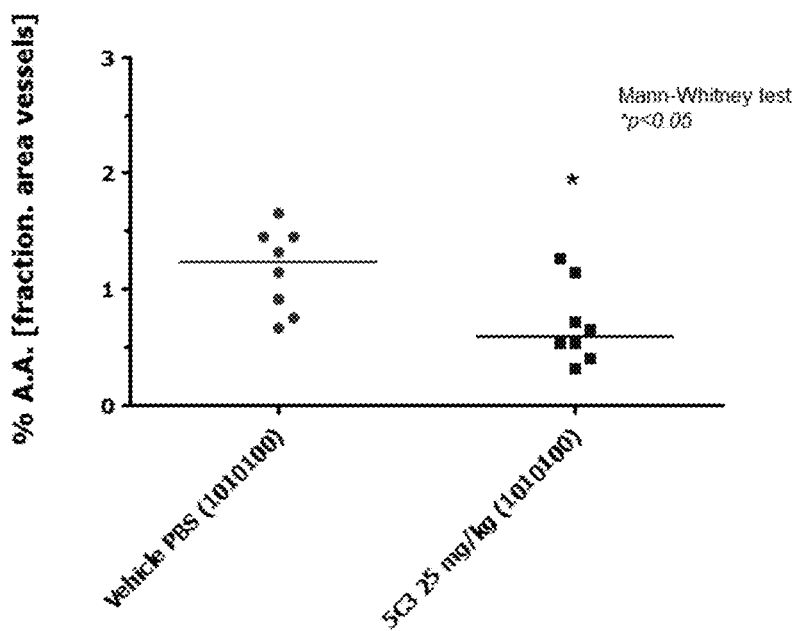

Tumors from animals treated with the monoclonal antibody 5C3 showed a reduction of approximately 40% in microvessel density and 30% of the section area occupied by vessels compared with animals from the control group (vehicle). As shown in FIG. 7, these differences in intratumoral microvessels were statistically significant.

Our experimental data revealed that the effect of the 5C3 blocking the tumor development could be in part due to a strongest reduction of tumor angiogenesis.

Example 12

5C3 Treatment does not Induce Body Weight Loss or Adverse Side Effects

The body weight profile at the administration day of the 5C3-treated and vehicle control group were monitored previous to administration along the experiment. No body weight loss was observed in any group and treatments were not interrupted.

FIG. 8 shows the animals' body weight profile along the experiment. 5C3 was well-tolerated at 25 mg/kg in a dosing schedule of three times a week up to the end of experiment.

Macroscopic analyses of the animals did not evidence abnormalities in organs. We did not observe adverse side effects (motor incoordination, paralysis, ataxia, convulsions, diarrhea, cachexia, erythema, hypothermia, mortality) in any animal along the experiment.

Example 13

Plasma Quantification of S100A4 in Xenograft Tumor Model

There is a need for early detection of tumors and metastasis, critical process for improving treatment in cancer patients. The detection of molecular biomarkers using non-invasive simple tests as blood based quantification methods are one of most clinical needs to detect the presence of a tumor, and monitor cancer therapy.

Plasma levels of S100A4 were quantified by sandwich ELISA method. Briefly, 96 microtiter plates (Maxisorb, NUNC) were coated with 10 µg/ml of monoclonal antibody 5C3 diluted in PBS (100 µl/well) 24 h at 4° C. After removing the coating, plates were washed twice with PBS and incubated 1 h at 37° C. in blocking buffer (PBS containing 1% of skimmed milk).

Plasma samples diluted 1:4 in dilution buffer (PBS-4% BSA) were applied to the wells (100 µl/well) and were incubated 2 h at 37° C. Plates were washed eight times with washing buffer (PBS-0.1% of Tween-20) and Rabbit polyclonal anti-S100A4 secondary antibody (Dako) at the appropriate dilution was applied to the wells (100 µl/well) and were incubated for 1 h at 37° C.

Plates were washed eight times with washing buffer and Goat anti-Rabbit-IgG-peroxidase conjugated (Sigma) at the appropriate dilution was added to each well (100 µl/well) and were incubated 1 h at 37° C. After washing eight times with washer buffer, the ELISA was revealed adding 100 µl of Tetramethylbenzidine substrate (Sigma) and were incubated 30 min at RT before stopping with 1M of HCl. Absorbance was ridden at 450 nm.

Standard curve for basal plasma samples (animals without tumor), was obtained by serial dilutions of murine recombinant S100A4 in dilution buffer. Standard curve for final plasma samples (animals with tumor at the end of the experiment) was obtained by serial dilutions of human recombinant S100A4 in dilution buffer.

FIG. 9 shows the quantification of plasma levels of S100A4 in animals carrying out subcutaneous tumor (mean of tumor volumes between 600-1000 mm3 approximately) of several MiaPACA-2, Colo205, MDA-MB-231 and HCT116 cell lines. Experimental data demonstrated the consistent difference between the basal expression of S100A4 protein in animals without tumors (basal-02) and the expression at the end of the experiment when the animals presented tumors.

FIG. 9 also shows the S100A4 protein levels in animals treated with the monoclonal antibody 5C3 (MiaPACA-2 and HCT116 xenograft tumor model) indicating that the corresponding treatment (see example 10) blocks the totality of circulant S100A4 protein in plasma.

Example 14

Epitope Determination of Monoclonal Antibodies 5C3, 1E2, 6B9. 8B6 and 5A3

The determination of the epitopic region of antibody recognition was assessed by ELISA. Briefly, the full length sequence of the human S100A4 protein was fractionated in nine overlapping peptides. 96 microtiter plates (Maxisorb, NUNC) were coated with 3 µg/ml of each peptide diluted in PBS (100 µl/well) 24 h at 4° C. Antibodies anti-S100A4 diluted at 5 µg/ml in dilution buffer (PBS-1% of BSA) were applied into the wells (100 µl/well) and were incubated 90 minutes at 37° C. Plates were washed eight times with washing buffer (PBS-0.1% of Tween-20) and Goat anti-Mouse-IgG-peroxidase conjugated (Jackson Immunoresearch) at the appropriate dilution was added to each well (100 μl/well) and was incubated 30 minutes at 37° C. After washing eight times with washer buffer, the ELISA was revealed adding 100 μl of Tetramethylbenzidine substrate (Sigma) and were incubated 15 minutes at RT before stopping with 1M of HCl. Absorbance was ridden at 450 nm.

Table 3 shows the region of human S100A4 recognized by the functional 5C3, 1E2, 6B9, 8B6 and 5A3 monoclonal antibodies. Note that 8B6 antibody did not recognize any of nine designed lineal peptide, giving us the possibility that it recognizes a conformational region of the protein. Another monoclonal antibody against human S100A4, called 5H4, used as negative control in migration assays, recognizes a different region (VMVSTFHKYSGKEGDKFKLN) (SEQ ID NO: 26).

TABLE 3

Sequences of S100A4 recognized by monoclonal antibodies.

| Monoclonal antibody | S100A4 sequence | Deposit number |
|---|---|---|
| 5C3 | ELPSFLGKRT (SEQ ID NO: 3) | 10022401 |
| 1E2 | EGFPDKQPRKK (SEQ ID NO: 24) | 11051803 |
| 6B9 | EGFPDKQPRKK (SEQ ID NO: 24) | 11051801 |
| 5A3 | EGFPDKQPRKK (SEQ ID NO: 24) | 11051802 |
| 8B6 | — | 11051804 |

Example 15

Cytotoxic Effect of Gemcitabine and 5C3

Cancer is a multistep and a multifactor process and therefore therapeutic strategies directed to different molecular targets or tumor compartments are currently the best options to combat this disease. Conventional chemotherapy as gemcitabine, a standard first-line treatment for advanced pancreatic cancer, is extensively utilized, but offers only a modest benefit due to the acquirement of chemoresistance and multiple adverse effects. Thus, is necessary to identify less toxic targeted agents that can sensitize several tumor compartments and that in combination with the standard chemotherapy will be more effective to kill the tumour cells. To improve the antitumor effect and to identify new reagents for pancreatic cancer treatment, we investigated the effects of the monoclonal antibody 5C3 in combination with gemcitabine on cellular proliferation and viability in human MiaPACA-2 pancreatic cancer cell line.

Cytotoxic effect of gemcitabine and the monoclonal antibody 5C3 was measured by hexosaminidase activity. Briefly, MiaPACA-2 cells were plated onto 96-well cell culture plates ($5 \times 10^3$ cells/well) in 50 μl of DMEM medium. Twenty-for hours later, 50 μl of medium with several concentrations of gemcitabine alone or in combination with 5C3 (40 nM, 100 nM) was added to each well and were cultured for 72 hours. After removing the culture media cells were washed once with PBS. Sixty microliters of substrate solution (p-nitrophenol-N-acetyl-beta-D-glucosamide 7.5 mM, sodium citrate 0.1 M, 0.25% Triton X-100, pH 5.0,) was added to each well and plates were incubated at 37° C. for 2 hours; after this incubation time, a bright yellow appears and plates were developed by adding 90 μl of developer solution (Glycine 50 mM, EDTA 5 mM, pH 10.4), and the absorbance at 450 nm was measured by using a multi-well scanning spectrophotometer. Data analysis was done normalizing the results with the negative control (untreated cells) which were considered as 100% of viability.

Curves were adjusted using a sigmoidal dose-response (variable slope) equation, and EC50 values were obtained from the equation:

$$Y = \text{Bottom} + (\text{Top} - \text{Bottom})/(1 + 10^{((\log EC50 - X) * \text{Hill-Slope})})$$

where X is the logarithm of concentration and Y is the response. Y starts at Bottom and goes to Top with a sigmoid shape.

To evaluate the level of interaction (synergistic, additive or antagonist effect) between gemcitabine and 5C3, a variation of the method proposed by Chou-Talalay was used. Briefly, the effect of the gemcitabine plus 5C3 is quantified by the combination index (CI):

$$CI = (D)1/(Dm)1$$

where $(Dm)1 = EC50$ Drug 1 concentration and $(D)1 = EC50$ (Drug 1+Drug 2)

TABLE 4

Determining values (synergism, addition, antagonism) using de CI index:

| | |
|---|---|
| <0.1 | Very strong synergism |
| 0.1-0.3 | Strong synergism |
| 0.3-0.7 | Synergism |
| 0.7-0.85 | Moderate synergism |
| 0.85-0.9 | Slight synergism |
| 0.90-1.10 | Nearly additive |
| 1.20-1.45 | Slight antagonism |
| 1.45-3.3 | Antagonism |
| 3.3-10 | Strong Antagonism |
| >10 | Very strong antagonism |

FIG. 10 shows the effect in cell viability induced by treatments with gemcitabine alone and the combination of gemcitabine and two concentrations of the monoclonal antibody 5C3 in MiaPACA-2 cell line. The EC50 for the gemcitabine was 8.356 nM. The combination with the 5C3 shown an EC50 of 5.161 nM and 4.586 nM for 40 nM and 100 nM of the mAb respectively.

The determination of the CI index showed values of 0.61 and 0.54 for the combination of gemcitabine with 40 nM and 100 nM of 5C3 demonstrating a synergistically effect of the two compounds.

This experiment demonstrated for the first time, that the combination of a monoclonal antibody against S100A4 with the chemotherapeutic drug Gemcitabine can improve synergistically the effect of the drug alone. For this reason, monoclonal antibodies anti-S100A4 may prove to be novel candidates for using in combination with chemotherapeutic drugs for the treatment of patients with cancer.

Example 16

S100A4 Induce the Secretion of IL8 in THP1 Monocytes and Monoclonal Antibody 5C3 Blocks this Effect Chronic Inflammatory diseases comprise a large group of disorders characterized by activation of mononuclear cells, such as monocytes and lymphocytes. One of the hallmarks in chronic inflammation and autoimmune diseases is the intense activation and accumulation of the monocyte/macrophage cells. Activated monocytes and macrophages are the most important source of cytokines in most of chronic inflammatory disorders. Taking into account all these facts, it was investigated whether S100A4 blockade could be useful to treat the chronic inflammatory diseases where monocytes activation plays a pivotal role.

To evaluate the effect of 5C3 on monocyte activation; THP-1, a human monocytic cell line was exposed to S100A4 and the levels of secreted IL-8 levels were used as indicator of monocyte activation.

Cells of the human monocytic leukemia cell line THP-1 (ATCC) were grown in RPMI 1640 culture medium supplemented with 10% FCS and 1% penicillin/streptomycin, at 37° C. in 5% CO2 in a humidified incubator. Cells were plated at $5.0 \times 10^5$ cells/well. S100A4 and 5C3 antibody were incubated together for 1 hour before the addition of monocytes. Anti-mouse IgG (Fc specific) was always added in all the cases for preventing the Fc receptor response. Cell culture supernatants were collected after 24 h and stored at −20° C. The levels of IL-8 were analyzed by sandwich ELISA.

S100A4 activated human monocytes in a dose response manner inducing cytokine release (FIG. 11A). This response can be blocked by monoclonal antibody 5C3 (FIG. 11B). Both 5C3 and Anti-mouse IgG in absence of S100A4, have no effect on IL-8 levels (data not shown).

These facts suggest that 5C3 can be useful in the treatment of all chronic inflammatory diseases, such as rheumatoid arthritis, psoriatic arthritis, psoriasis, inflammatory bowel diseases, arteriosclerosis, multiple sclerosis, etc, where monocyte activation play a pivotal role in their pathophysiology.

DEPOSITS OF BIOLOGICAL MATERIAL

The hybridoma which produces the 5C3-1B8-1F4 anti-S100A4 monoclonal antibody was deposited in the European Collection of Cell Cultures (ECACC) (Porton Down, Salisbury, SP4 OJG, United Kingdom) under the conditions stipulated in the Budapest Treaty. It was deposited on 24 Feb. 2010 and the number assigned to said deposit was 10022401.

The hybridoma which produces the 6B9-1E8-2A8 anti-S100A4 monoclonal antibody was deposited in the European Collection of Cell Cultures (ECACC) (Porton Down, Salisbury, SP4 OJG, United Kingdom) under the conditions stipulated in the Budapest Treaty. It was deposited on 18 May 2011 and the number assigned to said deposit was ECACC 11051801.

The hybridoma which produces the 5A3-4A6-5B6 anti-S100A4 monoclonal antibody was deposited in the European Collection of Cell Cultures (ECACC) (Porton Down, Salisbury, SP4 OJG, United Kingdom) under the conditions stipulated in the Budapest Treaty. It was deposited on 18 May 2011 and the number assigned to said deposit was ECACC 11051802.

The hybridoma which produces the 1E2-2H4-2G8 anti-S100A4 monoclonal antibody was deposited in the European Collection of Cell Cultures (ECACC) (Porton Down, Salisbury, SP4 OJG, United Kingdom) under the conditions stipulated in the Budapest Treaty. It was deposited on 18 May 2011 and the number assigned to said deposit was ECACC 11051803.

The hybridoma which produces the 8B6-2F6-1H9-1H10 anti-S100A4 monoclonal antibody was deposited in the European Collection of Cell Cultures (ECACC) (Porton Down, Salisbury, SP4 OJG, United Kingdom) under the conditions stipulated in the Budapest Treaty. It was deposited on 18 May 2011 and the number assigned to said deposit was ECACC 11051804.

The invention claimed is:

1. A specific anti-S100A4 antibody having anti-angiogenic activity or a fragment thereof showing at least 50% of the anti-angiogenic activity of said antibody wherein the antibody is produced by a hybridoma selected from the group consisting of:
ECACC 10022401, ECACC 11051801, ECACC 11051802, ECACC 11051803 and ECACC 11051804.

2. The antibody or fragment thereof according to claim 1 produced by the hybridoma ECACC 10022401.

3. The antibody or fragment thereof according to claim 2 which comprises at least a VL region comprising the sequence SEQ ID NO: 1 and at least a VH region comprising the sequence SEQ ID NO: 2.

4. A hybridoma cell line selected from the group consisting of a cell line deposited with accession number ECACC 10022401, ECACC 11051801, ECACC 11051802, ECACC 11051803 and ECACC 11051804.

5. A pharmaceutical composition comprising a pharmaceutically effective amount of at least one specific anti-S100A4 antibody having anti-angiogenic activity or a fragment thereof showing at least 50% of the anti-angiogenic activity of said antibody wherein the antibody is produced by hybridoma selected from the group consisting of: ECACC 10022401, ECACC 11051801, ECACC 11051802, ECACC 11051803 and ECACC 11051804 and at least one pharmaceutically acceptable carrier.

6. A method of treatment of a disease selected from the group consisting of metastasis, a disease associated to an undesired angiogenesis and a disease associated with inflammation comprising administering to a subject in need of said treatment a pharmaceutically effective amount of a compound selected from:

A) a specific anti-S100A4 monoclonal antibody having anti-angiogenic activity or a fragment thereof showing at least 50% of the anti-angiogenic activity of said antibody wherein the antibody is selected from the group consisting of:
(i) An antibody that recognizes an epitope of S100A4 comprising the sequence ELPSFLGKRT (SEQ ID NO: 3);
(ii) An antibody that recognizes an epitope of S100A4 comprising the sequence EGFPDKQPRKK (SEQ ID NO: 24); and
(iii) An antibody produced by the hybridoma ECACC 11051804.

7. The method according to claim 6 wherein the disease is cancer.

8. A kit for diagnosing cancer or a disease associated with inflammation in a biofluid which comprises at least one specific anti-S100A4 antibody having anti-angiogenic activity or a fragment thereof showing at least 50% of the anti-angiogenic activity of said antibody wherein the antibody is produced by a hybridoma selected from the group ECACC 10022401, ECACC 11051801, ECACC 11051802, ECACC 11051803 and ECACC 11051804.

9. The method according to claim 6 wherein the specific anti-S100A4 antibody is an antibody produced by a hybridoma selected from the group consisting of ECACC 10022401, ECACC 11051801, ECACC 11051802, ECACC 11051803 and ECACC 11051804.

10. The method according to claim 6 wherein the specific anti-S100A4 antibody is an antibody produced by the hybridoma ECACC 10022401.

* * * * *

SEQUENCE LISTING

```
<160> NUMBER OF SEQ ID NOS: 26

<210> SEQ ID NO 1
<211> LENGTH: 112
<212> TYPE: PRT
<213> ORGANISM: Artificial Sequence
<220> FEATURE:
<223> OTHER INFORMATION: VL region of the 5C3 monoclonal antibody

<400> SEQUENCE: 1

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Thr Gly Gln Ser
        35                  40                  45

Pro Glu Leu Leu Ile Tyr Lys Val Ser Asn Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 2
<211> LENGTH: 115
```

```
<212> TYPE: PRT
<213> ORGANISM: Artificial Sequence
<220> FEATURE:
<223> OTHER INFORMATION: VH region of the 5C3 monoclonal antibody

<400> SEQUENCE: 2

Glu Ala Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Gln Glu Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Asp Asp Pro Lys Phe
    50                  55                  60

Gln Gly Lys Ala Ser Ile Thr Val Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Ser Tyr Ala Met Asp Tyr Trp Gly Gln Gly Thr Ser Val Thr
            100                 105                 110

Val Ser Ser
        115

<210> SEQ ID NO 3
<211> LENGTH: 10
<212> TYPE: PRT
<213> ORGANISM: Homo sapiens

<400> SEQUENCE: 3

Glu Leu Pro Ser Phe Leu Gly Lys Arg Thr
1               5                   10

<210> SEQ ID NO 4
<211> LENGTH: 336
<212> TYPE: DNA
<213> ORGANISM: Artificial Sequence
<220> FEATURE:
<223> OTHER INFORMATION: Polynucleotide coding for the FRs and CDRs of
      the light chain of the variable region of 5C3 monoclonal antibody

<400> SEQUENCE: 4
gatgttttga tgacccaaac tccactctcc ctgcctgtca gtcttggaga tcaagcctcc      60
atctcttgca gatctagtca gagtattgta catagtaatg aaacacccta tttagaatgg    120
tacctgcaga aaacaggcca gtctccagag ctcctgatct acaaagtttc caaccgactc    180
tctggggtcc cagacaggtt cagtggcagt ggatcaggga cagatttcac actcaagatc    240
agcagagtgg aggctgagga tctgggagtt tattactgct ttcaaggttc acatgttcca    300
ttcacgttcg gctcggggac aaagttggaa ataaaa                              336

<210> SEQ ID NO 5
<211> LENGTH: 345
<212> TYPE: DNA
<213> ORGANISM: Artificial Sequence
<220> FEATURE:
<223> OTHER INFORMATION: Polynucleotide coding for the FRs and CDRs of
      the heavy chain of the variable region of a 5C3 monoclonal
      antibody

<400> SEQUENCE: 5
gaggctcagc tgcagcagtc tggggcagag cttgtgaagc caggggcctc tgtcaagttg      60
```

```
tcctgcacag cctctggctt caacattcaa gagacctata tgcactgggt gaagcagagg    120
cctgaacagg gcctggagtg gattggaagg attgatcctg cgaatggtaa taccaaagat    180
gacccgaagt tccagggcaa ggcctctata acagtagaca catcctccaa cacagcctac    240
ctgcagctca gcagcctgac atctgaggac actgccgtct attactgtgc ttcaagttat    300
gctatggact actggggtca aggaacctca gtcaccgtct cctca                    345
```

<210> SEQ ID NO 6
<211> LENGTH: 30
<212> TYPE: DNA
<213> ORGANISM: Homo sapiens

<400> SEQUENCE: 6

```
gagctgccca gcttcttggg gaaaaggaca                                      30
```

<210> SEQ ID NO 7
<211> LENGTH: 23
<212> TYPE: PRT
<213> ORGANISM: Artificial Sequence
<220> FEATURE:
<223> OTHER INFORMATION: FRL1 region of the 5C3 monoclonal antibody

<400> SEQUENCE: 7

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 8
<211> LENGTH: 16
<212> TYPE: PRT
<213> ORGANISM: Artificial Sequence
<220> FEATURE:
<223> OTHER INFORMATION: CDRL1 region of 5C3 monoclonal antibody

<400> SEQUENCE: 8

Arg Ser Ser Gln Ser Ile Val His Ser Asn Gly Asn Thr Tyr Leu Glu
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: FRL2 region of 5C3 monoclonal antibody

<400> SEQUENCE: 9

Trp Tyr Leu Gln Lys Thr Gly Gln Ser Pro Glu Leu Leu Ile Tyr
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: CDRL2 region of the 5C3 monoclonal antibody

<400> SEQUENCE: 10

Lys Val Ser Asn Arg Leu Ser
1               5

<210> SEQ ID NO 11
<211> LENGTH: 32
<212> TYPE: PRT

```
<213> ORGANISM: Artificial Sequence
<220> FEATURE:
<223> OTHER INFORMATION: FRL3 region of the 5C3 monoclonal antibody

<400> SEQUENCE: 11

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 12
<211> LENGTH: 9
<212> TYPE: PRT
<213> ORGANISM: Artificial Sequence
<220> FEATURE:
<223> OTHER INFORMATION: CDRL3 region of the 5C3 monoclonal antibody

<400> SEQUENCE: 12

Phe Gln Gly Ser His Val Pro Phe Thr
1               5

<210> SEQ ID NO 13
<211> LENGTH: 10
<212> TYPE: PRT
<213> ORGANISM: Artificial Sequence
<220> FEATURE:
<223> OTHER INFORMATION: FRL4 region of the 5C3 monoclonal antibody

<400> SEQUENCE: 13

Phe Gly Ser Gly Thr Lys Leu Glu Ile Lys
1               5                   10

<210> SEQ ID NO 14
<211> LENGTH: 30
<212> TYPE: PRT
<213> ORGANISM: Artificial Sequence
<220> FEATURE:
<223> OTHER INFORMATION: FRH1 region of the 5C3 monoclonal antibody

<400> SEQUENCE: 14

Glu Ala Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Gln
            20                  25                  30

<210> SEQ ID NO 15
<211> LENGTH: 5
<212> TYPE: PRT
<213> ORGANISM: Artificial Sequence
<220> FEATURE:
<223> OTHER INFORMATION: CDRH1 region of the 5C3 monoclonal antibody

<400> SEQUENCE: 15

Glu Thr Tyr Met His
1               5

<210> SEQ ID NO 16
<211> LENGTH: 14
<212> TYPE: PRT
<213> ORGANISM: Artificial Sequence
<220> FEATURE:
<223> OTHER INFORMATION: FRH2 region of the 5C3 monoclonal antibody

<400> SEQUENCE: 16

Trp Val Lys Gln Arg Pro Glu Gln Gly Leu Glu Trp Ile Gly
1               5                   10
```

<210> SEQ ID NO 17
<211> LENGTH: 17
<212> TYPE: PRT
<213> ORGANISM: Artificial Sequence
<220> FEATURE:
<223> OTHER INFORMATION: CDRH2 region of the 5C3 monoclonal antibody

<400> SEQUENCE: 17

Arg Ile Asp Pro Ala Asn Gly Asn Thr Lys Asp Asp Pro Lys Phe Gln
1               5                   10                  15

Gly

<210> SEQ ID NO 18
<211> LENGTH: 32
<212> TYPE: PRT
<213> ORGANISM: Artificial Sequence
<220> FEATURE:
<223> OTHER INFORMATION: FRH3 region of the 5C3 monoclonal antibody

<400> SEQUENCE: 18

Lys Ala Ser Ile Thr Val Asp Thr Ser Ser Asn Thr Ala Tyr Leu Gln
1               5                   10                  15

Leu Ser Ser Leu Thr Ser Glu Asp Thr Ala Val Tyr Tyr Cys Ala Ser
            20                  25                  30

<210> SEQ ID NO 19
<211> LENGTH: 6
<212> TYPE: PRT
<213> ORGANISM: Artificial Sequence
<220> FEATURE:
<223> OTHER INFORMATION: CDRH3 region of the 5C3 monoclonal antibody

<400> SEQUENCE: 19

Ser Tyr Ala Met Asp Tyr
1               5

<210> SEQ ID NO 20
<211> LENGTH: 11
<212> TYPE: PRT
<213> ORGANISM: Artificial Sequence
<220> FEATURE:
<223> OTHER INFORMATION: FRH4 region of the 5C3 monoclonal antibody

<400> SEQUENCE: 20

Trp Gly Gln Gly Thr Ser Val Thr Val Ser Ser
1               5                   10

<210> SEQ ID NO 21
<211> LENGTH: 101
<212> TYPE: PRT
<213> ORGANISM: Homo sapiens

<400> SEQUENCE: 21

Met Ala Cys Pro Leu Glu Lys Ala Leu Asp Val Met Val Ser Thr Phe
1               5                   10                  15

His Lys Tyr Ser Gly Lys Glu Gly Asp Lys Phe Lys Leu Asn Lys Ser
            20                  25                  30

Glu Leu Lys Glu Leu Leu Thr Arg Glu Leu Pro Ser Phe Leu Gly Lys
            35                  40                  45

Arg Thr Asp Glu Ala Ala Phe Gln Lys Leu Met Ser Asn Leu Asp Ser
        50                  55                  60

Asn Arg Asp Asn Glu Val Asp Phe Gln Glu Tyr Cys Val Phe Leu Ser

```
                65                  70                  75                  80
Cys Ile Ala Met Met Cys Asn Glu Phe Phe Glu Gly Phe Pro Asp Lys
                    85                  90                  95

Gln Pro Arg Lys Lys
            100

<210> SEQ ID NO 22
<211> LENGTH: 41
<212> TYPE: DNA
<213> ORGANISM: Artificial Sequence
<220> FEATURE:
<223> OTHER INFORMATION: Forward primer

<400> SEQUENCE: 22
actcacatat ggcgtgccct ctggagaagg ccctggatgt g                        41

<210> SEQ ID NO 23
<211> LENGTH: 43
<212> TYPE: PRT
<213> ORGANISM: Artificial Sequence
<220> FEATURE:
<223> OTHER INFORMATION: Reverse primer

<400> SEQUENCE: 23

Ala Cys Thr Cys Ala Thr Gly Ala Gly Cys Thr Cys Ala Thr Cys Ala
1               5                   10                  15

Thr Thr Thr Cys Thr Thr Cys Cys Thr Gly Gly Cys Thr Gly Cys
            20                  25                  30

Thr Thr Ala Thr Cys Thr Gly Gly Gly Ala Ala
        35                  40

<210> SEQ ID NO 24
<211> LENGTH: 11
<212> TYPE: PRT
<213> ORGANISM: Homo sapiens

<400> SEQUENCE: 24

Glu Gly Phe Pro Asp Lys Gln Pro Arg Lys Lys
1               5                   10

<210> SEQ ID NO 25
<211> LENGTH: 104
<212> TYPE: PRT
<213> ORGANISM: Artificial Sequence
<220> FEATURE:
<223> OTHER INFORMATION: Fusion protein comprising the sequence
      of human S100A4 with an amino-terminus tail

<400> SEQUENCE: 25

Gly Ser His Met Ala Cys Pro Leu Glu Lys Ala Leu Asp Val Met Val
1               5                   10                  15

Ser Thr Phe His Lys Tyr Ser Gly Lys Glu Gly Asp Lys Phe Lys Leu
            20                  25                  30

Asn Lys Ser Glu Leu Lys Glu Leu Leu Thr Arg Glu Leu Pro Ser Phe
        35                  40                  45

Leu Gly Lys Arg Thr Asp Glu Ala Ala Phe Gln Lys Leu Met Ser Asn
    50                  55                  60

Leu Asp Ser Asn Arg Asp Asn Glu Val Asp Phe Gln Glu Tyr Cys Val
65                  70                  75                  80

Phe Leu Ser Cys Ile Ala Met Met Cys Asn Glu Phe Phe Glu Gly Phe
                85                  90                  95
```

```
Pro Asp Lys Gln Pro Arg Lys Lys
            100

<210> SEQ ID NO 26
<211> LENGTH: 20
<212> TYPE: PRT
<213> ORGANISM: Homo sapiens

<400> SEQUENCE: 26

Val Met Val Ser Thr Phe His Lys Tyr Ser Gly Lys Glu Gly Asp Lys
1               5                   10                  15

Phe Lys Leu Asn
            20
```